United States Patent
Zheng et al.

(10) Patent No.: US 11,643,465 B2
(45) Date of Patent: May 9, 2023

(54) ANTI-PD-1 ANTIBODIES

(71) Applicant: WuXi Biologies Ireland Limited, Dublin (IE)

(72) Inventors: Yong Zheng, Shanghai (CN); Jing Li, Lexington, MA (US); Zhisheng Chen, Shanghai (CN)

(73) Assignee: WuXi Biologics Ireland Limited, Dublin (IE)

( * ) Notice: Subject to any disclaimer, the term of this patent is extended or adjusted under 35 U.S.C. 154(b) by 127 days.

(21) Appl. No.: 17/239,866

(22) Filed: Apr. 26, 2021

(65) Prior Publication Data

US 2021/0355218 A1    Nov. 18, 2021

Related U.S. Application Data

(62) Division of application No. 15/751,236, filed as application No. PCT/CN2016/094624 on Aug. 11, 2016, now Pat. No. 11,008,391.

(30) Foreign Application Priority Data

Aug. 11, 2015  (WO) ............ PCTCN2015086594
Jan. 19, 2016  (WO) ............ PCTCN2016071374

(51) Int. Cl.
    *C07K 16/28*         (2006.01)
(52) U.S. Cl.
    CPC ...... *C07K 16/2818* (2013.01); *C07K 16/2827* (2013.01); *C07K 2317/21* (2013.01); *C07K 2317/22* (2013.01); *C07K 2317/31* (2013.01); *C07K 2317/33* (2013.01); *C07K 2317/34* (2013.01); *C07K 2317/565* (2013.01); *C07K 2317/74* (2013.01); *C07K 2317/76* (2013.01); *C07K 2317/92* (2013.01)

(58) Field of Classification Search
    None
    See application file for complete search history.

(56) References Cited

U.S. PATENT DOCUMENTS

| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |

(Continued)

FOREIGN PATENT DOCUMENTS

| CN | 101213297 | 7/2008 |
| CN | 101526890 | 9/2009 |

(Continued)

OTHER PUBLICATIONS

Australian Office Action in AU Patent Application No. 2016305697, dated Feb. 1, 2022, 4 pages.

(Continued)

*Primary Examiner* — Gary B Nickol
*Assistant Examiner* — Amelia Nicole Dickens
(74) *Attorney, Agent, or Firm* — Sheppard Mullin Richter & Hampton LLP

(57) ABSTRACT

The present disclosure provides monoclonal antibodies against protein programmed cell death 1 (PD-1), which can block the binding of PD-1 ligands to PD-1, and therefore block the inhibitory function of PD-1 ligands on PD-1 expressing T cells. The antibodies of disclosure provide very potent agents for the treatment of multiple cancers via modulating human immune function

9 Claims, 11 Drawing Sheets

Specification includes a Sequence Listing.

(56) References Cited

U.S. PATENT DOCUMENTS

| | | | |
|---|---|---|---|
| 4,927,762 | A | 5/1990 | Darfler |
| 5,122,469 | A | 6/1992 | Mather et al. |
| 6,005,079 | A | 12/1999 | Casterman et al. |
| 7,595,048 | B2 | 9/2009 | Honjo et al. |
| 7,638,492 | B2 | 12/2009 | Wood et al. |
| 7,851,598 | B2 | 12/2010 | Davis |
| 7,892,540 | B2 | 2/2011 | Chen et al. |
| 7,943,743 | B2 | 5/2011 | Korman et al. |
| 8,008,449 | B2 | 8/2011 | Korman et al. |
| 8,168,179 | B2 | 5/2012 | Honjo et al. |
| 8,354,509 | B2 | 1/2013 | Carven et al. |
| 8,460,886 | B2 | 6/2013 | Shibayama et al. |
| 8,728,474 | B2 | 5/2014 | Honjo et al. |
| 8,747,833 | B2 | 6/2014 | Chen et al. |
| 8,779,105 | B2 | 7/2014 | Korman et al. |
| 8,907,157 | B2 | 12/2014 | Buelow |
| 8,945,561 | B2 | 2/2015 | Davis |
| 8,952,136 | B2 | 2/2015 | Carven et al. |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,358,289 | B2 | 6/2016 | Korman et al. |
| 9,387,247 | B2 | 7/2016 | Korman et al. |
| 9,393,301 | B2 | 7/2016 | Honjo et al. |
| 9,402,899 | B2 | 8/2016 | Honjo et al. |
| 9,439,962 | B2 | 9/2016 | Honjo et al. |
| 9,492,539 | B2 | 11/2016 | Korman et al. |
| 9,492,540 | B2 | 11/2016 | Korman et al. |
| 9,803,015 | B2 | 10/2017 | Chen et al. |
| 9,856,320 | B2 | 1/2018 | Coqswell et al. |
| 10,087,251 | B2 | 10/2018 | Hermans et al. |
| 10,323,093 | B2 | 6/2019 | Cogswell et al. |
| 10,441,655 | B2 | 10/2019 | Korman et al. |
| 10,512,689 | B2 | 12/2019 | Sadineni et al. |
| 10,544,224 | B2 | 1/2020 | Manekas et al. |
| 10,604,575 | B2 | 3/2020 | Cogswell et al. |
| 11,008,391 | B2 | 5/2021 | Zheng et al. |
| 2014/0212422 | A1 | 7/2014 | Korman et al. |
| 2015/0203579 | A1 | 7/2015 | Papadopoulos et al. |
| 2016/0304607 | A1 | 10/2016 | Sadineni et al. |
| 2017/0037132 | A1 | 2/2017 | Manekas et al. |
| 2017/0158776 | A1 | 6/2017 | Feltauate et al. |
| 2018/0155429 | A1 | 6/2018 | Finckenstein |
| 2018/0162942 | A1 | 6/2018 | Simon et al. |
| 2018/0244781 | A1 | 8/2018 | Cuillerot et al. |
| 2018/0346569 | A1 | 12/2018 | Wana et al. |
| 2019/0112377 | A1 | 4/2019 | Coqswell et al. |
| 2019/0144542 | A1 | 5/2019 | Galler et al. |
| 2019/0194328 | A1 | 6/2019 | Yana |
| 2019/0263923 | A1 | 8/2019 | Jure-Kunkel et al. |
| 2019/0367616 | A1 | 12/2019 | Lantto et al. |
| 2020/0002420 | A1 | 1/2020 | Zhena et al. |
| 2020/0010549 | A1 | 1/2020 | Yang |
| 2020/0010550 | A1 | 1/2020 | Rietschel et al. |

FOREIGN PATENT DOCUMENTS

| | | |
|---|---|---|
| CN | 101763842 | 6/2010 |
| CN | 102131828 | 7/2011 |
| CN | 102737616 | 10/2012 |
| CN | 103242448 | 8/2013 |
| CN | 103701643 | 4/2014 |
| CN | 105336289 | 2/2016 |
| CN | 205017477 | 2/2016 |
| CN | 103608040 | 3/2017 |
| CN | 104250302 | 11/2017 |
| CN | 104479018 | 9/2018 |
| CN | 104479020 | 8/2019 |
| EP | 404097 | 6/1990 |
| EP | 402226 | 12/1990 |
| EP | 183070 | 10/1991 |
| EP | 244234 | 11/2001 |
| EP | 2152880 | 8/2011 |
| EP | 2360254 | 8/2011 |
| EP | 2336329 | 10/2012 |
| EP | 2857420 | 4/2015 |
| EP | 1810026 | 4/2018 |
| JP | 2006521783 | 9/2006 |
| JP | 2009155338 | 7/2009 |
| JP | 2010500872 | 1/2010 |
| WO | WO 1987/000195 | 1/1987 |
| WO | WO 1990/003430 | 4/1990 |
| WO | WO 1993/011161 | 6/1993 |
| WO | WO 1994/004678 | 3/1994 |
| WO | WO 1994/025591 | 11/1994 |
| WO | WO 2001/014557 | 3/2001 |
| WO | WO 2004/004771 | 1/2004 |
| WO | WO 2004/056875 | 7/2004 |
| WO | WO 2005/066867 | 7/2005 |
| WO | WO 2006/042237 | 4/2006 |
| WO | WO 2006/121168 | 11/2006 |
| WO | WO 2006/133396 | 12/2006 |
| WO | WO 2008/007144 | 6/2008 |
| WO | WO 2008/071447 | 6/2008 |
| WO | WO 2008/112003 | 9/2008 |
| WO | WO 2008/156712 | 12/2008 |
| WO | WO 2010/001617 | 1/2010 |
| WO | WO 2010/063011 | 6/2010 |
| WO | WO 2012/056407 | 5/2012 |
| WO | WO 2013/059524 | 4/2013 |
| WO | WO 2013/168327 | 11/2013 |
| WO | WO 2013/173223 | 11/2013 |
| WO | WO 2014/194302 | 12/2014 |
| WO | WO 2015/134605 | 9/2015 |
| WO | WO 2015/176033 | 11/2015 |
| WO | WO 2016/007235 | 1/2016 |
| WO | WO 2016/100561 | 6/2016 |
| WO | WO 2016/137985 | 9/2016 |
| WO | WO 2016/144673 | 9/2016 |
| WO | WO 2016/168716 | 10/2016 |
| WO | WO 2016/176503 | 11/2016 |
| WO | WO 2016/176504 | 11/2016 |
| WO | WO 2016/191751 | 12/2016 |
| WO | WO 2016/196389 | 12/2016 |
| WO | WO 2017/011666 | 1/2017 |
| WO | WO 2017/019896 | 2/2017 |
| WO | WO 2017/025051 | 2/2017 |
| WO | WO 2017/055547 | 4/2017 |
| WO | WO 2017/087599 | 5/2017 |
| WO | WO 2017/132508 | 8/2017 |
| WO | WO 2017/176925 | 10/2017 |
| WO | WO 2017/210453 | 12/2017 |
| WO | WO 2017/210624 | 12/2017 |
| WO | WO 2017/210637 | 12/2017 |
| WO | WO 2018/053709 | 3/2018 |
| WO | WO 2018/081621 | 5/2018 |
| WO | WO 2018/091661 | 5/2018 |
| WO | WO 2018/132287 | 7/2018 |
| WO | WO 2018/156494 | 8/2018 |
| WO | WO 2018/183928 | 10/2018 |
| WO | WO 2018/204368 | 11/2018 |
| WO | WO 2018/223040 | 12/2018 |
| WO | WO 2019/023624 | 1/2019 |
| WO | WO 2019/062642 | 4/2019 |
| WO | WO 2019/075468 | 4/2019 |
| WO | WO 2019/080872 | 5/2019 |

OTHER PUBLICATIONS

Indian Office Action in IN Patent Application No. 201817004239, dated Feb. 9, 2022, 9 pages.
Mexican Office Action in MX Patent Application No. MX/a/2018/001644, dated Dec. 10, 2021, 9 pages (with English translation).
Adderson et al., NCBI GenBank database, Accession No. AAA59031.1, immunoglobulin lambda-chain, partial [*Homo sapiens*], Jan. 5, 1995, 1 page.
Al-Lazikani et al., "Standard conformations for the canonical structures of immunoglobulins," J. Mol. Biol., 1997, 273(4):927.
Altschul et al., "Basic local alignment search tool," J. Mol. Biol., 1990, 215:403-410.
Altschul et al., "Gapped BLAST and PSI-BLAST: a new generation of protein database search programs," Nucleic Acids Res, 1997, 25:3389-3402.

(56) References Cited

OTHER PUBLICATIONS

Barnes et al., "Methods for growth of cultured cells in serum-free medium," Anal. Biochem., 1980, 102:255.
Bendig, "Humanization of rodent monoclonal antibodies by CDR grafting", Methods: A Companion to Methods in Enzymology, 1995, 8:83-93.
Cappelli et al., "Inflammatory arthritis and sicca syndrome induced by nivolumab and ipilimumab", Ann Rheum Disease, 2016, 0:1-8.
Carter et al., "High level *Escherichia coli* expression and production of a bivalent humanized antibody fragment," Bio/Technology, 1992, 10:163-167.
Chen et al, "Enhancement and destruction of antibody function by somatic mutation: unequal occurrence is controlled by V gene combinatorial associations", The EMBO Journal, 1995, 14(12):2784-2794.
Chien et al., "Significant structural and functional change of an antigen-binding site by a distant amino acid substitution: Proposal of a structural mechanism", Proc. Natl. Acad. Sci, Jul. 1989, 86:5532-5536.
Chothia et al., "Canonical structures for the hypervariable regions of immunoglobulins," J.Mol.Biol., 1987, 196(4):901-17.
Chothia et al., "Conformations of immunoglobulin hypervariable regions," Nature., Dec. 21-28, 1989;342(6252):877-83.
Chothia et al., "Domain association in immunoglobulin molecules. The packing of variable domains," J Mol Biol., 1985, 186(3):651-63.
Dahan et al., "TCR-like antibodies distinguish conformational and functional differences in two-versus four-domain auto reactive MHC class II-peptide complexes," Eur J Immunol., 2011, 41:1465.
Extended European Search Report dated Feb. 28, 2019, for EP Patent Application No. 16834675,7, 16 pages.
Flisikowska et al., "Efficient immunoglobulin gene disruption and targeted replacement in rabbit using zinc finger nucleases," PLoS One, 2011, 6:e21045.
Freeman et al., "Engagement of the PD-1 immunoinhibitory receptor by a novel B7 family member leads to negative regulation of lymphocyte activation," J Exp. Med, 2000, 192:1027-1034.
GenBank Accession No. AEZ52328.1, "Immunoglobulin alpha heavy chain variable region, partial [*Homo sapiens*]", May 31, 2012, retrieved on Jul. 16, 2021, retrieved from URL <"https://www.ncbi.nlm.nih.gov/protein/AEZ52328.1">, 2 pages.
Geurts et al., "Knockout Rats via Embryo Microinjection of Zinc-Finger Nucleases", Science, Jul. 2009, 325(5939):433.
Graham et al., "Characteristics of a human cell line transformed by DNA from human adenovirus type 5," J. Gen Virol., 1977, 36:59.
Griffiths et al., "Human anti-self antibodies with high specificity from phage display libraries", The EMBO Journal, 1993, 12(2):725-734.
Guss et al., "Structure of the IgG-binding regions of streptococcal protein G," EMBO J., 1986, 5:1567-1575.
Ham et al., "Media and growth requirements," Meth. Enz., 1979, 58:44.
Hamers-Casterman et al., "Naturally occurring antibodies devoid of light chains," Nature, 1993, 363(6428):446-8.
Hao et al., "Epitope characterization of an anti-PD-L1 antibody using orthogonal approaches," Molecular Recognition, 2015, 28:269.
Higgins et al., "[22] Using CLUSTAL for multiple sequence alignments", Methods in Enzymology, 1996, 266:383-402.
Holliger et al., "Diabodies: small bivalent and bispecific antibody fragments," Proc Natl Acad Sci USA, 1993, 90(14):6444-8.
Huston et al., "Protein engineering of antibody binding sites: recovery of specific activity in an anti-digoxin single-chain Fv analogue produced in *Escherichia coli*," Pmc Natl Acad Sci USA, 1988, 85:5879.
Ignatovich et al., NCBI GenBank database, Accession No. AAF20468.1, immunoglobulin lambda light chain variable region [*Homo sapiens*], (Jan. 10, 2000), 1 page.
Ignatovich et al., NCBI GenBank database, Accession No. AAF20469.1, immunoglobulin lambda light chain variable region [*Homo sapiens*], (Jan. 10, 2000), 1 page.

Ishida et al., "Production of human monoclonal and polyclonal antibodies in TransChromo animals," Cloning Stem Cells, 2002, 4:91-102.
Koch-Nolte et al., "Single domain antibodies from llama effectively and specifically block T cell ecto-ADP-ribosyltransferase ART2.2 in vivo," FASEB J., 2007, 21(13):3490-8.
Kussie et al., "A Single Engineered Amino Acid Substitution Changes Antibody Fine Specificity", Journal of Immunology, 1994, 152:146-152.
Larkin et al., "Clustal W and Clustal X version 2.0," Bioinformatics, 2007, 23(21): 2947-8.
Lee et al., "Complete humanization of the mouse immunoglobulin loci enables efficient therapeutic antibody discovery," Nat Biotechnol, 2014, 32:356-363.
Lindmark et al., "Binding of immunoglobulins to protein A and immunoglobulin levels in mammalian sera," J. Immunol. Meth., 1983, 62:1-13.
Lonberg et al., "Antigen-specific human antibodies from mice comprising four distinct genetic modifications," Nature, 1994, 368(6474): 856-859.
Ma et al., "Human antibody expression in transgenic rats: comparison of chimeric IgH loci with human VH, D and JH but bearing different rat C-gene regions," Journal of Immunological Methods, 2013, 100-401:78-86.
Mather et a., "Culture of testicular cells in hormone-supplemented serum-free medium," Annals NY. Acad. Sci., 1982, 383:44-68.
Mather, "Establishment and characterization of two distinct mouse testicular epithelial cell lines," Biol. Reprod., 1980, 23:243-251.
McDermott et al., "PD-1 as a potentil target in cancer therapy", Cancer Medicine, 2013, 2(5):662-673.
Mendez et al., "Functional transplant of megabase human immunoglobulin loci recapitulates human antibody response in mice," Nat Genet, 1997, 15:146-156.
Murphy et al., "Mice with megabase humanization of their immunoglobulin genes generate antibodies as efficiently as normal mice," Proc Natl Acad Sci USA, 2014, 111:5153-5158.
Muyldermans et al., "Single domain camel antibodies: current status," J. Biotechnol., 2001, 74(4):277-302.
NCBI accession No. N, P_054862.1, "Programmed cell death 1 ligand 1 isoform a precursor [*Homo sapiens*]", Jul. 11, 2021, 4 pages.
NCBI accession No. NM_005018.2, "Programmed cell death 1 ligand 1 isoform a precursor [*Homo sapiens*]", Jul. 11, 2021, 4 pages.
NCBI accession No. NM_014143.3, "*Homo sapiens* CD274 molecule (CD274), transcript variant 1, mRNA", Oct. 14, 2018, 5 pages.
NCBI accession No. NP_005009.2, "Programmed cell death protein 1 precursor [*Homo sapiens*]", Jul. 5, 2021, 4 pages.
Nguyen et al. "Heavy-chain antibodies in Camelidae; a case of evolutionary innovation," Imnmnogeneticsm 2002, 54(1):39-47.
Nguyen et al., "Heavy-chain only antibodies derived from dromedary are secreted and displayed by mouse B cells," Immunology, 2003, 109(1):93-101.
Osborn et al., "High-affinity IgG antibodies develop naturally in Ig-knockout rats carrying germline human IgH/Igκ/Igλ loci bearing the rat CH region," Journal of Immunology, 2013, 190:1481-90.
Pal et al., NCBI GenBank database, Accession No. AA047766.1, immunoglobulin lambda light chain VLJ region [*Homo sapiens*], (Mar. 4, 2003), 1 page.
Partial Supplementary European Search Report dated Dec. 11, 2018, for EP Patent Application No. 16834675.7, 15 pages.
Paul, Fundamental Immunology, 3rd Edition, 1993, pp. 292-295.
PCT International Preliminary Report on Patentability in International Application No. PCT/CN2015/086594, dated Feb. 13, 2018, 9 pages.
PCT International Preliminary Report on Patentability in International Application No. PCT/CN2016/095624, dated Dec. 18, 2018, 8 pages (with English translation).
PCT International Search Report and Written Opinion corresponding to PCT/CN2016/095624 dated Nov. 3, 2016, 19 pages.

(56) References Cited

OTHER PUBLICATIONS

PCT International Search Report and Written Opinion in International Application No. PCT/CN2015/086594, dated May 18, 2016, 15 pages.
Perez De La Lastra et al., "Epitope mapping of 10 monoclonal antibodies against the pig analogue of human membrane cofactor protein (MCP)," Immunology, Apr. 1999, 96(4):663-670.
Riechmann et al., "Single domain antibodies: comparison of camel VH and camelised human VH domains," J Immunol Methods., 1999, 231(1-2):25-38.
Rudikoff et al., "Single amino acid substitution altering antigen-binding specificity", PNAS, 1982, 79: 1979-1983.
Saudi Arabian Office Action in SA Patent Application No. 518390903, dated Jan. 21, 2021, 17 pages (with English translation).
Topalian et al., "Safety, Activity, and Immune Correlations of Anti-PD-1 Antibody in Cancer", The New England Journal of Medicine, 2012, 366(26):2443-2454.
Ukrainian Office Action in UA Patent Application No. a201802340, dated Feb. 16, 2021, 13 pages (with English translation).
Urlaub et al., "Isolation of Chinese hamster cell mutants deficient in dihydrofolate reductase activity," Proc. Natl. Acad. Sci. USA, 1980, 77:4216.

| Analyte | Ligand | ka (1/Ms) | kd (1/s) | KD (M) | Rmax (RU) | Chi² (RU) |
|---|---|---|---|---|---|---|
| WBP305.hpro1.ECD.his | 1.7.3 hAb | 1.70E+06 | 2.98E-04 | 1.76E-10 | 61.9 | 2.63 |
| | 1.49.9 hAb | 1.08E+06 | 1.16E-03 | 1.07E-09 | 44.15 | 2.43 |
| | 1.103.11 hAb (305-2) | 1.12E+06 | 1.96E-04 | 1.75E-10 | 54.14 | 2.58 |
| | 1.139.15 hAb | 1.05E+06 | 3.89E-03 | 3.71E-09 | 65.02 | 2.16 |
| | 1.153.7 hAb (305-1) | 2.62E+05 | 7.33E-04 | 2.79E-09 | 53.54 | 2.05 |

SEQUENCE LISTING

<160> NUMBER OF SEQ ID NOS: 68

<210> SEQ ID NO 1
<211> LENGTH: 7
<212> TYPE: PRT
<213> ORGANISM: Homo sapiens

<400> SEQUENCE: 1

Ser Thr Thr Tyr Tyr Trp Val
1               5

<210> SEQ ID NO 2
<211> LENGTH: 21
<212> TYPE: DNA
<213> ORGANISM: Homo sapiens

<400> SEQUENCE: 2
agtactactt actactgggt c                                            21

<210> SEQ ID NO 3
<211> LENGTH: 16
<212> TYPE: PRT
<213> ORGANISM: Homo sapiens

<400> SEQUENCE: 3

Ser Ile Ser Tyr Ser Gly Asn Thr Tyr Tyr Asn Pro Ser Leu Lys Ser
1               5                   10                  15

<210> SEQ ID NO 4
<211> LENGTH: 48
<212> TYPE: DNA
<213> ORGANISM: Homo sapiens

<400> SEQUENCE: 4
agtatctctt atagtgggaa cacctactac aatccgtccc tcaagagt                48

<210> SEQ ID NO 5
<211> LENGTH: 13
<212> TYPE: PRT
<213> ORGANISM: Homo sapiens

<400> SEQUENCE: 5

His Leu Gly Tyr Asn Gly Arg Tyr Leu Pro Phe Asp Tyr
1               5                   10

<210> SEQ ID NO 6
<211> LENGTH: 39
<212> TYPE: DNA
<213> ORGANISM: Homo sapiens

<400> SEQUENCE: 6
catctagggt ataatgggag gtacctcccc tttgactac                          39

<210> SEQ ID NO 7
<211> LENGTH: 14
<212> TYPE: PRT
<213> ORGANISM: Homo sapiens

<400> SEQUENCE: 7

Thr Gly Thr Ser Ser Asp Val Gly Phe Tyr Asn Tyr Val Ser
1               5                   10

<210> SEQ ID NO 8
<211> LENGTH: 42

```
<212> TYPE: DNA
<213> ORGANISM: Homo sapiens

<400> SEQUENCE: 8
actggaacca gcagtgacgt tggtttttat aactatgtct cc                 42

<210> SEQ ID NO 9
<211> LENGTH: 7
<212> TYPE: PRT
<213> ORGANISM: Homo sapiens

<400> SEQUENCE: 9

Asp Val Thr Asn Arg Pro Ser
1               5

<210> SEQ ID NO 10
<211> LENGTH: 21
<212> TYPE: DNA
<213> ORGANISM: Homo sapiens

<400> SEQUENCE: 10
gatgtcacta atcggccctc a                                        21

<210> SEQ ID NO 11
<211> LENGTH: 10
<212> TYPE: PRT
<213> ORGANISM: Homo sapiens

<400> SEQUENCE: 11

Ser Ser Tyr Thr Ser Ile Ser Thr Trp Val
1               5                   10

<210> SEQ ID NO 12
<211> LENGTH: 30
<212> TYPE: DNA
<213> ORGANISM: Homo sapiens

<400> SEQUENCE: 12
agctcatata caagcatcag cacttgggtg                               30

<210> SEQ ID NO 13
<211> LENGTH: 7
<212> TYPE: PRT
<213> ORGANISM: Homo sapiens

<400> SEQUENCE: 13

Ser Ser Thr Tyr Tyr Trp Gly
1               5

<210> SEQ ID NO 14
<211> LENGTH: 21
<212> TYPE: DNA
<213> ORGANISM: Homo sapiens

<400> SEQUENCE: 14
agtagtactt actactgggg c                                        21

<210> SEQ ID NO 15
<211> LENGTH: 16
<212> TYPE: PRT
<213> ORGANISM: Homo sapiens

<400> SEQUENCE: 15

Ser Ile Ser Tyr Ser Gly Ser Thr Tyr Tyr Asn Pro Ser Leu Lys Ser
```

<210> SEQ ID NO 16
<211> LENGTH: 48
<212> TYPE: DNA
<213> ORGANISM: Homo sapiens

<400> SEQUENCE: 16
agtatctctt atagtgggag cacctactac aatccgtccc tcaagagt        48

<210> SEQ ID NO 17
<211> LENGTH: 7
<212> TYPE: PRT
<213> ORGANISM: Homo sapiens

<400> SEQUENCE: 17

Asp Val Ser Asn Arg Pro Ser
1               5

<210> SEQ ID NO 18
<211> LENGTH: 21
<212> TYPE: DNA
<213> ORGANISM: Homo sapiens

<400> SEQUENCE: 18
gatgtcagta atcggccctc a        21

<210> SEQ ID NO 19
<211> LENGTH: 10
<212> TYPE: PRT
<213> ORGANISM: Homo sapiens

<400> SEQUENCE: 19

Ser Ser Tyr Thr Asn Ile Ser Thr Trp Val
1               5                   10

<210> SEQ ID NO 20
<211> LENGTH: 30
<212> TYPE: DNA
<213> ORGANISM: Homo sapiens

<400> SEQUENCE: 20
agctcatata caaacatcag cacttgggtg        30

<210> SEQ ID NO 21
<211> LENGTH: 7
<212> TYPE: PRT
<213> ORGANISM: Homo sapiens

<400> SEQUENCE: 21

Ser Thr Thr Tyr Tyr Trp Gly
1               5

<210> SEQ ID NO 22
<211> LENGTH: 21
<212> TYPE: DNA
<213> ORGANISM: Homo sapiens

<400> SEQUENCE: 22
agtactactt actactgggg c        21

<210> SEQ ID NO 23
<211> LENGTH: 16
<212> TYPE: PRT

<213> ORGANISM: Homo sapiens

<400> SEQUENCE: 23

Ser Ile Ser Tyr Ser Gly Thr Thr Tyr Tyr Asn Pro Ser Leu Lys Ser
1               5                   10                  15

<210> SEQ ID NO 24
<211> LENGTH: 48
<212> TYPE: DNA
<213> ORGANISM: Homo sapiens

<400> SEQUENCE: 24
agtatctctt atagtgggac cacctactac aacccgtccc tcaagagt         48

<210> SEQ ID NO 25
<211> LENGTH: 13
<212> TYPE: PRT
<213> ORGANISM: Homo sapiens

<400> SEQUENCE: 25

His Leu Gly Tyr Asn Ser Asn Trp Tyr Pro Phe Asp Tyr
1               5                   10

<210> SEQ ID NO 26
<211> LENGTH: 39
<212> TYPE: DNA
<213> ORGANISM: Homo sapiens

<400> SEQUENCE: 26
catctcgggt ataacagcaa ctggtaccct tttgactac              39

<210> SEQ ID NO 27
<211> LENGTH: 14
<212> TYPE: PRT
<213> ORGANISM: Homo sapiens

<400> SEQUENCE: 27

Thr Gly Thr Ser Ser Asp Val Gly Ser Tyr Asn Arg Val Ser
1               5                   10

<210> SEQ ID NO 28
<211> LENGTH: 42
<212> TYPE: DNA
<213> ORGANISM: Homo sapiens

<400> SEQUENCE: 28
actggaacca gcagtgacgt tggtagttat aaccgtgtct cc           42

<210> SEQ ID NO 29
<211> LENGTH: 7
<212> TYPE: PRT
<213> ORGANISM: Homo sapiens

<400> SEQUENCE: 29

Glu Val Ser Asn Arg Pro Ser
1               5

<210> SEQ ID NO 30
<211> LENGTH: 21
<212> TYPE: DNA
<213> ORGANISM: Homo sapiens

<400> SEQUENCE: 30
gaggtcagta atcggccctc a                                 21

<210> SEQ ID NO 31
<211> LENGTH: 10
<212> TYPE: PRT
<213> ORGANISM: Homo sapiens

<400> SEQUENCE: 31

Ser Ser Tyr Thr Ser Ser Ser Thr Trp Val
1               5                   10

<210> SEQ ID NO 32
<211> LENGTH: 30
<212> TYPE: DNA
<213> ORGANISM: Homo sapiens

<400> SEQUENCE: 32
agctcatata caagcagcag cacttgggtg                                          30

<210> SEQ ID NO 33
<211> LENGTH: 5
<212> TYPE: PRT
<213> ORGANISM: Homo sapiens

<400> SEQUENCE: 33

Ser His Ala Met Ser
1               5

<210> SEQ ID NO 34
<211> LENGTH: 15
<212> TYPE: DNA
<213> ORGANISM: Homo sapiens

<400> SEQUENCE: 34
agccatgcca tgagc                                                          15

<210> SEQ ID NO 35
<211> LENGTH: 17
<212> TYPE: PRT
<213> ORGANISM: Homo sapiens

<400> SEQUENCE: 35

Thr Ile Thr Gly Gly Gly Gly Ser Ile Tyr Tyr Ala Asp Ser Val Lys
1               5                   10                  15

Gly

<210> SEQ ID NO 36
<211> LENGTH: 51
<212> TYPE: DNA
<213> ORGANISM: Homo sapiens

<400> SEQUENCE: 36
actattactg gtggtggtgg tagcatatac tacgcagact ccgtgaaggg c                  51

<210> SEQ ID NO 37
<211> LENGTH: 10
<212> TYPE: PRT
<213> ORGANISM: Homo sapiens

<400> SEQUENCE: 37

Asn Arg Ala Gly Glu Gly Tyr Phe Asp Tyr
1               5                   10

<210> SEQ ID NO 38

```
<211> LENGTH: 30
<212> TYPE: DNA
<213> ORGANISM: Homo sapiens

<400> SEQUENCE: 38
aaccgcgctg gggagggtta ctttgactac                                    30

<210> SEQ ID NO 39
<211> LENGTH: 11
<212> TYPE: PRT
<213> ORGANISM: Homo sapiens

<400> SEQUENCE: 39

Gly Gly Asp Asn Ile Gly Asn Lys Asp Val His
1               5                   10

<210> SEQ ID NO 40
<211> LENGTH: 33
<212> TYPE: DNA
<213> ORGANISM: Homo sapiens

<400> SEQUENCE: 40
gggggagaca acattggaaa taaagatgtg cac                                33

<210> SEQ ID NO 41
<211> LENGTH: 7
<212> TYPE: PRT
<213> ORGANISM: Homo sapiens

<400> SEQUENCE: 41

Arg Asp Ser Asn Arg Pro Ser
1               5

<210> SEQ ID NO 42
<211> LENGTH: 21
<212> TYPE: DNA
<213> ORGANISM: Homo sapiens

<400> SEQUENCE: 42
agggatagca accggccctc t                                             21

<210> SEQ ID NO 43
<211> LENGTH: 8
<212> TYPE: PRT
<213> ORGANISM: Homo sapiens

<400> SEQUENCE: 43

Gln Val Trp Asp Ser Ile Trp Val
1               5

<210> SEQ ID NO 44
<211> LENGTH: 24
<212> TYPE: DNA
<213> ORGANISM: Homo sapiens

<400> SEQUENCE: 44
caggtgtggg acagcatttg ggtg                                          24

<210> SEQ ID NO 45
<211> LENGTH: 123
<212> TYPE: PRT
<213> ORGANISM: Homo sapiens

<400> SEQUENCE: 45
```

Gln Leu Gln Leu Gln Glu Ser Gly Pro Gly Leu Val Lys Pro Ser Glu
1               5                   10                  15

Thr Leu Thr Leu Thr Cys Thr Val Ser Gly Asp Ser Ile Ser Ser Thr
            20                  25                  30

Thr Tyr Tyr Trp Val Trp Ile Arg Gln Pro Pro Gly Lys Gly Leu Glu
        35                  40                  45

Trp Ile Gly Ser Ile Ser Tyr Ser Gly Asn Thr Tyr Tyr Asn Pro Ser
    50                  55                  60

Leu Lys Ser Arg Val Thr Ile Ser Val Asp Thr Ser Lys Asn His Phe
65                  70                  75                  80

Ser Leu Lys Leu Ser Ser Val Ala Ala Thr Asp Thr Ala Leu Tyr Tyr
            85                  90                  95

Cys Ala Arg His Leu Gly Tyr Asn Gly Arg Tyr Leu Pro Phe Asp Tyr
        100                 105                 110

Trp Gly Gln Gly Thr Leu Val Thr Val Ser Ser
        115                 120

<210> SEQ ID NO 46
<211> LENGTH: 369
<212> TYPE: DNA
<213> ORGANISM: Homo sapiens

<400> SEQUENCE: 46
cagctgcagc tgcaggagtc gggcccagga ctggtgaagc cttcggagac cctgaccctc    60
acctgcactg tctctggtga ctccatcagc agtactactt actactgggt ctggatccgc   120
cagcccccag gaagggact ggagtggatt gggagtatct cttatagtgg aaacacctac    180
tacaatccgt ccctcaagag tcgagtcacc atatccgtag acacgtccaa gaaccacttc   240
tccctgaagc tgagttctgt ggccgccaca gacacggctc tatattactg tgcgagacat   300
ctagggtata atggaggta cctcccctttt gactactggg gccagggaac cctggtcacc   360
gtctcctcc                                                           369

<210> SEQ ID NO 47
<211> LENGTH: 110
<212> TYPE: PRT
<213> ORGANISM: Homo sapiens

<400> SEQUENCE: 47

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Glu Leu
        35                  40                  45

Met Ile Tyr Asp Val Thr Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ile
            85                  90                  95

Ser Thr Trp Val Phe Gly Gly Gly Thr Lys Leu Thr Val Leu
        100                 105                 110

<210> SEQ ID NO 48
<211> LENGTH: 330
<212> TYPE: DNA

<213> ORGANISM: Homo sapiens

<400> SEQUENCE: 48

```
cagtctgccc tgactcagcc tgcctccgtg tctgggtctc ctggacagtc gatcaccatc    60
tcctgcactg gaaccagcag tgacgttggt ttttataact atgtctcctg gtaccaacag   120
cacccaggca aagcccccga actcatgatt tatgatgtca ctaatcggcc ctcaggggtt   180
tctgatcgct tctctggctc caagtctggc aacacggcct ccctgaccat ctctgggctc   240
caggctgagg acgaggctga ttattactgc agctcatata caagcatcag cacttgggtg   300
ttcggcggag ggaccaagct gaccgtccta                                    330
```

<210> SEQ ID NO 49
<211> LENGTH: 123
<212> TYPE: PRT
<213> ORGANISM: Homo sapiens

<400> SEQUENCE: 49

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Thr Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Asp Ala Asp Thr Ala Val Tyr Tyr
                85                  90                  95

Cys Ala Arg His Leu Gly Tyr Asn Gly Arg Tyr Leu Pro Phe Asp Tyr
            100                 105                 110

Trp Gly Gln Gly Thr Leu Val Thr Val Ser Ser
        115                 120

<210> SEQ ID NO 50
<211> LENGTH: 369
<212> TYPE: DNA
<213> ORGANISM: Homo sapiens

<400> SEQUENCE: 50

```
cagctgcagc tgcaggagtc gggcccagga ctggtgaagc cttcggagac cctgtccctc    60
acctgcactg tctctggtgg ctccatcagc agtagtactt actactgggg ctggatccgc   120
cagcccccag ggaagggact ggagtggatt gggagtatct cttatagtgg gagcacctac   180
tacaatccgt ccctcaagag tcgagtcacc atatccgtag acacgtccaa gaaccagttc   240
tccctgaagc tgagctctgt gaccgacgca gacacggctg tgtattactg tgcgagacat   300
ctagggtata tgggaggta cctccccttt gactactggg gccagggaac cctggtcacc   360
gtctcctcc                                                           369
```

<210> SEQ ID NO 51
<211> LENGTH: 110
<212> TYPE: PRT
<213> ORGANISM: Homo sapiens

<400> SEQUENCE: 51

Gln Ser Ala Leu Thr Gln Pro Ala Ser Val Ser Gly Ser Pro Gly Gln

```
                1               5                  10                 15
            Ser Ile Thr Ile Ser Cys Thr Gly Thr Ser Ser Asp Val Gly Phe Tyr
                            20                 25                 30

Asn Tyr Val Ser Trp Tyr Gln Gln His Pro Gly Lys Ala Pro Glu Val
                            35                 40                 45

Met Ile Tyr Asp Val Ser Asn Arg Pro Ser Gly Val Ser Asp Arg Phe
                        50                 55                 60

Ser Gly Ser Lys Ser Gly Asn Thr Ala Ser Leu Thr Ile Ser Gly Leu
            65                 70                 75                 80

Gln Ala Glu Asp Glu Ala Asp Tyr Tyr Cys Ser Ser Tyr Thr Ser Ile
                                85                 90                 95

Ser Thr Trp Val Phe Gly Gly Gly Thr Lys Leu Thr Val Leu
                        100                105                110

<210> SEQ ID NO 52
<211> LENGTH: 330
<212> TYPE: DNA
<213> ORGANISM: Homo sapiens

<400> SEQUENCE: 52
cagtctgccc tgactcagcc tgcctccgtg tctgggtctc ctggacagtc gatcaccatc      60
tcctgcactg gaaccagcag tgacgttggt ttttataact atgtctcctg gtaccaacag     120
cacccaggca agcccccga agtcatgatt tatgatgtca gtaatcggcc ctcagggg tt     180 tctgatcgct tctctggctc caagtctggc aacacggcct ccctgactat ctctgggctc    240
caggctgagg acgaggctga ttattactgc agctcatata caagcatcag cacttgggtg    300
ttcggcggag ggaccaagct gactgtccta                                      330

<210> SEQ ID NO 53
<211> LENGTH: 123
<212> TYPE: PRT
<213> ORGANISM: Homo sapiens

<400> SEQUENCE: 53

Gln Leu Gln Leu Gln Glu Ser Gly Pro Gly Leu Val Lys Pro Ser Glu
            1               5                  10                 15

Thr Leu Thr Leu Thr Cys Thr Val Ser Ala Asp Ser Ile Ser Ser Thr
                            20                 25                 30

Thr Tyr Tyr Trp Val Trp Ile Arg Gln Pro Pro Gly Lys Gly Leu Glu
                        35                 40                 45

Trp Ile Gly Ser Ile Ser Tyr Ser Gly Ser Thr Tyr Tyr Asn Pro Ser
                        50                 55                 60

Leu Lys Ser Arg Val Thr Val Ser Val Asp Thr Ser Lys Asn Gln Phe
            65                 70                 75                 80

Ser Leu Lys Leu Asn Ser Val Ala Ala Thr Asp Thr Ala Leu Tyr Tyr
                                85                 90                 95

Cys Ala Arg His Leu Gly Tyr Asn Gly Arg Tyr Leu Pro Phe Asp Tyr
                        100                105                110

Trp Gly Gln Gly Thr Leu Val Thr Val Ser Ser
                        115                120

<210> SEQ ID NO 54
<211> LENGTH: 369
<212> TYPE: DNA
<213> ORGANISM: Homo sapiens

<400> SEQUENCE: 54
```

```
cagctgcagc tgcaggagtc gggcccagga ctggtgaagc cttcggagac cctgaccctc    60
acctgcactg tctctgctga ctccatcagc agtactactt actactgggt ctggatccgc   120
cagcccccag ggaagggact ggagtggatt gggagtatct cttatagtgg gagcacctac   180
tacaatccgt ccctcaagag tcgagtcacc gtatccgtag acacgtccaa gaaccagttc   240
tccctgaagc tgaactctgt ggccgccaca gacacggctc tatattactg tgcgagacat   300
ctagggtata atgggaggta cctccccttt gactactggg gccagggaac cctggtcacc   360
gtctcctcc                                                           369
```

<210> SEQ ID NO 55
<211> LENGTH: 110
<212> TYPE: PRT
<213> ORGANISM: Homo sapiens

<400> SEQUENCE: 55

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Glu Leu
        35                  40                  45

Met Ile Tyr Asp Val Ser Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asn Ile
                85                  90                  95

Ser Thr Trp Val Phe Gly Gly Gly Thr Lys Leu Thr Val Leu
            100                 105                 110

<210> SEQ ID NO 56
<211> LENGTH: 330
<212> TYPE: DNA
<213> ORGANISM: Homo sapiens

<400> SEQUENCE: 56

```
cagtctgccc tgactcagcc tgcctccgtg tctgggtctc ctggacagtc gatcaccatc    60
tcctgcactg gaaccagcag tgacgttggt ttttataact atgtctcctg gtaccaacag   120
cacccaggca aagcccccga actcatgatt tatgatgtca gtaatcggcc ctcagggggtt   180 tctgatcgct tctctggctc caagtctggc aacacggcct ccctgaccat ctctgggctc   240
caggctgagg acgaggctga ttattactgc agctcatata caaacatcag cacttgggtg   300
ttcggcggag ggaccaagct gaccgtccta                                    330
```

<210> SEQ ID NO 57
<211> LENGTH: 123
<212> TYPE: PRT
<213> ORGANISM: Homo sapiens

<400> SEQUENCE: 57

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Thr Tyr Tyr Trp Gly Trp Ile Arg Gln Pro Pro Gly Lys Gly Leu Glu 35                  40                  45
Trp Ile Gly Ser Ile Ser Tyr Ser Gly Thr Thr Tyr Tyr Asn Pro Ser
        50                  55                  60

Leu Lys Ser Arg Val Thr Ile Pro Val Asp Thr Ser Lys Asn Gln Ile
65                  70                  75                  80

Ser Leu Lys Leu Ser Ser Val Thr Ala Ala Asp Thr Ser Leu Tyr Tyr
                85                  90                  95

Cys Ala Arg His Leu Gly Tyr Asn Ser Asn Trp Tyr Pro Phe Asp Tyr
            100                 105                 110

Trp Gly Gln Gly Thr Leu Val Thr Val Ser Ser
        115                 120

<210> SEQ ID NO 58
<211> LENGTH: 369
<212> TYPE: DNA
<213> ORGANISM: Homo sapiens

<400> SEQUENCE: 58
cagctgcagc tgcaggagtc gggcccagga ctggtgaagc cctcggagac cctgtccctc      60
acctgcactg tctctggtgg ctccatcagc agtactactt actactgggg ctggatccgc     120
cagcccccag ggaaggggct ggagtggatt gggagtatct cttatagtgg gaccacctac     180
tacaacccgt ccctcaagag tcgagtcacc atccccgtag acacgtccaa gaaccagatc     240
tccctgaaac tgagctctgt gaccgccgca gacacgtctt tgtattattg cgagacat      300 ctcgggtata acagcaactg gtacccttt gactactggg gccagggaac cctggtcacc     360
gtctcctca                                                             369

<210> SEQ ID NO 59
<211> LENGTH: 110
<212> TYPE: PRT
<213> ORGANISM: Homo sapiens

<400> SEQUENCE: 59

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
                20                  25                  30

Asn Arg Val Ser Trp Tyr Gln Gln Pro Pro Gly Thr Ala Pro Glu Val
            35                  40                  45

Ile Ile Tyr Glu Val Ser Asn Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 60
<211> LENGTH: 330
<212> TYPE: DNA
<213> ORGANISM: Homo sapiens

<400> SEQUENCE: 60
cagtcggccc tgactcagcc tccctccgtg tccgggtctc ctggacagtc agtcaccatc      60
tcctgcactg gaaccagcag tgacgttggt agttataacc gtgtctcctg gtaccagcag     120

```
cccccaggca cagcccccga agtcattatt tatgaggtca gtaatcggcc ctcagggtc    180 cctgatcgct tctctgggtc caagtctggc aacacggcct ccctgaccat ctctgggctc   240
caggctgagg acgaggctga ttattactgc agctcatata caagcagcag cacttgggtg   300
ttcggcggag ggaccaagct gaccgtccta                                    330
```

```
<210> SEQ ID NO 61
<211> LENGTH: 119
<212> TYPE: PRT
<213> ORGANISM: Homo sapiens

<400> SEQUENCE: 61
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Thr Ile Thr Gly Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Ala Gly Glu Gly Tyr Phe Asp Tyr Trp Gly Gln Gly
            100                 105                 110

Thr Leu Val Thr Val Ser Ser
        115

```
<210> SEQ ID NO 62
<211> LENGTH: 357
<212> TYPE: DNA
<213> ORGANISM: Homo sapiens

<400> SEQUENCE: 62
```

```
gaggtgcagc tgttggagtc tgggggaggc ttggtacagc ctggggggtc cctgagactg    60
tcctgcgcag cctctggatt cacctttagc agccatgcca tgagctgggt ccgccaggct   120
ccagggaagg ggctggagtg ggtctcaact attactggtg gtggtggtag catatactac   180
gcagactccg tgaagggccg gttcaccatc tccagagaca attccaagaa cacgctgtat   240
ctgcaaatga acagcctgag agccgaggac acggccgtat attattgtgc gaaaaaccgc   300
gctggggagg gttactttga ctactggggc cagggaaccc tggtcaccgt ctcctca      357
```

```
<210> SEQ ID NO 63
<211> LENGTH: 105
<212> TYPE: PRT
<213> ORGANISM: Homo sapiens

<400> SEQUENCE: 63
```

Ser Tyr Glu Leu Thr Gln Pro Leu Ser Val Ser Val Ala Leu Gly Gln
1               5                   10                  15

Thr Ala Arg Ile Thr Cys Gly Gly Asp Asn Ile Gly Asn Lys Asp Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Gly Phe Ser Gly Ser

```
                   50                  55                  60
Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ser Ile Trp Val Phe
                 85                  90                  95

Gly Gly Gly Thr Lys Leu Thr Val Leu
            100                 105
```

<210> SEQ ID NO 64
<211> LENGTH: 315
<212> TYPE: DNA
<213> ORGANISM: Homo sapiens

<400> SEQUENCE: 64

```
tcctatgagc tgactcagcc actctcagtg tcagtggccc tgggacagac ggccaggatt        60
acctgtgggg gagacaacat tggaaataaa gatgtgcact ggtaccagca gaagccaggc       120
caggcccctg tgctggtcat ctatagggat agcaaccggc cctctgggat ccctgaggga       180
ttctctggct ccaactcggg gaacacggcc accctgacca tcagcagagc caagccgggg       240
gatgaggctg actattactg tcaggtgtgg gacagcattt gggtgttcgg cggagggacc       300
aagctgaccg tccta                                                        315
```

<210> SEQ ID NO 65
<211> LENGTH: 10
<212> TYPE: PRT
<213> ORGANISM: Artificial Sequence
<220> FEATURE:
<223> OTHER INFORMATION: Synthesis

<400> SEQUENCE: 65

```
Ser Ser Tyr Thr Ser Ile Ser Thr Trp Val
 1               5                  10
```

<210> SEQ ID NO 66
<211> LENGTH: 30
<212> TYPE: DNA
<213> ORGANISM: Artificial Sequence
<220> FEATURE:
<223> OTHER INFORMATION: Synthesis

<400> SEQUENCE: 66

```
agctcatata caagcatcag cacttgggtg                                         30
```

<210> SEQ ID NO 67
<211> LENGTH: 110
<212> TYPE: PRT
<213> ORGANISM: Artificial Sequence
<220> FEATURE:
<223> OTHER INFORMATION: Synthesis

<400> SEQUENCE: 67

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Phe Tyr
                20                  25                  30

Asn Tyr Val Ser Trp Tyr Gln Gln His Pro Gly Lys Ala Pro Glu Leu
                35                  40                  45

Met Ile Tyr Asp Val Ser Asn Arg Pro Ser Gly Val Ser Asp Arg Phe
            50                  55                  60

Ser Gly Ser Lys Ser Gly Asn Thr Ala Ser Leu Thr Ile Ser Gly Leu
```

```
                65                  70                  75                  80
Gln Ala Glu Asp Glu Ala Asp Tyr Tyr Cys Ser Ser Tyr Thr Ser Ile
                    85                  90                  95

Ser Thr Trp Val Phe Gly Gly Gly Thr Lys Leu Thr Val Leu
                100                 105                 110

<210> SEQ ID NO 68
<211> LENGTH: 330
<212> TYPE: DNA
<213> ORGANISM: Artificial Sequence
<220> FEATURE:
<223> OTHER INFORMATION: Synthesis

<400> SEQUENCE: 68
cagtctgccc tgactcagcc tgcctccgtg tctgggtctc ctggacagtc gatcaccatc      60
tcctgcactg gaaccagcag tgacgttggt ttttataact atgtctcctg gtaccaacag     120
cacccaggca agcccccga actcatgatt tatgatgtca gtaatcggcc ctcagggtt       180 tctgatcgct tctctggctc caagtctggc aacacggcct ccctgaccat ctctgggctc     240
caggctgagg acgaggctga ttattactgc agctcatata caagcatcag cacttgggtg     300
ttcggcggag ggaccaagct gaccgtccta                                      330
```

ANTI-PD-1 ANTIBODIES

CROSS-REFERENCE TO RELATED APPLICATIONS

This application is a divisional of U.S. patent application Ser. No. 15/751,236, filed on Feb. 8, 2018, now U.S. Pat. No. 11,008,391, which is a national stage entry, filed under 35 U.S.C. § 371, of International Application No. PCT/CN2016/094624, filed Aug. 11, 2016, which claims the benefit of priority to International Application No. PCT/CN2016/071374, filed Jan. 19, 2016, and International Application No. PCT/CN2015/086594, filed Aug. 11, 2015, the contents of all of which are incorporated herein by reference in their entireties.

REFERENCE TO SEQUENCE LISTING

This application contains a Sequence Listing in computer readable form, which is incorporated herein by reference in its entirety and forms part of the disclosure.

FIELD OF THE INVENTION

The present disclosure generally relates to novel anti-PD-1 antibodies.

BACKGROUND

Increasing evidences from preclinical and clinical results have shown that targeting immune checkpoints is becoming the most promising approach to treat patients with cancers. Programmed cell death 1, one of immune-checkpoint proteins, play a major role in limiting the activity of T cells that provide a major immune resistance mechanism by which tumor cells escaped immune surveillance. The interaction of PD-1 expressed on activated T cells, and PD-L1 expressed on tumor cells negatively regulate immune response and damp anti-tumor immunity. Expression of PD-L1 on tumors is correlated with reduced survival in esophageal, pancreatic and other types of cancers, highlighting this pathway as a new promising target for tumor immunotherapy. Multiple agents targeting PD-1 pathway have been developed by pharmaceutical companies, such as Bristol-Myers Squibb (BMS), Merck, Roche and GlaxoSmithKline (GSK). Data from clinical trials demonstrated early evidence of durable clinical activity and an encouraging safety profile in patients with various tumor types. Nivolumab, a PD-1 drug developed by BMS, is being put at center stage of the next-generation field. Now in 6 late-stage studies, the treatment spurred tumor shrinkage in three of 5 cancer groups studied, including 18% of 72 lung cancer patients, close to a third of 98 melanoma patients and 27% of 33 patients with kidney cancer. Developed by Merck, lambrolizumab is a fully human monoclonal IgG4 antibody that acts against PD-1, which grabbed the FDA's new breakthrough designation after impressive IB data came through for skin cancer. The results from a phase IB study have shown an objective anti-tumor response in 51% of 85 cancer patients, and a complete response in 9% of patients. Roche's experimental MPDL3280A demonstrated an ability to shrink tumors in 29 of 140 (21%) advanced cancer patients with various tumor sizes.

However, the existing therapies may not be all satisfactory and therefore new anti-PD-1 antibodies are still needed.

BRIEF SUMMARY OF THE INVENTION

The present disclosure provides novel monoclonal anti-PD-1 antibodies (in particular fully human antibodies), polynucleotides encoding the same, and methods of using the same.

In one aspect, the present disclosure provides isolated monoclonal antibodies or antigen binding fragments thereof, which are capable of specifically binding to human PD-1 at a Kd value no more than $10^{-8}$ M (e.g. no more than $\leq 9\times10^{-9}$ M, $\leq 8\times10^{-9}$ M, $\leq 7\times10^{-9}$ M, $\leq 6\times10^{-9}$ M, $\leq 5\times10^{-9}$ M, $\leq 4\times10^{-9}$ M, $\leq 3\times10^{-9}$ M, $\leq 2\times10^{-9}$ M, or $\leq 10^{-9}$ M) as measured by plasmon resonance binding assay.

In certain embodiments, the antibodies or antigen binding fragments thereof bind to monkey PD-1 at an EC50 of no more than 100 nM or no more than 10 nM (e.g. no more than 50 nM, 40 nM, 30 nM, 20 nM, 10 nM, 9 nM, 8 nM, 7 nM, 6 nM, 5 nM, 4 nM, 3 nM, 2 nM, or 1 nM,). In certain embodiments, the antibodies and antigen-binding fragments thereof do not bind to mouse PD-1 but bind to monkey PD-1 with a binding affinity similar to that of human PD-1. In certain embodiments, the antibodies or antigen binding fragments thereof potently inhibit binding of human or monkey PD-1 to its ligand (e.g. PD-L1 or PD-L2), at an IC50 of no more than 100 nM (e.g. no more than 50 nM, 40 nM, 30 nM, 20 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM). In certain embodiments, the EC50 or IC50 is measured by fluorescence-activated cell sorting (FACS) analysis.

In certain embodiments, the antibodies or antigen binding fragments thereof have substantially reduced effector function. In certain embodiments, the antibodies or antigen binding fragments thereof do not mediate ADCC or CDC or both.

In certain embodiments, the antibodies or antigen binding fragments thereof provided herein comprise a heavy chain CDR sequences selected from the group consisting of: SEQ ID NOs: 1, 3, 5, 13, 15, 21, 23, 25, 33, 35 and 37.

In one aspect, the antibodies or an antigen binding fragments thereof provided herein comprise a light chain CDR sequences selected from the group consisting of: SEQ ID NOs: 7, 9, 11, 17, 19, 27, 29, 31, 39, 41, 43 and 65.

In certain embodiments, the antibodies or antigen binding fragments thereof provided herein comprise at least one, two, three, four, five or six CDRs selected from the group consisting of: SEQ ID NOs: 1, 3, 5, 7, 9, and 11; or selected from the group consisting of: SEQ ID NOs: 13, 15, 5, 7, 17 and 11; or selected from the group consisting of: SEQ ID NOs: 1, 15, 5, 7, 17 and 19; or selected from the group consisting of: SEQ ID NOs: 1, 15, 5, 7, 17, and 65; or selected from the group consisting of: SEQ ID NOs: 21, 23, 25, 27, 29 and 31; or selected from the group consisting of: SEQ ID NOs: 33, 35, 37, 39, 41 and 43.

In certain embodiments, the antibodies or antigen binding fragments thereof provided herein comprise a heavy chain variable region selected from the group consisting of:
  a) a heavy chain variable region comprising SEQ ID NO: 1, SEQ ID NO: 3, and/or SEQ ID NO: 5;
  b) a heavy chain variable region comprising SEQ ID NO: 13, SEQ ID NO: 15, and/or SEQ ID NO: 5;
  c) a heavy chain variable region comprising SEQ ID NO: 1, SEQ ID NO: 15, and/or SEQ ID NO: 5;
  d) a heavy chain variable region comprising SEQ ID NO: 21, SEQ ID NO: 23, and/or SEQ ID NO: 25; and
  e) a heavy chain variable region comprising SEQ ID NO: 33, SEQ ID NO: 35, and/or SEQ ID NO: 37.

In certain embodiments, the antibodies or antigen binding fragments thereof provided herein comprise a light chain variable region selected from the group consisting of:
a) a light chain variable region comprising SEQ ID NO: 7, SEQ ID NO: 9, and/or SEQ ID NO: 11;
b) a light chain variable region comprising SEQ ID NO: 7, SEQ ID NO: 17, and/or SEQ ID NO: 11;
c) a light chain variable region comprising SEQ ID NO: 7, SEQ ID NO: 17, and/or SEQ ID NO: 19;
d) a light chain variable region comprising SEQ ID NO: 27, SEQ ID NO: 29, and/or SEQ ID NO: 31;
e) a light chain variable region comprising SEQ ID NO: 39, SEQ ID NO: 41, and/or SEQ ID NO: 43; And
f) a light chain variable region comprising SEQ ID NO: 7, SEQ ID NO: 17, and/or SEQ ID NO: 65.

In certain embodiments, the antibodies or antigen binding fragments thereof provided herein comprise:
a) a heavy chain variable region comprising SEQ ID NO: 1, SEQ ID NO: 3, and/or SEQ ID NO: 5; and a light chain variable region comprising SEQ ID NO: 7, SEQ ID NO: 9, and/or SEQ ID NO: 11;
b) a heavy chain variable region comprising SEQ ID NO: 13, SEQ ID NO: 15, and/or SEQ ID NO: 5; and a light chain variable region comprising SEQ ID NO: 7, SEQ ID NO: 17, and/or SEQ ID NO: 11;
c) a heavy chain variable region comprising SEQ ID NO: 1, SEQ ID NO: 15, and/or SEQ ID NO: 5; and a light chain variable region comprising SEQ ID NO: 7, SEQ ID NO: 17, and/or SEQ ID NO: 19;
d) a heavy chain variable region comprising SEQ ID NO: 21, SEQ ID NO: 23, and/or SEQ ID NO: 25 and a light chain variable region comprising SEQ ID NO: 27, SEQ ID NO: 29, and/or SEQ ID NO: 31;
e) a heavy chain variable region comprising SEQ ID NO: 33, SEQ ID NO: 35, and/or SEQ ID NO: 37; and a light chain variable region comprising SEQ ID NO: 39, SEQ ID NO: 41, and/or SEQ ID NO: 43; or
f) a heavy chain variable region comprising SEQ ID NO: 1, SEQ ID NO: 15, and/or SEQ ID NO: 5; and a light chain variable region comprising SEQ ID NO: 7, SEQ ID NO: 17, and/or SEQ ID NO: 65.

In certain embodiments, the antibodies or antigen binding fragments thereof provided herein comprise a heavy chain variable region selected from the group consisting of: SEQ ID NO: 45, SEQ ID NO: 49, SEQ ID NO: 53, SEQ ID NO: 57 and SEQ ID NO: 61.

In certain embodiments, the antibodies or antigen binding fragments provided herein comprise a light chain variable region selected from the group consisting of: SEQ ID NO: 47, SEQ ID NO: 51, SEQ ID NO: 55, SEQ ID NO: 59, SEQ ID NO: 63 and SEQ ID NO: 67.

In certain embodiments, the antibodies or antigen binding fragments thereof provided herein comprise:
a) a heavy chain variable region comprising SEQ ID NO: 45; and a light chain variable region comprising SEQ ID NO: 47;
b) a heavy chain variable region comprising SEQ ID NO: 49; and a light chain variable region comprising SEQ ID NO: 51;
c) a heavy chain variable region comprising SEQ ID NO: 53; and a light chain variable region comprising SEQ ID NO: 55;
d) a heavy chain variable region comprising SEQ ID NO: 57; and a light chain variable region comprising SEQ ID NO: 59;
e) a heavy chain variable region comprising SEQ ID NO: 61; and a light chain variable region comprising SEQ ID NO: 63; or
f) a heavy chain variable region comprising SEQ ID NO: 53; and a light chain variable region comprising SEQ ID NO: 67.

In certain embodiments, the antibodies provided herein include, for example, 1.7.3 hAb, 1.49.9 hAb, 1.103.11 hAb, 1.103.11-v2 hAb, 1.139.15 hAb, and 1.153.7 hAb.

In certain embodiments, the antibodies or antigen binding fragments thereof provided herein compete for the same epitope with antibodies 1.7.3 hAb, 1.49.9 hAb, 1.103.11 hAb, 1.103.11-v2 hAb, 1.139.15 hAb, or 1.153.7 hAb. In certain embodiments, the antibodies or antigen binding fragments thereof provided herein bind to the epitope comprising at least one of the following amino acid residues of PD-1:V64, P83, D85, L128, A129, P130, K131, A132 and Q133.

In certain embodiments, the antibodies or antigen binding fragments thereof are capable of blocking binding of human PD-1 to its ligand and thereby providing at least one of the following activities:
a) inducing production of IL-2 in CD4+T cells;
b) inducing production of IFNγ in CD4+T cells;
c) inducing proliferation of CD4+T cells and
d) reversing T reg's suppressive function.

In certain embodiments, the antibodies provided herein are a monoclonal antibody, fully human antibody, humanized antibody, chimeric antibody, recombinant antibody, bispecific antibody, labeled antibody, bivalent antibody, or anti-idiotypic antibody. In certain embodiments, the antibodies or antigen binding fragments thereof are fully human monoclonal antibodies, optionally produced by a transgenic rat, for example, a transgenic rat having inactivated endogenous expression of rat immunoglobulin genes and carrying recombinant human immunoglobulin loci having J-locu deletion and a C-kappa mutation.

In certain embodiments, the antigen-binding fragments thereof provided herein are a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In certain embodiments, the antibodies or antigen-binding fragments thereof provided herein further comprise an immunoglobulin constant region.

In certain embodiments, the antibodies or antigen-binding fragments thereof provided herein, further comprise a conjugate.

In certain embodiments, the conjugate can be a detectable label, a pharmacokinetic modifying moiety, or a purification moiety.

In another aspect, the present disclosure provides isolated polynucleotides encoding the antibodies or antigen binding fragments thereof provided herein. In certain embodiments, polynucleotides are provided that encode the amino acid sequences of the antibodies or antigen-binding fragments disclosed herein. In certain other embodiments, vectors are provided that comprise these polynucleotides, and in certain other embodiments, host cells are provided that comprise these vectors. In certain embodiments, methods are provided for expressing one or more of the antibodies or antigen-binding fragments disclosed herein by culturing these host cells under conditions in which the antibodies or antigen-binding fragments encoded by the polynucleotides are expressed from a vector. In certain embodiments, the polynucleotides provided herein are operably associated with a promoter such as a SV40 promoter in a vector. In certain embodiments, host cells comprising the vectors provided herein are Chinese hamster ovary cell, or 293F cell.

In another aspect, the present disclosure provides kits comprising the antibody or antigen-binding fragment thereof.

In another aspect, the PD-1 antibodies provided herein, such as the 1.7.3 hAb, 1.49.9 hAb, 1.103.11 hAb, 1.103.11-v2 hAb, 1.139.15 hAb, and 1.153.7 hAb have good tolerability and high in vivo anti-tumor activity in an animal. In certain embodiments, an animal having tumor cells administered with the PD-1 antibodies provided herein has a reduction of the tumor volume by at least 20%, at least 30%, at least 40%, at least 50%, at least 60%, at least 70%, at least 80%, at least 90%, or at least 95% as compared to the control animal having similar baseline tumor volume but administered only with vehicle.

In another aspect, the present disclosure provides methods of treating a condition associated with PD-1 in an individual, comprising: administering to the individual a therapeutically effective amount of antibody or antigen-binding fragment thereof provided herein. In certain embodiments, the individual has been identified as having a disorder or a condition likely to respond to a PD-1 antagonist. In certain embodiments, the individual has been identified as positive for presence or upregulated level of the PD-L1 in a test biological sample from the individual.

In another aspect, the present disclosure provides pharmaceutical compositions comprising the antibody or antigen-binding fragment thereof provided herein and one or more pharmaceutically acceptable carriers. In certain of these embodiments, the pharmaceutical carriers may be, for example, diluents, antioxidants, adjuvants, excipients, or non-toxic auxiliary substances.

In another aspect, the present disclosure provides methods of treating a condition in a subject that would benefit from upregulation of immune response, comprising administering an effective amount of the antibody or antigen-binding fragment thereof provided herein to the subject. In certain embodiments, the subject has upregulated expression of PD-L1, or has been identified as positive for expression of PD-L1.

Use of the antibody or antigen-binding fragment thereof provided herein in the manufacture of a medicament for treating a condition that would benefit from upregulation of immune response. In certain embodiments, the condition is cancer or chronic viral infection.

DETAILED DESCRIPTION OF THE INVENTION

Figure 1:
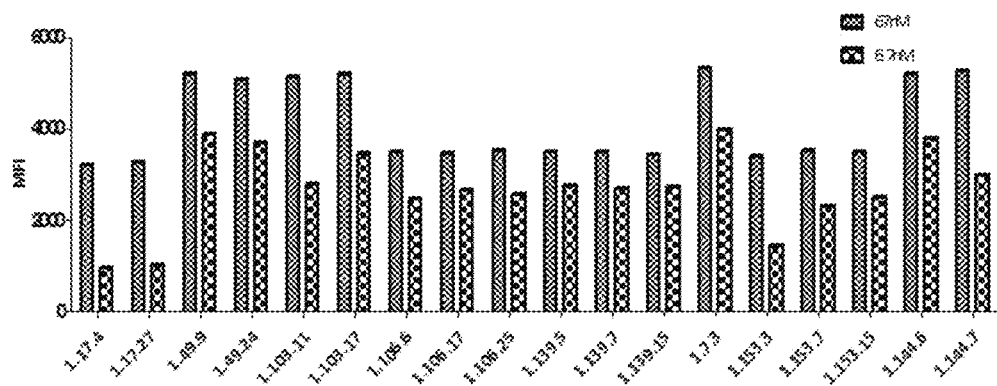
FIG. 1 presents the binding of fully human anti-PD-1 antibodies to PD-1 expressing CHO cell as measured by FACS analysis.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

Definitions

The term "antibody" as used herein includes any immunoglobulin, monoclonal antibody, polyclonal antibody, multispecific antibody, or bispecific (bivalent) antibody that binds to a specific antigen. A native intact antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ, and mammalian light chains are classified as λ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani, B., Chothia, C., Lesk, A. M., J. Mol. Biol., 273(4), 927 (1997); Chothia, C. et al., J Mol Biol. December 5; 186(3):651-63 (1985); Chothia, C. and Lesk, A. M., J. Mol. Biol., 196,901 (1987); Chothia, C. et al., Nature. December 21-28; 342(6252):877-83 (1989); Kabat E. A. et al., National Institutes of Health, Bethesda, Md. (1991)). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab)2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a camelized single domain antibody, a nanobody, a domain antibody, and a bivalent domain antibody. An antigen-binding fragment is capable of binding to the same antigen to which the parent antibody binds. In certain embodiments, an antigen-binding fragment may comprise one or more CDRs from a particular human antibody grafted to a framework region from one or more different human antibodies.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab'.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Huston J S et al. Proc Natl Acad Sci USA, 85:5879 (1988)).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann L. and Muyldermans S., J Immunol Methods. December 10; 231(1-2): 25-38 (1999); Muyldermans S., J Biotechnol. June; 74(4): 277-302 (2001); WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman C. et al., Nature. June 3; 363(6428):446-8 (1993); Nguyen V K. et al. "Heavy-chain antibodies in Camelidae; a case of evolutionary innovation," Immunogenetics. April; 54(1):39-47 (2002); Nguyen V K. et al. Immunology. May; 109(1): 93-101 (2003)). The variable domain of a heavy chain antibody (VHH domain) represents the smallest known antigen-binding unit generated by adaptive immune responses (Koch-Nolte F. et al., FASEB J. November; 21(13):3490-8. Epub 2007 Jun. 15 (2007)).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_L$-$V_H$) (see, e.g., Holliger P. et al., Proc Natl Acad Sci USA. July 15; 90(14):6444-8 (1993); EP404097; WO93/11161). By using a linker that is too short to allow pairing between the two domains on the same chain, the domains are forced to pair with the complementary domains of another chain, thereby creating two antigen-binding sites. The antigen-binding sites may target the same of different antigens (or epitopes).

A "domain antibody" refers to an antibody fragment containing only the variable region of a heavy chain or the variable region of a light chain. In certain instances, two or more $V_H$ domains are covalently joined with a peptide linker to create a bivalent or multivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes). In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "fully human" as used herein, with reference to antibody or antigen-binding fragment, means that the antibody or the antigen-binding fragment has or consists of amino acid sequence(s) corresponding to that of an antibody produced by a human or a human immune cell, or derived from a non-human source such as a transgenic non-human animal that utilizes human antibody repertoires or other human antibody-encoding sequences. In certain embodiments, a fully human antibody does not comprise amino acid residues (in particular antigen-binding residues) derived from a non-human antibody.

The term "humanized" as used herein, with reference to antibody or antigen-binding fragment, means that the antibody or the antigen-binding fragment comprises CDRs derived from non-human animals, FR regions derived from human, and when applicable, the constant regions derived from human. A humanized antibody or antigen-binding fragment is useful as human therapeutics in certain embodiments because it has reduced immunogenicity in human. In some embodiments, the non-human animal is a mammal, for example, a mouse, a rat, a rabbit, a goat, a sheep, a guinea pig, or a hamster. In some embodiments, the humanized antibody or antigen-binding fragment is composed of substantially all human sequences except for the CDR sequences which are non-human. In some embodiments, the FR regions derived from human may comprise the same amino acid sequence as the human antibody from which it is derived, or it may comprise some amino acid changes, for example, no more than 10, 9, 8, 7, 6, 5, 4, 3, 2, or 1 changes of amino acid. In some embodiments, such change in amino acid could be present in heavy chain FR regions only, in light chain FR regions only, or in both chains. In some preferable embodiments, the humanized antibodies comprise human FR1-3 and human JH and Jκ.

The term "chimeric" as used herein, means an antibody or antigen-binding fragment, having a portion of heavy and/or light chain derived from one species, and the rest of the heavy and/or light chain derived from a different species. In an illustrative example, a chimeric antibody may comprise a constant region derived from human and a variable region from a non-human species, such as from mouse.

"PD-1" as used herein refers programmed cell death protein, which belongs to the superfamily of immunoglobulin and functions as coinhibitory receptor to negatively regulate the immune system. PD-1 is a member of the CD28/CTLA-4 family, and has two known ligands including PD-L1 and PD-L2. Representative amino acid sequence of human PD-1 is disclosed under the NCBI accession number: NP_005009.2, and the representative nucleic acid sequence encoding the human PD-1 is shown under the NCBI accession number: NM_005018.2.

"PD-L1" as used herein refers to programmed cell death ligand 1 (PD-L1, see, for example, Freeman et al. (2000) *J. Exp. Med.* 192:1027). Representative amino acid sequence of human PD-L1 is disclosed under the NCBI accession number: NP_054862.1, and the representative nucleic acid sequence encoding the human PD-L1 is shown under the NCBI accession number: NM_014143.3. PD-L1 is expressed in placenta, spleen, lymph nodes, thymus, heart, fetal liver, and is also found on many tumor or cancer cells. PD-L1 binds to its receptor PD-1 or B7-1, which is expressed on activated T cells, B cells and myeloid cells. The binding of PD-L1 and its receptor induces signal transduction to suppress TCR-mediated activation of cytokine production and T cell proliferation. Accordingly, PD-L1 plays a major role in suppressing immune system during particular events such as pregnancy, autoimmune diseases, tissue allografts, and is believed to allow tumor or cancer cells to circumvent the immunological checkpoint and evade the immune response.

"Anti-PD-1 antibody" as used herein refers to an antibody that is capable of specific binding to PD-1 (e.g. human or monkey PD-1) with an affinity which is sufficient to provide for diagnostic and/or therapeutic use.

The term "specific binding" or "specifically binds" as used herein refers to a non-random binding reaction between two molecules, such as for example between an antibody and an antigen. In certain embodiments, the antibodies or antigen-binding fragments provided herein specifically bind human and/or monkey PD-1 with a binding affinity ($K_D$) of $\leq 10^{-6}$ M (e.g., $\leq 5 \times 10^{-7}$ M, $\leq 2 \times 10^{-7}$M, $\leq 10^{-7}$ M, $\leq 5 \times 10^{-8}$ M, $\leq 2 \times 10^{-8}$ M, $\leq 10^{-8}$ M, $\leq 5 \times 10^{-9}$M, $\leq 2 \times 10^{-9}$M, $\leq 10^{-9}$ M, $10^{-10}$ M). $K_D$ as used herein refers to the ratio of the dissociation rate to the association rate ($k_{off}/k_{on}$), may be determined using surface plasmon resonance methods for example using instrument such as Biacore.

The ability to "block binding" or "compete for the same epitope" as used herein refers to the ability of an antibody or antigen-binding fragment to inhibit the binding interaction between two molecules (e.g. human PD-1 and an anti-PD-1 antibody) to any detectable degree. In certain embodiments, an antibody or antigen-binding fragment that blocks binding between two molecules inhibits the binding interaction between the two molecules by at least 50%. In certain embodiments, this inhibition may be greater than 60%, greater than 70%, greater than 80%, or greater than 90%.

The term "epitope" as used herein refers to the specific group of atoms or amino acids on an antigen to which an antibody binds. Two antibodies may bind the same epitope within an antigen if they exhibit competitive binding for the antigen. For example, if an antibody or antigen-binding fragment as disclosed herein blocks binding of the exemplary antibodies such as 1.7.3 hAb, 1.49.9 hAb, 1.103.11 hAb, 1.103.11-v2 hAb, 1.139.15 hAb, and 1.153.7 hAb to human PD-1, then the antibody or antigen-binding fragment may be considered to bind the same epitope as those exemplary antibodies.

A particular amino acid residue within the epitope can be mutated, e.g. by alanine scanning mutagenesis, and mutations that reduce or prevent protein binding are identified. An "alanine scanning mutagenesis" is a method that can be performed for identifying certain residues or regions of a protein that affect the interaction of the epitope with another compound or protein that binds to it. A residue or group of target residues within the protein is replaced by a neutral or negatively charged amino acid (most preferably alanine or polyalanine, or a conservative amino acid substitution). Any mutation of the amino acid residues or codons encoding the same that reduces binding of the protein more than a threshold or reduces binding of the protein to the maximal degree than other mutations is likely to be within the epitope bound by the protein. In certain embodiments of the present disclosure, the epitope that is critical for the PD-1 antibody comprises at least one of the amino acid residues of V64, P83, D85, L128, A129, P130, K131, A132 and Q133.

"1.7.3 hAb" as used herein refers to a fully human monoclonal antibody having a heavy chain variable region of SEQ ID NO: 45, light chain variable region of SEQ ID NO: 47, and a human constant region of IgG4 isotype.

"1.49.9 hAb" as used herein refers to a fully human monoclonal antibody having a heavy chain variable region of SEQ ID NO: 49, light chain variable region of SEQ ID NO: 51, and a human constant region of IgG4 isotype.

"1.103.11 hAb" as used herein refers to a fully human monoclonal antibody having a heavy chain variable region of SEQ ID NO: 53, light chain variable region of SEQ ID NO: 55, and a human constant region of IgG4 isotype.

"1.103.11-v2 hAb" as used herein refers to a fully human monoclonal antibody having a heavy chain variable region of SEQ ID NO: 53, light chain variable region of SEQ ID NO: 67, and a human constant region of IgG4 isotype.

"1.139.15 hAb" as used herein refers to a fully human monoclonal antibody having a heavy chain variable region of SEQ ID NO: 57, light chain variable region of SEQ ID NO: 59, and a human constant region of IgG4 isotype.

"1.153.7 hAb" as used herein refers to a fully human monoclonal antibody having a heavy chain variable region of SEQ ID NO: 61, light chain variable region of SEQ ID NO: 63, and a human constant region of IgG4 isotype.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gln), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

"Percent (%) sequence identity" with respect to amino acid sequence (or nucleic acid sequence) is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). Conservative substitution of the amino acid residues may or may not be considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

"T cell" as used herein includes CD4$^+$ T cells, CD8$^+$ T cells, T helper 1 type T cells, T helper 2 type T cells, T helper 17 type T cells and inhibitory T cells.

"Effector functions" as used herein refer to biological activities attributable to the binding of Fc region of an antibody to its effectors such as C1 complex and Fc receptor. Exemplary effector functions include: complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

"Cancer" or "cancerous condition" as used herein refers to any medical condition mediated by neoplastic or malignant cell growth, proliferation, or metastasis, and includes both solid cancers and non-solid cancers such as leukemia. "Tumor" as used herein refers to a solid mass of neoplastic and/or malignant cells.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" may refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" includes eradicating all or part of a tumor, inhibiting or slowing tumor growth and metastasis, preventing or delaying the development of a tumor, or some combination thereof.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state. In certain embodiments, the antibodies and antigen-binding fragments have a purity of at least 90%, 93%, 95%, 96%, 97%, 98%, 99% as determined by electrophoretic methods (such as SDS-PAGE, isoelectric focusing, capillary electrophoresis), or chromatographic methods (such as ion exchange chromatography or reverse phase HPLC).

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which an exogenous polynucleotide and/or a vector has been introduced.

A "disease associated with or related to PD-1" as used herein refers to any condition that is caused by, exacerbated by, or otherwise linked to increased or decreased expression or activities of PD-1 (e.g. a human PD-1).

The term "therapeutically effective amount" or "effective dosage" as used herein refers to the dosage or concentration of a drug effective to treat a disease or condition associated with human PD-1. For example, with regard to the use of the antibodies or antigen-binding fragments disclosed herein to treat cancer, a therapeutically effective amount is the dosage or concentration of the antibody or antigen-binding fragment capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

Anti-PD-1 Antibody

In one aspect, the present disclosure provides anti-PD-1 antibodies and the antigen-binding fragments thereof. PD-1, also called as CD279, is known as a key immune-checkpoint receptor expressed by activated T cells, which mediates immunosuppression. PD-1 ligand 1 (PD-L1) is a 40 kDa transmembrane protein expressed on various tumor cells, stromal cells or both, and binds to PD-1. Inhibition of the interaction between PD-1 and PD-L1 can enhance T-cell responses and thus mediates anti-cancer activity.

In certain embodiments, the present disclosure provides exemplary fully human monoclonal antibodies 1.7.3 hAb, 1.49.9 hAb, 1.103.11 hAb, 1.103.11-v2 hAb, 1.139.15 hAb, and 1.153.7 hAb, whose CDR sequences are shown in the below Table 1, and heavy or light chain variable region sequences are also shown below.

TABLE 1

| | | CDR1 | CDR2 | CDR3 |
|---|---|---|---|---|
| 1.7.3 hAb-<br>VH(23466-<br>VH) | | SEQ ID NO: 1<br>STTYYWV<br>SEQ ID NO: 2<br>AGT ACT ACT TAC<br>TAC TGG GTC | SEQ ID NO: 3<br>SISYSGNTYYNPSLKS<br>SEQ ID NO: 4<br>AGT ATC TCT TAT AGT<br>GGG AAC ACC TAC<br>TAC AAT CCG TCC CTC<br>AAG AGT | SEQ ID NO: 5<br>HLGYNGRYLPFDY<br>SEQ ID NO: 6<br>CAT CTA GGG TAT<br>AAT GGG AGG TAC<br>CTC CCC TTT GAC<br>TAC |
| 1.7.3 hAb -<br>VL(23195-<br>VL) | | SEQ ID NO: 7<br>TGTSSDVGFYNYVS<br>SEQ ID NO: 8<br>ACT GGA ACC AGC<br>AGT GAC GTT GGT<br>TTT TAT AAC TAT<br>GTC TCC | SEQ ID NO: 9<br>DVTNRPS<br>SEQ ID NO: 10<br>GAT GTC ACT AAT<br>CGG CCC TCA | SEQ ID NO: 11<br>SSYTSISTWV<br>SEQ ID NO: 12<br>AGC TCA TAT ACA<br>AGC ATC AGC ACT<br>TGG GTG |
| 1.49.9 hAb -<br>VH(20951-<br>VH) | | SEQ ID NO: 13<br>SSTYYWG<br>SEQ ID NO: 14<br>AGT AGT ACT TAC<br>TAC TGG GGC | SEQ ID NO: 15<br>SISYSGSTYYNPSLKS<br>SEQ ID NO: 16<br>AGT ATC TCT TAT AGT<br>GGG AGC ACC TAC<br>TAC AAT CCG TCC CTC<br>AAG AGT | SEQ ID NO: 5<br>HLGYNGRYLPFDY<br>SEQ ID NO: 6<br>CAT CTA GGG TAT<br>AAT GGG AGG TAC<br>CTC CCC TTT GAC<br>TAC |
| 1.49.9 hAb -<br>VH(20951-<br>VL) | | SEQ ID NO: 7<br>TGTSSDVGFYNYVS<br>SEQ ID NO: 8<br>ACT GGA ACC AGC<br>AGT GAC GTT GGT<br>TTT TAT AAC TAT<br>GTC TCC | SEQ ID NO: 17<br>DVSNRPS<br>SEQ ID NO: 18<br>GAT GTC AGT AAT<br>CGG CCC TCA | SEQ ID NO 11<br>SSYTSISTWV<br>SEQ ID NO: 12<br>AGC TCA TAT ACA<br>AGC ATC AGC ACT<br>TGG GTG |
| 1.103.11<br>hAb -<br>VH(20975-<br>VH) | | SEQ ID NO: 1<br>STTYYWV<br>SEQ ID NO: 2<br>AGT ACT ACT TAC<br>TAC TGG GTC | SEQ ID NO: 15<br>SISYSGSTYYNPSLKS<br>SEQ ID NO: 16<br>AGT ATC TCT TAT AGT<br>GGG AGC ACC TAC<br>TAC AAT CCG TCC CTC<br>AAG AGT | SEQ ID NO: 5<br>HLGYNGRYLPFDY<br>SEQ ID NO: 6<br>CAT CTA GGG TAT<br>AAT GGG AGG TAC<br>CTC CCC TTT GAC<br>TAC |
| 1.103.11<br>hAb -<br>VH(20975-<br>VL) | | SEQ ID NO: 7<br>TGTSSDVGFYNYVS<br>SEQ ID NO: 8<br>ACT GGA ACC AGC<br>AGT GAC GTT GGT<br>TTT TAT AAC TAT<br>GTC TCC | SEQ ID NO: 17<br>DVSNRPS<br>SEQ ID NO: 18<br>GAT GTC AGT AAT<br>CGG CCC TCA | SEQ ID NO: 19<br>SSYTNISTWV<br>SEQ ID NO: 20<br>AGC TCA TAT ACA<br>AAC ATC AGC ACT<br>TGG GTG |

TABLE 1-continued

| | CDR1 | CDR2 | CDR3 |
|---|---|---|---|
| 1.139.15 hAb - VH(23521-VH) | SEQ ID NO: 21 STTYYWG SEQ ID NO: 22 AGT ACT ACT TAC TAC TGG GGC | SEQ ID NO: 23 SISYSGTTYYNPSLKS SEQ ID NO: 24 AGT ATC TCT TAT AGT GGG ACC ACC TAC TAC AAC CCG TCC CTC AAG AGT | SEQ ID NO: 25 HLGYNSNVVYPFDY SEQ ID NO: 26 CAT CTC GGG TAT AAC AGC AAC TGG TAC CCT TTT GAC TAC |
| 1.139.15 hAb - VH(23521-VL) | SEQ ID NO: 27 TGTSSDVGSYNRVS SEQ ID NO: 28 ACT GGA ACC AGC AGT GAC GTT GGT AGT TAT AAC CGT GTC TCC | SEQ ID NO: 29 EVSNRPS SEQ ID NO: 30 GAG GTC AGT AAT CGG CCC TCA | SEQ ID NO: 31 SSYTSSSTWV SEQ ID NO: 32 AGC TCA TAT ACA AGC AGC AGC ACT TGG GTG |
| 1.153.7 hAb - VH(20942-VH) | SEQ ID NO: 33 SHAMS SEQ ID NO: 34 AGC CAT GCC ATG AGC | SEQ ID NO: 35 TITGGGGSIYYADSVKG SEQ ID NO: 36 ACT ATT ACT GGT GGT GGT GGT AGC ATA TAC TAC GCA GAC TCC GTG AAG GGC | SEQ ID NO: 37 NRAGEGYFDY SEQ ID NO: 38 AAC CGC GCT GGG GAG GGT TAC TTT GAC TAC |
| 1.153.7 hAb - VH(20942-VL) | SEQ ID NO: 39 GGDNIGNKDVH SEQ ID NO: 40 GGG GGA GAC AAC ATT GGA AAT AAA GAT GTG CAC | SEQ ID NO: 41 RDSNRPS SEQ ID NO: 42 AGG GAT AGC AAC CGG CCC TCT | SEQ ID NO: 43 QVWDSIWV SEQ ID NO: 44 CAG GTG TGG GAC AGC ATT TGG GTG |
| 1.103.11-v2 hAb - VH(20975-VH) | SEQ ID NO: 1 STTYYWV SEQ ID NO: 2 AGT ACT ACT TAC TAC TGG GTC | SEQ ID NO: 15 SISYSGSTYYNPSLKS SEQ ID NO: 16 AGT ATC TCT TAT AGT GGG AGC ACC TAC TAC AAT CCG TCC CTC AAG AGT | SEQ ID NO: 5 HLGYNGRYLPFDY SEQ ID NO: 6 CAT CTA GGG TAT AAT GGG AGG TAC CTC CCC TTT GAC TAC |
| 1.103.11-v2 hAb - VH(20975-2-VL) | SEQ ID NO: 7 TGTSSDVGFYNYVS SEQ ID NO: 8 ACT GGA ACC AGC AGT GAC GTT GGT TTT TAT AAC TAT GTC TCC | SEQ ID NO: 17 DVSNRPS SEQ ID NO: 18 GAT GTC AGT AAT CGG CCC TCA | SEQ ID NO: 65 SSYTSISTWV SEQ ID NO: 66 AGC TCA TAT ACA AGC ATC AGC ACT TGG GTG |

1.7.3 hAb-VH(23466-VH): (SEQ ID NO:45 for amino acid and SEQ ID NO:46 for nucleic acid) with heavy chain CDRs1-3: SEQ ID NOs: 1, 3, 5 are amino acid sequences and SEQ ID NO:2, 4, 6 are nucleic acid sequences, respectively:

V segment: IGHV4-39*01
D segment: IGHD1-26*01
J segment: IGHJ4*02

```
     Q   L   Q   L   Q   E   S   G   P   G   L   V   K   P   S
 1  CAG CTG CAG CTG CAG GAG TCG GGC CCA GGA CTG GTG AAG CCT TCG
     E   T   L   T   L   T   C   T   V   S   G   D   S   I   S
46  GAG ACC CTG ACC CTC ACC TGC ACT GTC TCT GGT GAC TCC ATC AGC
                       CDR1
                ~~~~~~~~~~~~~~~~~~~~~
     S   T   T   Y   Y   W   V   W   I   R   Q   P   P   G   K
91  AGT ACT ACT TAC TAC TGG GTC TGG ATC CGC CAG CCC CCA GGG AAG
```

```
                                          CDR2
                               ~~~~~~~~~~~~~~~~~~~~~~~~~~~~
         G   L   E   W   I   G   S   I   S   Y   S   G   N   T   Y
     136 GGA CTG GAG TGG ATT GGG AGT ATC TCT TAT AGT GGG AAC ACC TAC

CDR2
          ~~~~~~~~~~~~~~~~~~~~~~
         Y   N   P   S   L   K   S   R   V   T   I   S   V   D   T
     181 TAC AAT CCG TCC CTC AAG AGT CGA GTC ACC ATA TCC GTA GAC ACG

S   K   N   H   F   S   L   K   L   S   S   V   A   A   T
     226 TCC AAG AAC CAC TTC TCC CTG AAG CTG AGT TCT GTG GCC GCC ACA
                                                          CDR3
                                                 ~~~~~~~~~~~~~~~~~~~~~~~~~~
         D   T   A   L   Y   Y   C   A   R   H   L   G   Y   N   G
     271 GAC ACG GCT CTA TAT TAC TGT GCG AGA CAT CTA GGG TAT AAT GGG

CDR3
            ~~~~~~~~~~~~~~~~~~~~~~~~~~~~~~
         R   Y   L   P   F   D   Y   W   G   Q   G   T   L   V   T
     316 AGG TAC CTC CCC TTT GAC TAC TGG GGC CAG GGA ACC CTG GTC ACC
         V   S   S   (SEQ ID NO: 45)
     361 GTC TCC TCC   (SEQ ID NO: 46)
```

1.7.3 hAb-VL(23195-VL): (SEQ ID NO:47 for amino acid and SEQ ID NO:48 for nucleic acid) with light chain CDRs1-3: SEQ ID NOs: 7, 9, 11 are amino acid sequences and SEQ ID NO:8, 10, 12 are nucleic acid sequences, respectively:
V segment: IGLV2-14*01
J segment: IGLJ3*02

```
         Q   S   A   L   T   Q   P   A   S   V   S   G   S   P   G
       1 CAG TCT GCC CTG ACT CAG CCT GCC TCC GTG TCT GGG TCT CCT GGA
                                                   CDR1
                                      ~~~~~~~~~~~~~~~~~~~~~~~~~~~~
         Q   S   I   T   I   S   C   T   G   T   S   S   D   V   G
      46 CAG TCG ATC ACC ATC TCC TGC ACT GGA ACC AGC AGT GAC GTT GGT

CDR1
         ~~~~~~~~~~~~~~~~~~~~~~~
         F   Y   N   Y   V   S   W   Y   Q   Q   H   P   G   K   A
      91 TTT TAT AAC TAT GTC TCC TGG TAC CAA CAG CAC CCA GGC AAA GCC

CDR2
                               ~~~~~~~~~~~~~~~~~~~~~~~~~~~~
         P   E   L   M   I   Y   D   V   T   N   R   P   S   G   V
     136 CCC GAA CTC ATG ATT TAT GAT GTC ACT AAT CGG CCC TCA GGG GTT

S   D   R   F   S   G   S   K   S   G   N   T   A   S   L
     181 TCT GAT CGC TTC TCT GGC TCC AAG TCT GGC AAC ACG GCC TCC CTG
         T   I   S   G   L   Q   A   E   D   E   A   D   Y   Y   C
     226 ACC ATC TCT GGG CTC CAG GCT GAG GAC GAG GCT GAT TAT TAC TGC
                           CDR3
            ~~~~~~~~~~~~~~~~~~~~~~~~~~~~~~~~~~~
         S   S   Y   T   S   I   S   T   W   V   F   G   G   G   T
     261 AGC TCA TAT ACA AGC ATC AGC ACT TGG GTG TTC GGC GGA GGG ACC
         K   L   T   V   L   (SEQ ID NO: 47)
     316 AAG CTG ACC GTC CTA   (SEQ ID NO: 48)
```

1.49.9 hAb-VH(20951-VH): (SEQ ID NO:49 for amino acid and SEQ ID NO:50 for nucleic acid) with heavy chain CDRs 1-3: SEQ ID NOs: 13, 15, 5 are amino acid sequences and SEQ ID NO:14, 16, 6 are nucleic acid sequences, respectively:
  V segment: IGHV4-39*01
  D segment: IGHD1-26*01
  J segment: IGHJ4*02

```
      Q   L   Q   L   Q   E   S   G   P   G   L   V   K   P   S
  1   CAG CTG CAG CTG CAG GAG TCG GGC CCA GGA CTG GTG AAG CCT TCG

E   T   L   S   L   T   C   T   V   S   G   G   S   I   S
 46   GAG ACC CTG TCC CTC ACC TGC ACT GTC TCT GGT GGC TCC ATC AGC

CDR1
                ~~~~~~~~~~~~~~~~~~~~~~
      S   S   T   Y   Y   W   G   W   I   R   Q   P   P   G   K
 91   AGT AGT ACT TAC TAC TGG GGC TGG ATC CGC CAG CCC CCA GGG AAG

CDR2
                                      ~~~~~~~~~~~~~~~~~~~~~~~~~~~~~~~
      G   L   E   W   I   G   S   I   S   Y   S   G   S   T   Y
136   GGA CTG GAG TGG ATT GGG AGT ATC TCT TAT AGT GGG AGC ACC TAC

CDR2
          ~~~~~~~~~~~~~~~~~~~~~~
      Y   N   P   S   L   K   S   R   V   T   I   S   V   D   T
181   TAC AAT CCG TCC CTC AAG AGT CGA GTC ACC ATA TCC GTA GAC ACG

S   K   N   Q   F   S   L   K   L   S   S   V   T   D   A
226   TCC AAG AAC CAG TTC TCC CTG AAG CTG AGC TCT GTG ACC GAC GCA

CDR3
                                                  ~~~~~~~~~~~~~~~~~~~~
      D   T   A   V   Y   Y   C   A   R   H   L   G   Y   N   G
261   GAC ACG GCT GTG TAT TAC TGT GCG AGA CAT CTA GGG TAT AAT GGG

CDR3
          ~~~~~~~~~~~~~~~~~~~~~~
      R   Y   L   P   F   D   Y   W   G   Q   G   T   L   V   T
316   ACG TAC CTC CCC TTT GAC TAC TGG GGC CAG GGA ACC CTG GTC ACC
      V   S   S   (SEQ ID NO: 49)
361   GTC TCC TCC   (SEQ ID NO: 50)
```

1.49.9 hAb-VL(21526-VL): (SEQ ID NO:51 for amino acid and SEQ ID NO:52 for nucleic acid) with light chain CDRs 1-3: SEQ ID NOs: 7, 17, 11 are amino acid sequences and SEQ ID NO:8, 18, 12 are nucleic acid sequences, respectively:
  V segment: IGLV2-14*01
  J segment: IGLJ3*02

```
      Q   S   A   L   T   Q   P   A   S   V   S   G   S   P   G
  1   CAG TCT GCC CTG ACT CAG CCT GCC TCC GTG TCT GGG TCT CCT GGA
                                              CDR1
                                      ~~~~~~~~~~~~~~~~~~~~~~~~~~~~~~~
      Q   S   I   T   I   S   C   T   G   T   S   S   D   V   G
 46   CAG TCG ATC ACC ATC TCC TGC ACT GGA ACC AGC AGT GAC GTT GGT

CDR1
      ~~~~~~~~~~~~~~~~~~~~
      F   Y   N   Y   V   S   W   Y   Q   Q   H   P   G   K   A
 91   TTT TAT AAC TAT GTC TCC TGG TAC CAA CAG CAC CCA GGC AAA GCC
```

```
                             CDR2
                    ~~~~~~~~~~~~~~~~~~~~~~~~~
        P   E   V   M   I   Y   D   V   S   N   R   P   S   G   V
    136 CCC GAA GTC ATG ATT TAT GAT GTC AGT AAT CGG CCC TCA GGG GTT

S   D   R   F   S   G   S   K   S   G   N   Y   A   S   L
    181 TCT GAT CGC TTC TCT GGC TCC AAG TCT GGC AAC ACG GCC TCC CTG

T   I   S   G   L   Q   A   E   D   E   A   D   Y   Y   C
    226 ACT ATC TCT GGG CTC CAG GCT GAG GAC GAG GCT GAT TAT TAC TGC

CDR3
              ~~~~~~~~~~~~~~~~~~~~~~~~~~~~~
        S   S   Y   T   S   I   S   T   W   V   F   G   G   T
    261 AGC TCA TAT ACA AGC ATC AGC ACT TGG GTG TTC GGC GGA GGG ACC

K   L   T   V   L   (SEQ ID NO: 51)
    316 AAG CTG ACT GTC CTA (SEQ ID NO: 52)
```

1.103.11 hAb-VH(20975-VH): (SEQ ID NO:53 for amino acid and SEQ ID NO:54 for nucleic acid) with heavy chain CDRs 1-3: SEQ ID NOs: 1, 15, 5 are amino acid sequences and SEQ ID NO:2, 16, 6 are nucleic acid sequences, respectively:
  V segment: IGHV4-39*01
  D segment: IGHD1-26*01
  J segment: IGHJ4*02

```
        Q   L   Q   L   Q   E   S   G   P   G   L   V   K   P   S
    1   CAG CTG CAG CTG CAG GAG TCG GGC CCA GGA CTG GTG AAG CCT TCG

E   T   L   T   L   T   C   T   V   S   A   D   S   I   S
    46  GAG ACC CTG ACC CTC ACC TGC ACT GTC TCT GCT GAC TCC ATC AGC

CDR1
            ~~~~~~~~~~~~~~~~~~~~
        S   T   T   Y   Y   W   V   W   I   R   Q   P   P   G   K
    91  AGT ACT ACT TAC TAC TGG GTC TGG ATC CGC CAG CCC CCA GGG AAG

CDR2
                            ~~~~~~~~~~~~~~~~~~~~~~~~~~~~~~~~
        G   L   E   W   I   G   S   I   S   Y   S   G   S   T   Y
    136 GGA CTG GAG TGG ATT GGG AGT ATC TCT TAT AGT GGG AGC ACC TAC

CDR2
            ~~~~~~~~~~~~~~~~~~~~~
        Y   N   P   S   L   K   S   R   V   T   V   S   V   D   T
    181 TAC AAT CCG TCC CTC AAG AGT CGA GTC ACC GTA TCC GTA GAC ACG

S   K   N   Q   F   S   L   K   L   N   S   V   A   A   T
    226 TCC AAG AAC CAC TTC TCC CTG AAG CTG AAC TCT GTG GCC GCC ACA

CDR3
                                ~~~~~~~~~~~~~~~~~~~~~~~~
        D   T   A   L   Y   Y   C   A   R   H   L   G   Y   N   G
    261 GAC ACG GCT CTA TAT TAC TGT GCG AGA CAT CTA GGG TAT AAT GGG

CDR3
         ~~~~~~~~~~~~~~~~~~~~~~~~~
        R   Y   L   P   F   D   Y   W   G   Q   G   T   L   V   T
    316 AGG TAC CTC CCC TTT GAC TAC TGG GGC CAG GGA ACC CTG GTC ACC

V   S   S   (SEQ ID NO: 53)
    361 GTC TCC TCC (SEQ ID NO: 54)
```

1.103.11 hAb-VL(21038-VL): (SEQ ID NO:55 for amino acid and SEQ ID NO:56 for nucleic acid) with light chain CDRs 1-3: SEQ ID NOs: 7, 17, 19 are amino acid sequences and SEQ ID NO:8, 18, 20 are nucleic acid sequences, respectively:
  V segment: IGLV2-14*01
  J segment: IGLJ3*02

```
      Q   S   A   L   T   Q   P   A   S   V   S   G   S   P   G
    1 CAG TCT GCC CTG ACT CAG CCT GCC TCC GTG TCT GGG TCT CCT GGA
                                               CDR1
                                       ~~~~~~~~~~~~~~~~~~~~~~~~
      Q   S   I   T   I   S   C   T   G   T   S   S   D   V   G
   46 CAG TCG ATC ACC ATC TCC TGC ACT GGA ACC AGC AGT GAC GTT GGT
                CDR1
         ~~~~~~~~~~~~~~~~~~~~
      F   Y   N   Y   V   S   W   Y   Q   Q   H   P   G   K   A
   91 TTT TAT AAC TAT GTC TCC TGG TAC CAA CAG CAC CCA GGC AAA GCC
                                          CDR2
                                  ~~~~~~~~~~~~~~~~~~~~~~~~
      P   E   L   M   I   Y   D   V   S   N   R   P   S   G   V
  136 CCC GAA CTC ATG ATT TAT GAT GTC AGT AAT CGG CCC TCA GGG GTT
      S   D   R   F   S   G   S   K   S   G   N   T   A   S   L
  181 TCT GAT CGC TTC TCT GGC TCC AAG TCT GGC AAC ACG GCC TCC CTG
      T   I   S   G   L   Q   A   E   D   E   A   D   Y   Y   C
  226 ACC ATC TCT GGG CTC CAG GCT GAG GAC GAG GCT GAT TAT TAC TGC
                 CDR3
         ~~~~~~~~~~~~~~~~~~~~~~~~~~~~~~~~
      S   S   Y   T   N   I   S   T   W   V   F   G   G   G   T
  261 AGC TCA TAT ACA AAC ATC AGC ACT TGG GTG TTC GGC GGA GGG ACC
      K   L   T   V   L    (SEQ ID NO: 55)
  316 AAG CTG ACC GTC CTA  (SEQ ID NO: 56)
```

1.139.15 hAb-VH(23521-VH) (SEQ ID NO:57 for amino acid and SEQ ID NO:58 for nucleic acid) with heavy chain CDRs 1-3: SEQ ID NOs: 21, 23, 25 are amino acid sequences and SEQ ID NO:22, 24, 26 are nucleic acid sequences, respectively:
V segment: IGHV4-39*01
D segment: IGHD6-13*01
J segment: IGHJ4*02

```
      Q   L   Q   L   Q   E   S   G   P   G   L   V   K   P   S
    1 CAG CTG CAG CTG CAG GAG TCG GGC CCA GGA CTG GTG AAG CCC TCG
      E   T   L   S   L   T   C   T   V   S   G   G   S   I   S
   46 GAG ACC CTG TCC CTC ACC TGC ACT GTC TCT GGT GGC TCC ATC AGC
                CDR1
         ~~~~~~~~~~~~~~~~~~~~~~~
      S   T   T   Y   Y   W   G   W   I   R   Q   P   P   G   K
   91 AGT ACT ACT TAC TAC TGG GGC TGG ATC CGC CAG CCC CCA GGG AAG
                                          CDR2
                                  ~~~~~~~~~~~~~~~~~~~~~~~~~~~
      G   L   E   W   I   G   S   I   S   Y   S   G   T   T   Y
  136 GGG CTG GAG TGG ATT GGG AGT ATC TCT TAT AGT GGG ACC ACC TAC
                CDR2
         ~~~~~~~~~~~~~~~~~~~~
      Y   N   P   S   L   K   S   R   V   T   I   P   V   D   T
  181 TAC AAC CCG TCC CTC AAG AGT CGA GTC ACC ATC CCC GTA GAC ACG
      S   K   N   Q   I   S   L   K   L   S   S   V   T   A   A
  226 TCC AAG AAC CAC ATC TCC CTG AAA CTG AGC TCT GTG ACC GCC GCA
                                                 CDR3
                                         ~~~~~~~~~~~~~~~~~~~~~
      D   T   S   L   Y   Y   C   A   R   H   L   G   Y   N   S
  261 GAC ACG TCT TTG TAT TAT TGT GCG AGA CAT CTC GGG TAT AAC AGC
```

```
                 CDR3
       ~~~~~~~~~~~~~~~~~~
        N   W   Y   P   F   D   Y   W   G   Q   G   T   L   V   T
    316 AAC TGG TAC CCT TTT GAC TAC TGG GGC CAG GGA ACC CTG GTC ACC
        V   S   S          (SEQ ID NO: 57)
    361 GTC TCC TCA        (SEQ ID NO: 58)
```

1.139.15 hAb-VL(22895-VL) (SEQ ID NO:59 for amino acid and SEQ ID NO:60 for nucleic acid) with light chain CDRs 1-3: SEQ ID NOs: 27, 29, 31 are amino acid sequences and SEQ ID NO: 28, 30, 32 are nucleic acid sequences, respectively:
V segment: IGLV2-18*02
J segment: IGLJ3*02

```
        Q   S   A   L   T   Q   P   P   S   V   S   G   S   P   G
      1 CAG TCG GCC CTG ACT CAG CCT CCC TCC GTG TCC GGG TCT CCT GGA
                                                      CDR1
                                              ~~~~~~~~~~~~~~~~~~~~
        Q   S   V   T   I   S   C   T   G   T   S   S   D   V   G
    271 CAG TCA GTC ACC ATC TCC TGC ACT GGA ACC AGC AGT GAC GTT GGT

CDR1
       ~~~~~~~~~~~~~~~~~~~
        S   Y   N   R   V   S   W   Y   Q   Q   P   P   G   T   A
     91 AGT TAT AAC CGT GTC TCC TGG TAC CAG CAG CCC CCA GGC ACA GCC

CDR2
                                  ~~~~~~~~~~~~~~~~~~~~~~~~~~~~
        P   E   V   I   I   Y   E   V   S   N   R   P   S   G   V
    136 CCC GAA GTC ATT ATT TAT GAG GTC AGT AAT CGG CCC TCA GGG GTC

P   D   R   F   S   G   S   K   S   G   N   T   A   S   L
    181 CCT GAT CGC TTC TCT GGG TCC AAG TCT GGC AAC ACG GCC TCC CTG

T   I   S   G   L   Q   A   E   D   E   A   D   Y   Y   C
    226 ACG ATC TCT GGG CTC CAG GCT GAG GAC GAG GCT GAT TAT TAC TGC

CDR3
                 ~~~~~~~~~~~~~~~~~~~~~~~~~~~~~~~~~
        S   S   Y   T   S   S   S   T   W   V   F   G   G   G   T
    261 AGC TCA TAT ACA AGC AGC AGC ACT TGG GTG TTC GGC GGA GGG ACC
        K   L   T   V   L   (SEQ ID NO: 59)
    316 AAG CTG ACC GTC CTA (SEQ ID NO: 60)
```

1.153.7 hAb-VH(20942-VH): (SEQ ID NO:61 for amino acid and SEQ ID NO:62 for nucleic acid) with heavy chain CDRs 1-3: SEQ ID NOs: 33, 35, 37 are amino acid sequences and SEQ ID NO: 34, 36, 38 are nucleic acid sequences, respectively:
V segment: IGHV3-23*01
D segment: IGHD7-27*01
J segment: IGHJ4*02

```
        E   V   Q   L   L   E   S   G   G   G   L   V   Q   P   G
      1 GAG GTG CAG CTG TTG GAG TCT GGG GGA GGC TTG GTA CAG CCT GGG
        G   S   L   R   L   S   C   A   A   S   G   F   T   F   S
     46 GGG TCC CTG AGA CTG TCC TGC GCA GCC TCT GGA TTC ACC TTT AGC
              CDR1
       ~~~~~~~~~~~~~~~~~~
        S   H   A   M   S   W   V   R   Q   A   P   G   K   G   L
     91 AGC CAT GCC ATG AGC TGG GTC CGC CAG GCT CCA GGG AAG GGG CTG
```

```
                              CDR2
          ~~~~~~~~~~~~~~~~~~~~~~~~~~~~~~~~~~~~
      E   W   V   S   T   I   T   G   G   G   S   I   Y   Y
136  GAG TGG GTC TCA ACT ATT ACT GGT GGT GGT AGC ATA TAC TAC

CDR2
     ~~~~~~~~~~~~~~~~
      A   D   S   V   K   G   R   F   T   I   S   R   D   N   S
181  GCA GAC TCC GTG AAG GGC CGG TTC ACC ATC TCC AGA GAC AAT TCC

K   N   T   L   Y   L   Q   M   N   S   L   R   A   E   D
226  AAG AAC ACG CTG TAT CTG CAA ATG AAC AGC CTG AGA GCC GAG GAC

CDR3
                                   ~~~~~~~~~~~~~~~~~~~~~~~~~~~~
      T   A   V   Y   Y   C   A   K   N   R   A   G   E   G   Y
261  ACG GCC GTA TAT TAT TGT GCG AAA AAC CGC GCT GGG GAG GGT TAC

CDR3
     ~~~~~~~~~~
      F   D   Y   W   G   Q   G   T   L   V   T   V   S   S  (SEQ ID NO: 61)
316  TTT GAC TAC TGG GGC CAG GGA ACC CTG GTC AGG GTC TCC TGA (SEQ ID NO: 62)
```

1.153.7 hAb-VL(21110-VL) (SEQ ID NO:63 for amino acid and SEQ ID NO:64 for nucleic acid) with light chain CDRs 1-3: SEQ ID NOs: 39, 41, 43 are amino acid sequences and SEQ ID NO: 40, 42, 44 are nucleic acid sequences, respectively:
  V segment: IGLV3-9*01
  J segment: IGLJ3*02

```
      S   Y   E   L   T   Q   P   L   S   V   S   V   A   L   G
1    TCC TAT GAG CTG ACT CAG CCA CTC TCA GTG TCA GTG GCC CTG GGA

CDR1
                              ~~~~~~~~~~~~~~~~~~~~~~~~~~~~~~
      Q   T   A   R   I   T   C   G   G   D   N   I   G   N   K
46   CAG ACG GCC ACG ATT ACC TGT GGG GGA GAC AAC ATT GGA AAT AAA

CDR1
     ~~~~~~~~~~
      D   V   H   W   Y   Q   Q   K   P   G   Q   A   P   V   L
91   GAT GTG CAC TGG TAC CAG CAG AAG CCA GGC CAG GCC CCT GTG CTG

CDR2
                                   ~~~~~~~~~~~~~~~~~~~~~~~~~~~~
      V   I   Y   R   D   S   N   R   P   S   G   I   P   E   G
136  GTC ATC TAT CGA GAT AGC AAC CGG CCC TCT GGG ATC CCT GAG GGA

F   S   G   S   N   S   G   N   T   A   T   L   T   I   S
181  TTC TCT GGC TCC AAC TCG GGG AAC ACG GCC ACC CTG ACC ATC AGC

CDR3
                                          ~~~~~~~~~~~~~~~~~~~~
      R   A   Q   A   G   D   E   A   D   Y   Y   C   Q   V   W
226  AGA GCC CAA GCC GGG GAT GAG GCT GAC TAT TAC TGT CAG GTG TGG

CDR3
           ~~~~~~~~~~~~~~~~~~~~~~~~~
      D   S   I   W   V   F   G   G   G   T   K   L   T   V   L  (SEQ ID NO: 63)
261  GAC AGC ATT TGG GTG TTC GGC GGA GGG ACC AAG CTG ACC GTC CTA (SEQ ID NO: 64)
```

1.103.11-v2 hAb-VH(20975-VH): (SEQ ID NO:53 for amino acid and SEQ ID NO:54 for nucleic acid) with heavy chain CDRs 1-3: SEQ ID NOs: 1, 15, 5 are amino acid sequences and SEQ ID NO:2, 16, 6 are nucleic acid sequences, respectively:
  V segment: IGHV4-39*01
  D segment: IGHD1-26*01
  J segment: IGHJ4*02

```
      Q   L   Q   L   Q   E   S   G   P   G   L   V   K   P   S
  1 CAG CTG CAG CTG CAG GAG TCG GGC CCA GGA CTG GTG AAG CCT TCG

E   T   L   T   L   T   C   T   V   S   A   D   S   I   S
 46 CAG ACC CTG ACC CTC ACC TGC ACT GTC TCT GCT GAC TCC ATC AGC

CDR1
      S   T   T   Y   Y   W   V   W   I   R   Q   P   P   G   K
 91 AGT ACT ACT TAC TAC TGG GTC TGG ATC CGC CAG CCC CCA GGG AAG

CDR2
      G   L   E   W   I   G   S   I   S   Y   S   G   S   T   Y
136 GGA CTG GAG TGG ATT GGG AGT ATC TCT TAT AGT GGG AGC ACC TAC

CDR2
      Y   N   P   S   L   K   S   R   V   T   V   S   V   D   T
181 TAC AAT CCG TCC CTC AAG AGT CGA GTC ACC GTA TCC GTA GAC ACG

S   K   N   Q   F   S   L   K   L   N   S   V   A   A   T
226 TCC AAG AAC CAC TTC TCC CTG AAG CTG AAC TCT GTG GCC GCC ACA

CDR3
      D   T   A   L   Y   Y   C   A   R   H   L   G   Y   N   G
261 GAC ACG GCT CTA TAT TAC TGT GCG AGA CAT CTA GGG TAT AAT GGG

CDR3
      R   Y   L   P   F   D   Y   W   G   Q   G   T   L   V   T
316 AGG TAC CTC CCC TTT GAC TAC TGG GGC CAG GGA ACC CTG GTC ACC

V   S   S   (SEQ ID NO: 53)
361 GTC TCC TCC (SEQ ID NO: 54)
```

1.103.11-v2 hAb-VL(21038-2-VL): (SEQ ID NO:67 for amino acid and SEQ ID NO:68 for nucleic acid) with light chain CDRs 1-3: SEQ ID NOs: 7, 17, 65 are amino acid sequences and SEQ ID NO:8, 18, 66 are nucleic acid sequences, respectively:
V segment: IGLV2-14*01
J segment: IGLJ3*02

```
      Q   S   A   L   T   Q   P   A   S   V   S   G   S   P   G
  1 CAG TCT GCC CTG ACT CAG CCT GCC TCC GTG TCT GGG TCT CCT GGA

CDR1
      Q   S   I   T   I   S   C   T   G   T   S   S   D   V   G
 46 CAG TCG ATC ACC ATC TCC TGC ACT GGA ACC AGC AGT GAC GTT GGT

CDR1
      F   Y   N   Y   V   S   W   Y   Q   Q   H   P   G   K   A
 91 TTT TAT AAC TAT GTC TCC TCG TAC CAA CAG CAC CCA GGC AAA GCC

CDR2
      P   E   L   M   I   Y   D   V   S   N   R   P   S   G   V
136 CCC GAA CTC ATG ATT TAT GAT GTC AGT AAT CGG CCC TCA GGG GTT

S   D   R   F   S   G   S   K   S   G   N   T   A   S   L
181 TCT GAT CGC TTC TCT GGC TCC AAG TCT GGC AAC ACG GCC TCC CTG

T   I   S   G   L   Q   A   E   D   E   A   D   Y   Y   C
226 ACC ACT TCT GGG CTC CAG GCT GAG GAC GAG GCT GAT TAT TAC TGC
```

```
                       CDR3
     S    S   Y    T    S    I    S    T    W    V    F    G    G    T
261 AGC TCA TAT ACA AGC ATC AGC ACT TGG GTG TTC GGC GGA GGG ACC
     K    L   T    V    L   (SEQ ID NO: 67)
316 AAG CTG ACC GTC CTA (SEQ ID NO: 68)
```

In some embodiments, the anti-PD-1 antibodies and the antigen-binding fragments thereof comprise a heavy chain CDR sequences selected from the group consisting of: SEQ ID NOs: 1, 3, 5, 13, 15, 21, 23, 25, 33, 35 and 37. In some embodiments, the anti-PD-1 antibodies and the antigen-binding fragments thereof comprise a light chain CDR sequences selected from the group consisting of: SEQ ID NOs: 7, 9, 11, 17, 19, 27, 29, 31, 39, 41, 43 and 65. In certain embodiments, one or more CDR sequences provided herein can be modified or changed such that the resulting antibody is improved over the parent antibody in one or more properties (such as improved antigen-binding, improved glycosylation pattern, reduced risk of glycosylation on a CDR residue, reduced deamination on a CDR residue, increased pharmacokinetic half-life, pH sensitivity, and compatibility to conjugation), and is otherwise comparable to the parent antibody (i.e. antibody having otherwise the same set of CDR sequences except for the above-mentioned modification or change), or at least substantially retains the antigen-binding property of the parent antibody.

In some embodiments, the anti-PD-1 antibodies and the antigen-binding fragments thereof comprise a heavy chain variable region selected from the group consisting of: a heavy chain variable region comprising SEQ ID NO: 1, SEQ ID NO: 3, and/or SEQ ID NO: 5; a heavy chain variable region comprising SEQ ID NO: 13, SEQ ID NO: 15, and/or SEQ ID NO: 5; a heavy chain variable region comprising SEQ ID NO: 1, SEQ ID NO: 15, and/or SEQ ID NO: 5; a heavy chain variable region comprising SEQ ID NO: 21, SEQ ID NO: 23, and/or SEQ ID NO: 25; and a heavy chain variable region comprising SEQ ID NO: 33, SEQ ID NO: 35, and/or SEQ ID NO: 37.

In some embodiments, the anti-PD-1 antibodies and the antigen-binding fragments thereof comprise a light chain variable region selected from the group consisting of: a light chain variable region comprising SEQ ID NO: 7, SEQ ID NO: 9, and/or SEQ ID NO: 11; a light chain variable region comprising SEQ ID NO: 7, SEQ ID NO: 17, and/or SEQ ID NO: 11; a light chain variable region comprising SEQ ID NO: 7, SEQ ID NO: 17, and/or SEQ ID NO: 19; a light chain variable region comprising SEQ ID NO: 27, SEQ ID NO: 29, and/or SEQ ID NO: 31; a light chain variable region comprising SEQ ID NO: 39, SEQ ID NO: 41, and/or SEQ ID NO: 43; and a light chain variable region comprising SEQ ID NO: 7, SEQ ID NO: 17, and/or SEQ ID NO: 65.

In some embodiments, the anti-PD-1 antibodies and the antigen-binding fragments thereof comprising: a) a heavy chain variable region comprising SEQ ID NO: 1, SEQ ID NO: 3, and/or SEQ ID NO: 5; and a light chain variable region comprising SEQ ID NO: 7, SEQ ID NO: 9, and/or SEQ ID NO: 11; b) a heavy chain variable region comprising SEQ ID NO: 13, SEQ ID NO: 15, and/or SEQ ID NO: 5; and a light chain variable region comprising SEQ ID NO: 7, SEQ ID NO: 17, and/or SEQ ID NO: 11; c) a heavy chain variable region comprising SEQ ID NO: 1, SEQ ID NO: 15, and/or SEQ ID NO: 5; and a light chain variable region comprising SEQ ID NO: 7, SEQ ID NO: 17, and/or SEQ ID NO: 19; d) a heavy chain variable region comprising SEQ ID NO: 21, SEQ ID NO: 23, and/or SEQ ID NO: 25 and a light chain variable region comprising SEQ ID NO: 27, SEQ ID NO: 29, and/or SEQ ID NO: 31; e) a heavy chain variable region comprising SEQ ID NO: 33, SEQ ID NO: 35, and/or SEQ ID NO: 37; and a light chain variable region comprising SEQ ID NO: 39, SEQ ID NO: 41, and/or SEQ ID NO: 43; or f) a heavy chain variable region comprising SEQ ID NO: 1, SEQ ID NO: 15, and/or SEQ ID NO: 5; and a light chain variable region comprising SEQ ID NO: 7, SEQ ID NO: 17, and/or SEQ ID NO: 65.

A skilled artisan will understand that the CDR sequences provided in Table 1 can be modified to contain one or more substitutions of amino acids, so as to provide for an improved biological activity such as improved binding affinity to human PD-1. For example, a library of antibody variants (such as Fab or scFv variants) can be generated and expressed with phage display technology, and then screened for the binding affinity to human PD-1. For another example, computer software can be used to virtually simulate the binding of the antibodies to human PD-1, and identify the amino acid residues on the antibodies which form the binding interface. Such residues may be either avoided in the substitution so as to prevent reduction in binding affinity, or targeted for substitution to provide for a stronger binding. In certain embodiments, at least one (or all) of the substitution(s) in the CDR sequences is conservative substitution.

In certain embodiments, the antibodies and the antigen-binding fragments thereof comprise one or more CDR sequences having at least 80% (e.g. at least 85%, 88%, 90%, 91%, 92%, 93%, 94%, 95%, 96%, 97%, 98%, 99%) sequence identity to that (or those) listed in Table 1, and in the meantime retain the binding affinity to human PD-1 at a level similar to or even higher than its parental antibody having substantially the same sequence except that the corresponding CDR sequence is in 100% sequence identity to that (or those) listed in Table 1.

In certain embodiments, the anti-PD-1 antibodies and the antigen-binding fragments thereof are fully human. The fully human antibodies do not have the issues of immunogenicity in human and/or reduced binding affinity as often observed with humanized antibodies.

In some embodiments, the fully human anti-PD-1 antibodies and the antigen-binding fragments thereof comprise a heavy chain variable region selected from the group consisting of: SEQ ID NO: 45, SEQ ID NO: 49, SEQ ID NO: 53, SEQ ID NO: 57, SEQ ID NO: 61, and a homologous sequence thereof having at least 80% (e.g. at least 85%, 88%, 90%, 91%, 92%, 93%, 94%, 95%, 96%, 97%, 98%, 99%) sequence identity; and/or a light chain variable region selected from the group consisting of: SEQ ID NO: 47, SEQ ID NO: 51, SEQ ID NO: 55, SEQ ID NO: 59, SEQ ID NO: 63, SEQ ID NO: 67, and a homologous sequence thereof having at least 80% (e.g. at least 85%, 88%, 90%, 91%, 92%, 93%, 94%, 95%, 96%, 97%, 98%, 99%) sequence identity. Theses fully human antibodies retain the binding affinity to human PD-1, preferably at a level similar to one of the exemplary antibodies: 1.7.3 hAb, 1.49.9 hAb, 1.103.11 hAb, 1.103.11-v2 hAb, 1.139.15 hAb, and 1.153.7 hAb.

In some embodiments, the fully human anti-PD-1 antibodies and the antigen-binding fragments thereof comprise: a) a heavy chain variable region comprising SEQ ID NO: 45; and a light chain variable region comprising SEQ ID NO: 47; b) a heavy chain variable region comprising SEQ ID NO: 49; and a light chain variable region comprising SEQ ID NO: 51; c) a heavy chain variable region comprising SEQ ID NO: 53; and a light chain variable region comprising SEQ ID NO: 55; d) a heavy chain variable region comprising SEQ ID NO: 57; and a light chain variable region comprising SEQ ID NO: 59; e) a heavy chain variable region comprising SEQ ID NO: 61; and a light chain variable region comprising SEQ ID NO: 63; or f) a heavy chain variable region comprising SEQ ID NO: 53; and a light chain variable region comprising SEQ ID NO: 67.

Also contemplated herein are antibodies and the antigen-binding fragments that compete for the same epitope with the anti-PD-1 antibodies and the antigen-binding fragments thereof provided herein. In certain embodiments, the antibodies block binding of 1.7.3 hAb, 1.49.9 hAb, 1.103.11 hAb, 1.103.11-v2 hAb, 1.139.15 hAb, or 1.153.7 hAb to human or monkey PD-1, for example, at an IC50 value (i.e. 50% inhibition concentration) of below $10^{-6}$ M, below $10^{-7}$ M, below $10^{-7.5}$ M, below $10^{-8}$ M, below $10^{-8.5}$ M, below $10^{-9}$ M, or below $10^{-10}$ M. The $IC_{50}$ values are determined based on a competition assay such as ELISA assays, radio-ligand competition binding assays, and FACS analysis.

In some embodiments, the anti-PD-1 antibodies and the antigen-binding fragments thereof provided herein are capable of specifically binding to human PD-1 with a binding affinity (Kd) of $\leq 10^{-6}$ M (e.g., $\leq 5\times10^{-7}$ M, $\leq 2\times10^{-7}$ M, $\leq 10^{-7}$ M, $\leq 5\times10^{-8}$ M, $\leq 2\times10^{-8}$ M, $\leq 10^{-8}$ M, $\leq 5\times10^{-9}$M, $\leq 2\times10^{-9}$M, $\leq 10^{-9}$M, $10^{-10}$ M) as measured by plasmon resonance binding assay. The binding affinity can be represented by $K_D$ value, which is calculated as the ratio of dissociation rate to association rate ($k_{off}/k_{on}$) when the binding between the antigen and the antigen-binding molecule reaches equilibrium. The antigen-binding affinity (e.g. $K_D$) can be appropriately determined using suitable methods known in the art, including, for example, plasmon resonance binding assay using instruments such as Biacore (see, for example, Murphy, M. et al, Current protocols in protein science, Chapter 19, unit 19.14, 2006).

In certain embodiments, the antibodies and the fragments thereof provided herein binds to human PD-1 with an $EC_{50}$ (i.e. 50% binding concentration) of 0.1 nM-100 nM (e.g. 0.1 nM-50 nM, 0.1 nM-30 nM, 0.1 nM-20 nM, 0.1 nM-10 nM, or 0.1 nM-1 nM). Binding of the antibodies to human PD-1 can be measured by methods known in the art, for example, sandwich assay such as ELISA, Western Blot, FACS or other binding assay. In an illustrative example, the test antibody (i.e. first antibody) is allowed to bind to immobilized human PD-1 or cells expressing human PD-1, after washing away the unbound antibody, a labeled secondary antibody is introduced which can bind to and thus allow detection of the bound first antibody. The detection can be conducted with a microplate reader when immobilized PD-1 is used, or by using FACS analysis when cells expressing human PD-1 are used. In certain embodiments, the antibodies and the fragments thereof provided herein binds to human PD-1 with an $EC_{50}$ (i.e. 50% effective concentration) of 1 nM to 10 nM, or 1 nM to 5 nM as measured by FACS analysis.

In certain embodiments, the antibodies and the fragments thereof provided herein inhibit the binding of human PD-1 to its ligand at an $IC_{50}$ of 0.2 nM-100 nM (e.g. 0.2 nM-50 nM, 0.2 nM-30 nM, 0.2 nM-20 nM, 0.2 nM-10 nM, or 1 nM-10 nM), as measured in a competition assay.

In certain embodiments, the antibodies and the fragments thereof provided herein block binding of human PD-1 to its ligand and thereby providing biological activity including, for example, inducing cytokine production from the activated T cells (such as $CD4^+$ T cells and $CD8^+$ T cells), inducing proliferation of activated T cells (such as CD4+ T cells and $CD8^+$ T cells), and reversing T reg's suppressive function. Exemplary cytokines include IL-2 and IFNγ. The term "IL-2" refers to interleukin 2, a type of cytokine signaling molecule in the immune system that regulates the activities of white blood cells (e.g. leukocytes). The term "Interferon gamma (IFNγ)" is a cytokine that is produced by natural killer (NK), NK T cells, $CD4^+$ and $CD8^+$T cells, which is a critical activator of macrophages and inducer of major histocompatibility complex (MHC) molecule expression. The cytokine production can be determined using methods known in the art, for example, by ELISA. Methods can also be used to detect proliferation of T cells, including [$^3$H] thymidine incorporation assay.

The anti-PD-1 antibodies and the antigen-binding fragments thereof are specific for PD-1. In certain embodiments, the antibodies and antigen-binding fragments thereof do not bind to CD28 and/or CTLA-4. For example, the binding affinity with CD28 and/or CTLA-4 is less than 15%, 10%, 9%, 8%, 7%, 6%, 5%, 4%, 3%, 2%, or 1% of that with PD-1.

In certain embodiments, the antibodies and antigen-binding fragments thereof bind to monkey PD-1 at an EC50 of no more than 100 nM, for example, no more than or about 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM, as measured by ELISA. In certain embodiments, the antibodies and antigen-binding fragments thereof bind to monkey PD-1 at an EC50 of about 1 nM-10 nM.

In certain embodiments, the antibodies and antigen-binding fragments thereof do not bind to mouse PD-1 but bind to monkey PD-1 with a binding affinity similar to that of human PD-1. For example, binding of the exemplary antibodies 1.7.3 hAb, 1.49.9 hAb, 1.103.11 hAb, 1.103.11-v2 hAb, 1.139.15 hAb, and 1.153.7 hAb to mouse PD-1 is not detectable in conventional binding assays such as ELISA, or FACS analysis, whereas the binding of these antibodies to monkey PD-1 is at a similar affinity or EC50 value to that of human PD-1 as measured by ELISA or FACS.

In some embodiments, the anti-PD-1 antibodies and the antigen-binding fragments thereof has reduced or depleted effector function. In some embodiments, the anti-PD-1 antibodies and the antigen-binding fragments thereof have a constant region of IgG4 isotype, which has reduced or depleted effector function. Effector functions such as ADCC and CDC can lead to cytotoxicity to cells expressing PD-1. Many cells such as T cells normally express PD-1. In order to avoid potential unwanted toxicity to those normal cells, certain embodiments of the antibodies and antigen-binding fragments provided herein can possess reduced or even depleted effector functions. Various assays are known to evaluate ADCC or CDC activities, for example, Fc receptor binding assay, C1q binding assay, and cell lysis assay, and can be readily selected by people in the art. Without wishing to be bound to theory, but it is believed that antibodies with reduced or depleted effector functions such as ADCC or CDC would cause no or minimal cytotoxicity to PD-1-expressing cells, for example those T cells, and therefore spare them from unwanted side effects, whereas in the meantime, blocking of PD-1 would boost immune system for the treatment of conditions such as cancer or chronic infection.

In certain embodiments, the anti-PD-1 antibodies and antigen-binding fragments thereof provided herein have reduced side effects. For example, the antibodies and antigen-binding fragments thereof provided herein can have fully human IgG sequence and therefore reduced immunogenicity than a humanized antibody counterpart. For another example, the antibodies and antigen-binding fragments thereof provided herein can be in IgG4 format to eliminate ADCC and CDC.

In certain embodiments, the anti-PD-1 antibodies and antigen-binding fragments thereof provided herein are advantageous in that they can be used in combination with immunogenic agents, such as tumor cells, purified tumor antigen, and cells transfected with genes encoding immune stimulating cytokines, tumor vaccines. In addition, the anti-PD-1 antibodies and antigen-binding fragments thereof can be included in combination therapies, including standard chemo- and radio-therapies, target based small molecule therapies, emerging other immune checkpoint modulator therapies. In certain embodiments, the antibodies and antigen-binding fragments thereof can be used as the base of antibody-drug conjugates, bispecific or multivalent antibodies.

The anti-PD-1 antibodies or antigen-binding fragments thereof provided herein can be a monoclonal antibody, polyclonal antibody, fully human antibody, humanized antibody, chimeric antibody, recombinant antibody, bispecific antibody, labeled antibody, bivalent antibody, or anti-idiotypic antibody. A recombinant antibody is an antibody prepared in vitro using recombinant methods rather than in animals. A bispecific or bivalent antibody is an artificial antibody having fragments of two different monoclonal antibodies and can bind two different antigens. An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

In some embodiments, the anti-PD-1 antibodies or antigen-binding fragments thereof provided herein are fully human antibodies. In certain embodiments, the fully human antibodies are prepared using recombinant methods. For example, transgenic animal such as a mouse can be made to carry transgenes or transchromosomes of human immunoglobulin genes, and therefore capable of producing fully human antibodies after immunization with proper antigen such as human PD-1. Fully human antibodies can be isolated from such transgenic animal, or alternatively, can be made by hybridoma technology by fusing the spleen cells of the transgenic animal with an immortal cell line to generate hybridoma cells secreting the fully human antibodies. Exemplary transgenic animals include, without limitation, OmniRat, whose endogenous expression of rat immunoglobulin genes are inactivated and at the same time engineered to contain functional recombinant human immunoglobulin loci; OmniMouse, whose endogenous expression of mouse immunoglobulin genes are inactivated and at the same time engineered to contain recombinant human immunoglobulin loci having J-locus deletion and a C-kappa mutation; OmniFlic, which is a transgenic rat whose endogenous expression of rat immunoglobulin genes are inactivated and at the same time engineered to contain recombinant human immunoglobulin loci having a single common, rearranged VkJk light chain and functional heavy chain. Detailed information can be further found at: Osborn M. et al, Journal of Immunology, 2013, 190: 1481-90; Ma B. et al, Journal of Immunological Methods 400-401 (2013) 78-86; Geurts A. et al, Science, 2009, 325:433; U.S. Pat. No. 8,907,157; EP patent 2152880B1; EP patent 2336329B1, all of which are incorporated herein by reference to its entirety. Other suitable transgenic animals can also be used, for example, HuMab mice (see, for details, Lonberg, N. et al. Nature 368(6474): 856 859 (1994)), Xeno-Mouse (Mendez et al. Nat Genet., 1997, 15:146-156), TransChromo Mouse (Ishida et al. Cloning Stem Cells, 2002, 4:91-102) and VelocImmune Mouse (Murphy et al. Proc Natl Acad Sci USA, 2014, 111:5153-5158), Kymouse (Lee et al. Nat Biotechnol, 2014, 32:356-363), and transgenic rabbit (Flisikowska et al. PLoS One, 2011, 6:e21045).

In some embodiments, the anti-PD-1 antibodies and the antigen-binding fragments thereof is a camelized single domain antibody, a diabody, a scFv, an scFv dimer, a BsFv, a dsFv, a (dsFv)2, a dsFv-dsFv', an Fv fragment, a Fab, a Fab', a F(ab')2, a ds diabody, a nanobody, a domain antibody, or a bivalent domain antibody.

In some embodiments, the anti-PD-1 antibodies and the antigen-binding fragments thereof further comprise an immunoglobulin constant region. In some embodiments, an immunoglobulin constant region comprises a heavy chain and/or a light chain constant region. The heavy chain constant region comprises CH1, CH1-CH2, or CH1-CH3 regions. In some embodiments, the constant region may further comprise one or more modifications to confer desirable properties. For example, the constant region may be modified to reduce or deplete one or more effector functions, to improve FcRn receptor binding, or to introduce one or more cysteine residues.

In some embodiments, the anti-PD-1 antibodies and the antigen-binding fragments thereof further comprise a conjugate. It is contemplated that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate. In certain embodiments, the antibodies may be linked to a conjugate indirectly, or through another conjugate. For example, the antibody or antigen-binding fragments may be conjugated to biotin, then indirectly conjugated to a second conjugate that is conjugated to avidin. The conjugate can be a detectable label, a pharmacokinetic modifying moiety, a purification moiety, or a cytotoxic moiety. Examples of detectable label may include a fluorescent labels (e.g. fluorescein, rhodamine, dansyl, phycoerythrin, or Texas Red), enzyme-substrate labels (e.g. horseradish peroxidase, alkaline phosphatase, luceriferases, glucoamylase, lysozyme, saccharide oxidases or β-D-galactosidase), radioisotopes (e.g. $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{177}$Lu, $^{211}$At, $^{186}$Re, $^{188}$Re, $^{153}$Sm, $^{212}$Bi, and $^{32}$P, other lanthanides, luminescent labels), chromophoric moiety, digoxigenin, biotin/avidin, a DNA molecule or gold for detection. In certain embodiments, the conjugate can be a pharmacokinetic modifying moiety such as PEG which helps increase half-life of the antibody. Other suitable polymers include, such as, carboxymethylcellulose, dextran, polyvinyl alcohol, polyvinyl pyrrolidone, copolymers of ethylene glycol/propylene glycol, and the like. In certain embodiments, the conjugate can be a purification moiety such as a magnetic bead. A "cytotoxic moiety" can be any agent that is detrimental to cells or that can damage or kill cells. Examples of cytotoxic moiety include, without limitation, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin and analogs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Polynucleotides and Recombinant Methods

The present disclosure provides isolated polynucleotides that encode the anti-PD-1 antibodies and the antigen-binding fragments thereof. In certain embodiments, the isolated polynucleotides comprise one or more nucleotide sequences as shown in Table 1, which encodes the CDR sequences provided in Table 1.

In some embodiments, the isolated polynucleotides encodes a heavy chain variable region and comprise a sequence selected from the group consisting of: SEQ ID NO: 46, SEQ ID NO: 50, SEQ ID NO: 54, SEQ ID NO: 58, SEQ ID NO: 62, and a homologous sequence thereof having at least 80% (e.g. at least 85%, 88%, 90%, 91%, 92%, 93%, 94%, 95%, 96%, 97%, 98%, 99%) sequence identity. In some embodiments, the isolated polynucleotides encodes a light chain variable region and comprise a sequence selected from the group consisting of: SEQ ID NO: 48, SEQ ID NO: 52, SEQ ID NO: 56, SEQ ID NO: 60, SEQ ID NO: 64, SEQ ID NO: 68, and a homologous sequence thereof having at least 80% (e.g. at least 85%, 88%, 90%, 91%, 92%, 93%, 94%, 95%, 96%, 97%, 98%, 99%) sequence identity. In certain embodiments, the percentage identity is due to genetic code degeneracy, while the encoded protein sequence remains unchanged.

The isolated polynucleotide that encodes the anti-PD-1 antibodies and the antigen-binding fragments thereof (e.g. including the sequences in Table 1) can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence.

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc, and other laboratory and commercially available vectors. Suitable vectors may include, plasmid, or viral vectors (e.g., replication defective retroviruses, adenoviruses and adeno-associated viruses).

Vectors comprising the polynucleotide sequence encoding the antibody or antigen-binding fragment can be introduced to a host cell for cloning or gene expression. Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*.

In addition to prokaryotes, eukaryotic microbes such as filamentous fungi or yeast are suitable cloning or expression hosts for anti-PD-1 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibodies or antigen-fragment provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruifly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, *petunia*, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2). In some preferable embodiments, the host cell is 293F cell.

Host cells are transformed with the above-described expression or cloning vectors for anti-PD-1 antibody production and cultured in conventional nutrient media modified as appropriate for inducing promoters, selecting transformants, or amplifying the genes encoding the desired sequences.

The host cells used to produce the antibodies or antigen-binding fragments provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657, 866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10:163-167 (1992) describe a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human .gamma.1, .gamma.2, or .gamma.4 heavy chains (Lindmark et al., J. Immunol. Meth. 62:1-13 (1983)). Protein G is recommended for all mouse isotypes and for human .gamma.3 (Guss et al., EMBO J. 5:1567 1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Kits

The present disclosure provides kits comprising the anti-PD-1 antibodies or the antigen-binding fragments thereof. In some embodiments, the kits are useful for detecting the presence or level of PD-1 in a biological sample. The biological sample can comprise a cell or a tissue.

In some embodiments, the kit comprises an anti-PD-1 antibody or the antigen-binding fragment thereof which is conjugated with a detectable label. In certain other embodiments, the kit comprises an unlabeled anti-PD-1 antibody or antigen-binding fragment, and further comprises a secondary labeled antibody which is capable of binding to the unlabeled anti-PD-1 antibody. The kit may further comprise an instruction of use, and a package that separates each of the components in the kit.

In certain embodiments, the anti-PD-1 antibody or the antigen-binding fragment thereof are associated with a substrate or a device useful in a sandwich assay such as ELISA, or in an immunographic assay. Useful substrate or device can be, for example, microtiter plate and test strip.

Pharmaceutical Composition and Method of Treatment

The present disclosure further provides pharmaceutical compositions comprising the anti-PD-1 antibodies or the antigen-binding fragments thereof and one or more pharmaceutically acceptable carriers.

Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment and conjugates as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-PD-1 antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Therapeutic methods are also provided, comprising: administering a therapeutically effective amount of the antibody or antigen-binding fragment as provided herein to a subject in need thereof, thereby treating or preventing a condition or a disorder associated with related to PD-1. In another aspect, methods are provided to treat a condition in a subject that would benefit from upregulation of immune response, comprising administering a therapeutically effective amount of the antibody or antigen-binding fragment as provided herein to a subject in need thereof.

The therapeutically effective amount of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of tumor development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

Conditions and disorders associated with PD-1 can be immune related disease or disorder. In certain embodiments, the PD-1 associated conditions and disorders include tumors and cancers, for example, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies, such as classical Hodgkin lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma. In certain embodiments, the tumors and cancers are metastatic, especially metastatic tumors expressing PD-L1. In certain embodiments, the PD-1 associated conditions and disorders include autoimmune diseases, such as systemic lupus erythematosus (SLE), psoriasis, systemic scleroderma, autoimmune diabetes and the like. In certain embodiments, the PD-1 associated conditions and disorders include infectious disease such as chronic viral infection, for example, viral infection of hepatitis B, hepatitis C, herpes virus, Epstein-Barr virus, HIV, cytomegalovirus, herpes simplex virus type I, herpes simplex virus type 2, human papilloma virus, adenovirus, Kaposi West sarcoma associated herpes virus epidemics, thin ring virus (Torquetenovirus), JC virus or BK virus.

Methods of Use

The present disclosure further provides methods of using the anti-PD-1 antibodies or the antigen-binding fragments thereof.

In some embodiments, the present disclosure provides methods of treating a condition or a disorder associated with related to PD-1 in an individual, comprising administering a therapeutically effective amount of the anti-PD-1 antibody or antigen-binding fragment thereof. In certain embodiments, the individual has been identified as having a disorder or condition likely to respond to a PD-1 antagonist.

The presence or level of PD-L1 on an interested biological sample can be indicative of whether the individual from whom the biological sample is derived could likely respond to a PD-1 antagonist. Various methods can be used to determine the presence or level of PD-L1 in a test biological sample from the individual. For example, the test biological sample can be exposed to anti-PD-L1 antibody or antigen-binding fragment thereof, which binds to and detects the expressed PD-L1 protein. Alternatively, PD-L1 can also be detected at nucleic acid expression level, using methods such as qPCR, reverse transcriptase PCR, microarray, SAGE, FISH, and the like. In some embodiments, the test sample is derived from a cancer cell or tissue, or tumor infiltrating immune cells. In certain embodiments, presence or upregulated level of the PD-L1 in the test biological sample indicates likelihood of responsiveness. The term "upregulated" as used herein, refers to an overall increase of no less than 10%, 15%, 20%, 25%, 30%, 35%, 40%, 45%, 50%, 55%, 60%, 65%, 70%, 75%, 80% or greater, in the protein level of PD-L1 in the test sample as detected using the antibodies or antigen-binding fragments provided herein, as compared to the PD-L1 protein level in a reference sample as detected using the same antibody. The reference sample can be a control sample obtained from a healthy or non-diseased individual, or a healthy or non-diseased sample obtained from the same individual from whom the test sample is obtained. For example, the reference sample can be a non-diseased sample adjacent to or in the neighborhood of the test sample (e.g. tumor).

The antibodies or antigen-binding fragments disclosed herein may be administered alone or in combination with one or more additional therapeutic means or agents. For example, the antibodies or antigen-binding fragments disclosed herein may be administered in combination with chemotherapy, radiation therapy, surgery for the treatment of cancer (e.g., tumorectomy), one or more anti-emetics or other treatments for complications arising from chemotherapy, or any other therapeutic agent for use in the treatment of cancer or any medical disorder mediated by PD-1. In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may be administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (Physicians' Desk Reference, 57th Ed; Medical Economics Company; ISBN: 1563634457; 57th edition (November 2002)) or protocols well known in the art.

In certain embodiments, the therapeutic agents can induce or boost immune response against cancer. For example, a tumor vaccine can be used to induce immune response to certain tumor or cancer. Cytokine therapy can also be used to enhance tumor antigen presentation to the immune system. Examples of cytokine therapy include, without limitation, interferons such as interferon-α, -β, and -γ, colony stimulating factors such as macrophage-CSF, granulocyte macrophage CSF, and granulocyte-CSF, interleukins such IL-1, IL-1a, IL-2, IL-3, IL-4, IL-5, IL-6, IL-7, IL-8, IL-9, IL-10, IL-11, and IL-12, tumor necrosis factors such as TNF-α and TNF-β. Agents that inactivate immunosuppressive targets can also be used, for example, TGF-beta inhibitors, IL-10 inhibitors, and Fas ligand inhibitors. Another group of agents include those that activate immune responsiveness to tumor or cancer cells, for example, those enhance T cell activation (e.g. agonist of T cell costimulatory molecules such as CTLA-4, ICOS and OX-40), and those enhance dendritic cell function and antigen presentation.

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1: Antibody Hybridoma Generation 1.1 Immunogen Generation:

DNAs encoding PD-1 and PD-L1 ECD or full length were synthesized and inserted into the expression vector pcDNA3.3. Max-prep the plasmid DNAs and the inserted DNA sequences were verified by sequencing. Fusion proteins PD-1 ECD and PD-L1 ECD containing various tags, including human Fc, mouse Fc and His tags, were obtained by transfection of human PD-1 ECD gene into CHO-S or HEK293 cells. After 5 days, supernatants harvested from the culture of transiently transfected cells were used for protein purification. The fusion proteins were purified and quantitated for usage of immunization and screening.

1.2 Stable Cell Lines Establishment.

In order to obtain tools for antibody screening and validation, we generated PD-1 and PD-L1 transfectant cell lines. Briefly, CHO-K1, 293F or Ba/F3 cells were transfected with pCND3.3 expression vector containing full-length PD-1 or PD-L1 using Lipofectamine 2000 Transfection kit according to manufacturer's protocol. At 48-72 hours post transfection, the transfected cells were cultured in medium containing Blasticidin or G418 for selection. Overtime this will select the cells that have stably incorporated PD-1 or PD-L1 genes into their genomic DNAs. Meanwhile the cells were checked for interested genes PD-1 and PD-L1 expression. Once the expression verified, single clones of interested were picked up by limited dilution and scaled up to large volumes. The established monoclonal cell lines then were maintained in medium containing lower dose of antibiotics Blasticidin or G418.

1.3 Antibody Hybridoma Generation.

1.3.1 Immunization and Cell Fusion:

OMT-rats (obtained from Open Monoclonal Technology, Inc., Palo Alto, US), 8-10 weeks of age, were immunized with 10 µg of human PD-1 ECD protein in TiterMax in footpad for first boost, repeat the immunization every 3 days with PD-1 ECD protein in Aluminium. Bleed rats every two weeks for serum collection and antibody titers were measured by ELISA or FACS assay. When the antibody titer reached sufficient high, rats were given a final boost without adjuvant (add 100 µl 1×PBS instead) and cell fusion was performed as following: B lymphocytes isolated from lymph node of immunized OMT-rats were combined with myeloma cells (at 1:1 ratio). Cell mixture were washed and suspended with 5-10 ml ECF solution. Add ECF solution to adjust the concentration to $2\times10^6$ cells/ml. After electronic cell fusion, cell suspension from the fusion chamber was immediately transferred into a sterile tube containing more volume of medium. After incubation for more than 24 hours in a 37° C., the cell suspension was mixed and pipetted into 96-well plates ($0.5\times10^6$ cells/plate). Cells were incubated at 37° C., 5% $CO_2$. When the clones were big enough, transfer 100 µl supernatant from the 96-well plates to assay for antibody screening.

1.3.2 First and Confirmation Screen of Hybridoma Supernatants:

ELISA assay was used as first screen method to test the binding of hybridoma supernatants to PD-1 protein. Briefly, Plates (Nunc) were coated with soluble protein of human PD-1 extracellular domain at 1 µg/ml overnight at 4° C. After blocking and washing, the hybridoma supernatants were transferred to the coated plates and incubate at room temperature for 1 h. The plates were then washed and subsequently incubated with secondary antibody goat anti rat IgG1 HRP (Bethyl) and goat anti rat IgG2b HRP (Bethyl) for 45 min. After washing, TMB substrate was added and the interaction was stopped by 2M HCl. The absorbance at 450 nm was read using a microplate reader (Molecular Device). In order to confirm the native binding of PD-1 antibodies on conformational PD-1 molecules expressed on cell membrane, FACS analysis was performed on PD-1 transfected CHO-S cell line. CHO-S cells expressing human PD-1 were transferred in to 96-well U-bottom plates (BD) at a density of $1\times10^6$ cells/ml. The hybridoma supernatants were then transferred to the plates and incubated for 1 h at 4° C. After washing with 1×PBS/1% BSA, the secondary antibody goat anti rat FITC (Jackson Immunoresearch Lab) was applied and incubated with cells at 4° C. in the dark for 1 h. The cells were then washed and resuspended in 1×PBS/1% BSA or fixed with 4% paraformldehyde, and analyzed by flow cytometery (BD). Antibody binding to parental CHO-S cell line was performed using the same method. FIG. 1 shows the binding of anti-human PD-1 antibodies to PD-1 expressing CHO cell. The CHO cells transfected with full-length human PD-1 were stained with antibodies against human PD-1 from rat hybridoma, followed by 2nd antibody staining with FITC conjugated goat anti-rat-IgG Fc and analyzed by FACS. The data show that the antibodies specifically bind to PD-1 expressed on CHO cells.

Figure 3:
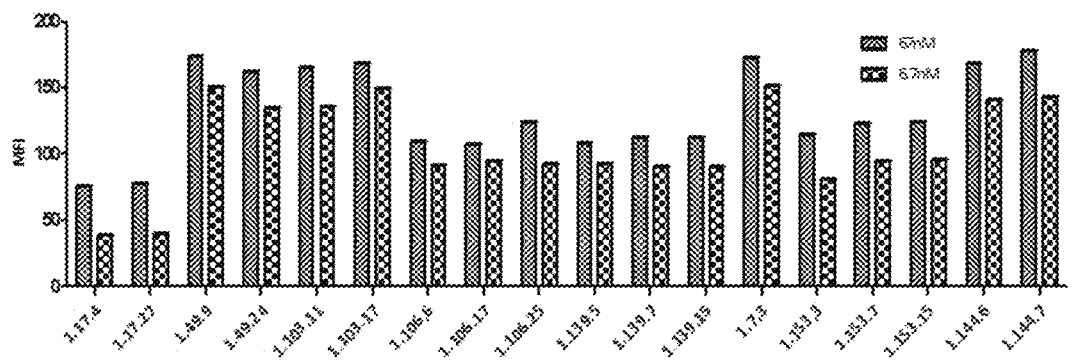
FIG. 3 is the binding of fully human anti-PD-1 antibody to PD-1 expressed on activated CD4+T cell as measured by FACS analysis.

To test the binding affinity of the antibodies to native PD-1 expressed on human CD4+T cells, human CD4+T cell were generated from PBMC cultured in IL-2 and OKT3 for 3 days and were stained with the antibodies against human PD-1. Binding of the antibodies to the PD-1 on the T cells were analyzed by FACS. As shown in FIG. 3, FACS analysis showed that the antibodies specially bind to native PD-1 expressed on CD4+T cells.

Testing the blocking activity of antibodies was used as confirmation screen to select potential antibody hits. Selected antibodies were tested for the ability to block the binding of the ligand PD-L1 to PD-1 transfected CHO-S cells by FACS analysis. CHO-S cells expressing human PD-1 were transferred in to 96-well U-bottom plates (BD) at a density of $1 \times 10^6$ cells/ml. Antibodies were serially diluted in wash buffer (1xPBS/1% BSA) and incubated with the cells at 4° C. for 1 h. After washing, human Fc fusion-human PD-L1 protein was added and incubated at 4° C. for 1 h. The secondary antibody goat anti human IgG Fc FITC antibody (no cross-reactivity to rat IgG Fc, Jackson Immunoresearch Lab) was incubated with cells at 4° C. in the dark for 1 h. The cells were then washed and resuspended in 1xPBS/1% BSA or fixed with 4% paraformldehyde, and analyzed by flow cytometry (BD).

1.3.3 Hybridoma Subcloning:

Once specific binding and blocking were verified through first and confirmation screen, the positive hybridoma cell lines can be used for subcloning. Briefly, for each hybridoma cell line, cells were counted and diluted to give 5 cells/well, 1 cell/well and 0.5 cell/well in cloning medium. Plate 200W/well into 96-well plates, one plate at 5 cells/well, one plate at 1 cell/well and four plates at 0.5 cell/well. Place all plates in incubator at 37° C., 5% $CO_2$. Incubate until all the cell lines can be checked by ELISA assay.

Example 2: Antibody Hybridoma Cell Sequence and Fully Human Antibody Characterization 2.1 Antibody Hybridoma Cell Sequence:

RNAs were isolated from monoclonal hybridoma cells with Trizol reagent. The VH and VL of PD-1 antibodies were amplified as following protocol: briefly, RNA is first reverse transcribed into cDNA using a reverse transcriptase as described here, Reaction system (20 μl):

| | |
|---|---|
| 10 × RT Buffer | 2.0 μl |
| 25 × dNTP Mix (100 mM) | 0.8 μl |
| 10 × RT Random Primers/oligodT/specific primer | 2.0 μl |
| MultiScribe ™ Reverse Transcriptase | 1.0 μl |
| RNase Inhibitor | 1.0 μl |
| RNA | 2 μg |
| Nuclease-free H<sub>2</sub>O to 20.0 μl | |

Reaction Condition

| | Step1 | Step 2 | Step3 | Step4 |
|---|---|---|---|---|
| Temperature | 25 | 37 | 85 | 4 |
| Time | 10 min | 120 min | 5 min | ∞ |

The resulting cDNA is used as templates for subsequent PCR amplification using primers specific for interested genes. The PCR reaction was done as following procedure;

| | |
|---|---|
| cDNA | 1 μl |
| Ex PCR buffer | 5 μl |
| dNTP | 2 μl |
| ExTaq | 0.5 μl |
| P1(25 pM) | 0.5 μl |
| P2(25 pM) | 0.5 μl |
| ddH<sub>2</sub>O | 40.5 μl |

Reaction Condition:
94° C. 3 min $$\left.\begin{array}{l} 94° C\quad 30\ s \\ 60° C\quad 30\ s \\ 72° C\quad 1\ min \end{array}\right\} 30\ cycles$$

72° C. 10 min

Take 10 μl of PCR reaction to do the ligation with pMD18-T vector. Do the transformation of Top10 competent cells with 10 μl ligation products and Transfer the mixture onto the pre-warmed 2-YT+Cab plates follow the standard protocol, incubate overnight. Positive clones were checked by PCR using M13-48 and M13-47 primers followed by sequencing.

2.2 Fully Human Antibody Molecule Construction:

The VH and VL of PD-1 antibodies were amplified as described above. The PCR reactions were purified with PCR clean-up kit and the VL and pCI vector were digested with restriction enzymes Pme I and BssH II at 37° C. for 2 hours. Run the reactions in 1% agarose and do gel extraction with kit according to manufacturer's instruction. Ligation of digested VL and pCI vector as following procedures:

| Component | Volume |
|---|---|
| pCI-vector | 80 ng |
| VL fragments (insert) | 100 ng |
| T4 DNA ligase Buffer | 1 μl |
| T4 DNA ligase | 0.5 μl |
| ddH<sub>2</sub>O | To 10 μl. |

The mixture was incubated at 16° C. for 30 minutes. 10 μl of the reactions was used for transformation and clone growth. Confirmed clones were used for the extraction of the plasmid pCI-VL DNA. The pCI-VL vector and VH fragment were then digested with XbaI and Sal I and the purified digested VH and vector were ligated with T4 DNA ligase 30 minutes at 16° C. Once the sequence of inserted VL and VH were verified by sequencing, the expression vector containing whole IgG of fully human PD-1 antibody was used for transient transfection and stable cell line development.

Figure 2:
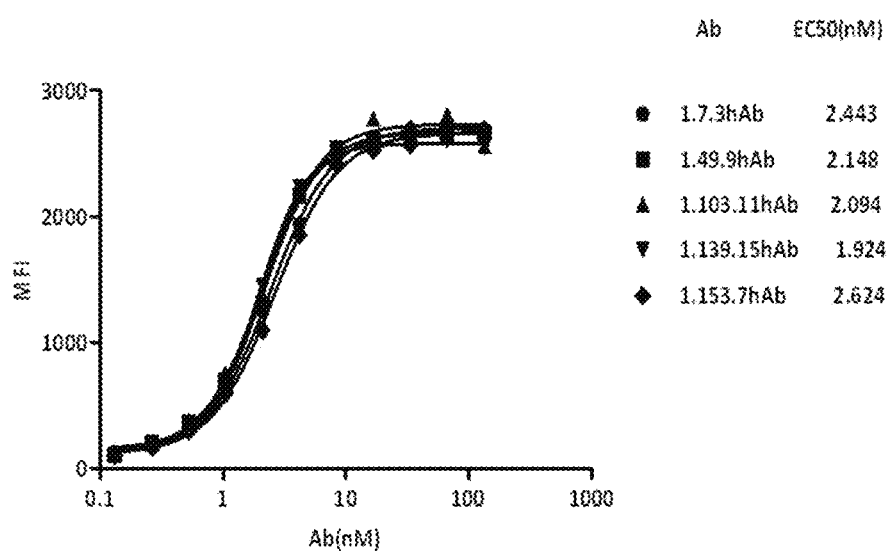
FIG. 2 presents the binding of fully human PD-1 antibodies to PD-1 expressing CHO cell with EC50 about 2 nM as measured by FACS analysis.

Example 3: Fully Human Antibody Characterization 3.1 Binding Affinity of PD-1 Antibodies to Cell Surface PD-1 Molecules Tested by Flow Cytometry (FACS):

Antibody binding affinity to cell surface PD-1 was performed by FACS analysis. CHO-S cells expressing human PD-1 were transferred in to 96-well U-bottom plates (BD) at a density of $5 \times 10^5$ cells/ml. Tested antibodies were 1:2 serially diluted in wash buffer (1xPBS/1% BSA) and incubated with cells at 4° C. for 1 h. The secondary antibody goat anti-human IgG Fc FITC (3.0 moles FITC per mole IgG, (Jackson Immunoresearch Lab) was added and incubated at 4° C. in the dark for 1 h. The cells were then washed once and resuspended in 1×PBS/1% BSA, and analyzed by flow cytometery (BD). Fluorescence intensity will be converted to bound molecules/cell based on the quantitative beads Quantum™ MESF Kits, Bangs Laboratories, Inc.). KD was calculated using Graphpad Prism5. FIG. 2 shows the binding of the fully human PD-1 antibodies (i.e. 1.7.3 hAb, 1.49.9 hAb, 1.103.11 hAb, 1.139.15 hAb, and 1.153.7 hAb) to PD-1 expressing CHO cell. Fully human antibodies against human PD-1 were used to stain the PD-1 transfected CHO cells and the FACS analysis show that fully human PD-1 antibodies specially bind to PD-1 with $EC_{50}$ about 2 nmol/L.

The 1.103.11-v2 hAb was generated by mutating a single amino acid Asn93 (Kabat Numbering) on the original antibody 1.103.11 hAb-VH(20975-VL) to residue Serine, so as to reduce the risk of glycosylation on the CDR residue. Although Asn93 is located in light chain CDR3, the antibody-antigen complex model generated from computational docking suggested that Asn93 has no direct contact with any residue on the antigen of human PD-1. Most of the binding function of the light chain CDR3 seemed to be contributed by the neighboring residue Tyr91, which has interactions with some residues on PD-1 FG loop. The cell-based functional assays of 1.103.11-v2 hAb confirmed that the mutation did not affect any binding capability (see below experimental results and FIGS. 15 and 16).

Figure 16:
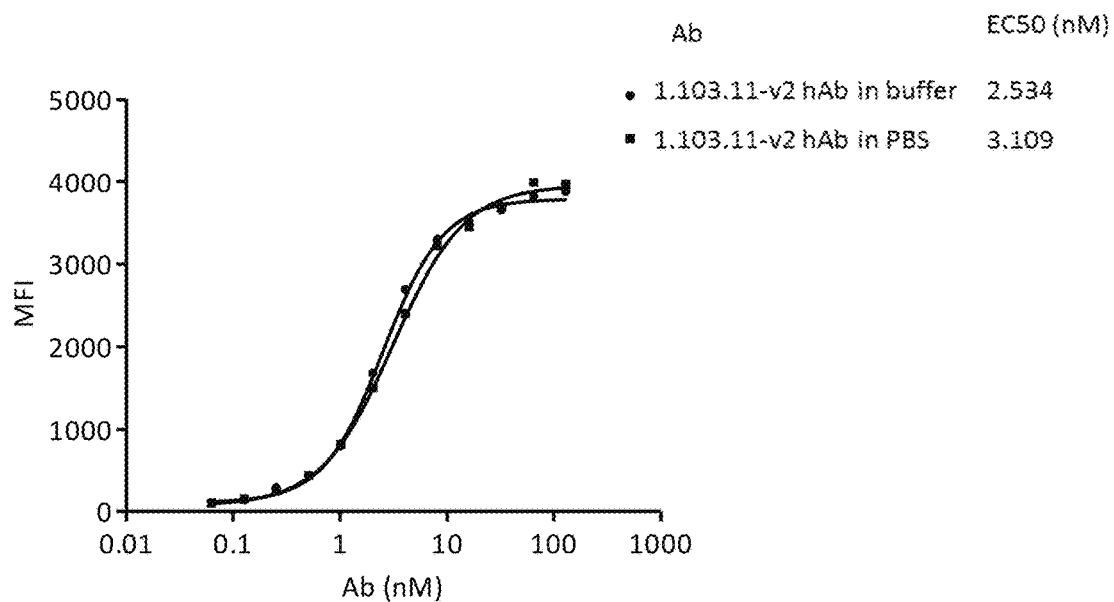
FIG. 16 shows that 1.103.11-v2 hAbs in different buffers bind to PD-1 expressing CHO cell with similar affinity measured by FACS. "1.103.11-v2 hAb in buffer" refers to the antibody in the formulation buffer, and "1.103.11-v2 hAb in PBS" refers to antibody in the 1×PBS, pH 7.4.

The binding affinity of 1.103.11-v2 hAb to human PD-1 was measured by FACS and ELISA assay. FIG. 16 shows the binding of 1.103.11-v2 hAbs in different buffers to PD-1 expressing CHO cell, and the binding was also tested under the same condition as that of FACS assay as described above, except that the antibody was either in formulation buffer or in 1×PBS (pH 7.4) and the CHO-S cells expressing human PD-1 were transferred in to 96-well U-bottom plates (BD) at a density of $2×10^5$ cells/ml. The result was comparable to that of 1.103.11 hAb. "1.103.11-v2 hAb in buffer" refers to the antibody in the formulation buffer, and "1.103.11-v2 hAb in PBS" refers to antibody in the 1×PBS, pH 7.4. Antibodies in both solutions bound to cell surface PD-1 on the CHO cell and there was no significant difference in affinity to human PD-1 between the two conditions (for 1×PBS the EC50 was about 2.52 nmol/L, and for formulation buffer it was about 3.12 nmol/L).

Figure 15:
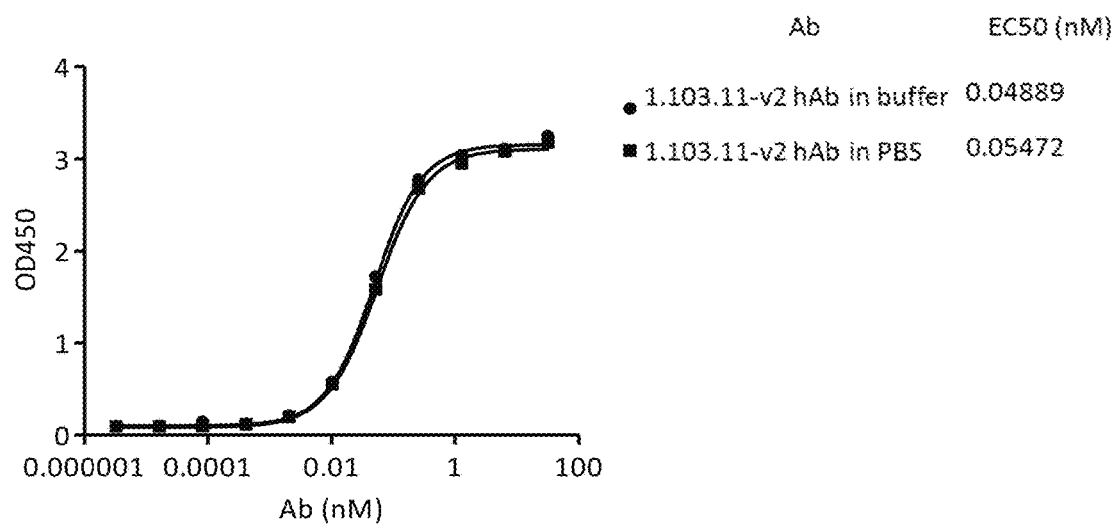
FIG. 15 shows that 1.103.11-v2 hAbs in different buffers bind to human PD-1 extracellular domain with similar affinity measured by ELISA. "1.103.11-v2 hAb in buffer" refers to the antibody in the formulation buffer, and "1.103.11-v2 hAb in PBS" refers to antibody in the 1×PBS, pH 7.4.

FIG. 15 shows the binding of antibody 1.103.11-v2 hAbs to PD-1 protein in different solutions measured by ELISA. Following the same ELISA protocol as described above, the incubation time for 1.103.11-v2 hAb was 2 h, and the incubation time for the secondary antibody goat anti-human IgG FcHRP (1:5000, Abcam) was 1 h. "1.103.11-v2 hAb in buffer" refers to the antibody in the formulation buffer, and "1.103.11-v2 hAb in PBS" refers to antibody in the 1×PBS (pH 7.4). Binding affinity to human PD-1 was demonstrated under both conditions.

Figure 4:
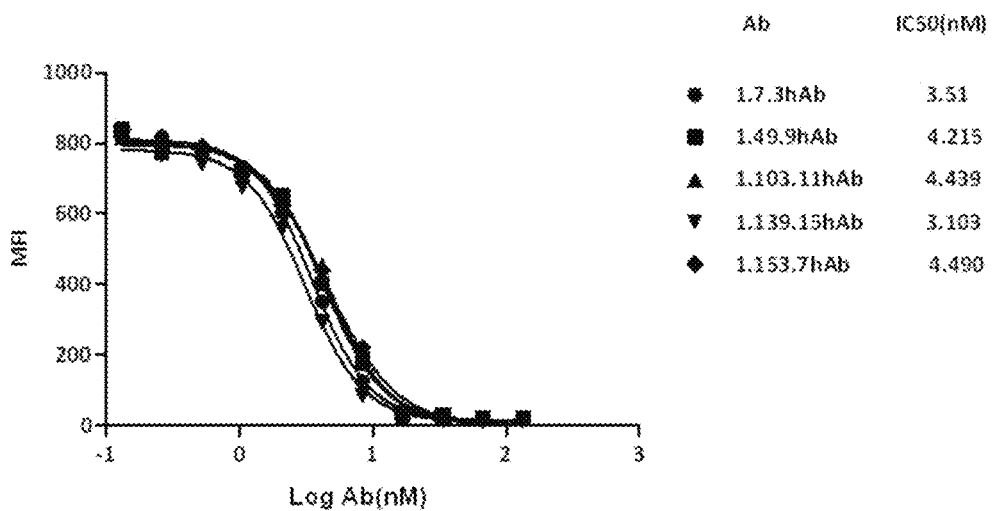
FIG. 4 shows that the fully human anti-PD-1 antibodies blocked the binding of PD-L1 to PD-1 transfected CHO cells with IC50 of about 3-8 nM as measured by FACS analysis.

CHO cells expressing human PD-1 were incubated with different concentrations of the antibodies against PD-1, then the mouse Fc-tagged human PD-L1 was added to the cells. The binding of human PD-L1 to PD-1 expressing cell was detected by using FITC-conjugated goat anti-mouse IgG, followed by the FACS analysis. As shown in FIG. 4, antibodies against PD-1 blocked the binding of PD-L1 to PD-1 transfected CHO cells. The 1.103.11-v2 hAb was also tested for blockade of PD-L1 binding to PD-1 transfected CHO cells, and the result was comparable to that of 1.103.11 hAb.

3.2 Full Kinetic Binding Affinity Tested by Surface Plasmon Resonance (SPR):

Antibodies were characterized for affinity and binding kinetics to PD-1 by SPR assay using ProteOn XPR36 (Bio-Rad). Protein A protein (Sigma) was immobilized to a GLM sensor chip (Bio-Rad) through amine coupling. Purified antibodies were flowed over the sensor chip and captured by the Protein A. The chip was rotated 90° and washed with running buffer (1×PBS/0.01% Tween20, Bio-Rad) until the baseline is stable. Five concentrations of human PD-1 and running buffer were flowed against the antibody flow cell at a flow rate of 100 μL/min for an association phase of 240s, followed by 600s dissociation. The chip was regenerated with pH 1.7 $H_3PO_4$ after each run. The association and dissociation curve was fit to a 1:1 Langmiur binding model using ProteOn software.

Figures 7, 8:
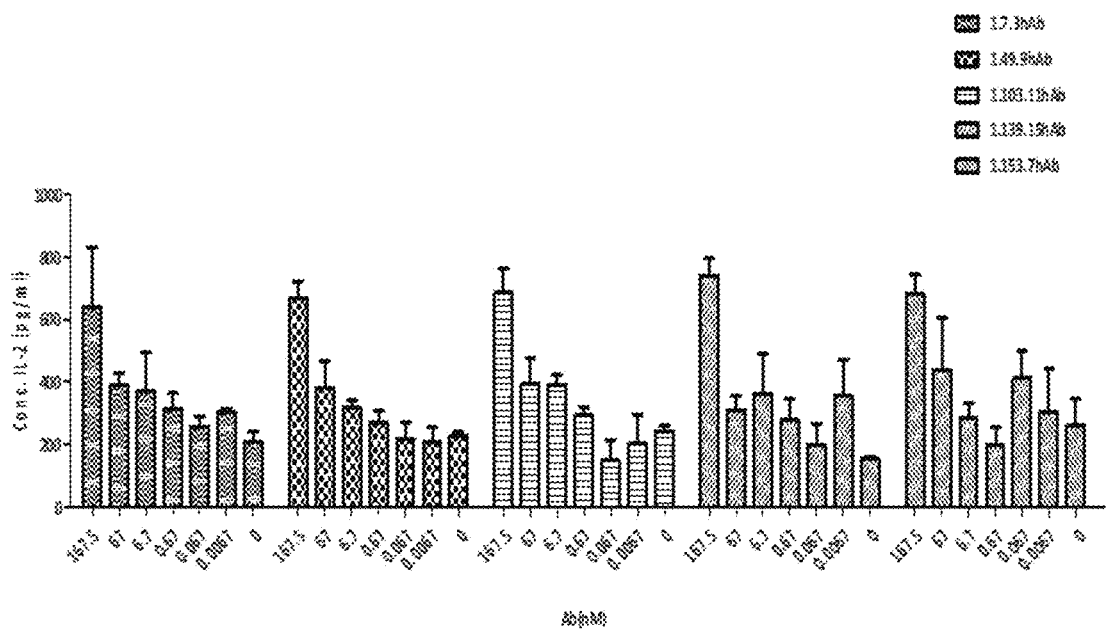
FIG. 7 is the full kinetics of binding affinity of PD-1 antibodies to human PD-1 ranging from 3.76E-9 to 1.76E-10 mol/L as determined by surface plasmon resonance.
FIG. 8 illustrates the effect of fully human anti-PD-1 antibodies on IL-2 production in mixed lymphocyte reaction (MLR).

As shown in FIG. 7, using surface plasmon resonance, the affinities of antibodies against PD-1 for recombinant human PD-1 were from 3.76E-9 to 1.76E-10 mol/L. The affinity of 1.103.11-v2 hAb is expected to be comparable to that of 1.103.11 hAb.

3.3 Orthologue (Cross-Species) and Homologue (Cross-Families) Screen:

3.3.1 Cross-Reactivity to Cynomolgus PD-1 and Murine PD-1:

Cross-reactivity was measured by ELISA. Plates (Nunc) were coated with cynomolgus PD-1 (Sino Biological) and murine PD-1 (Sino biological) at 1 μg/ml overnight at 4° C. After blocking and washing, 1 μg/ml antibodies were added to the plates and incubated at room temperature for 1 h. The plates were then washed and subsequently incubated with secondary antibody goat anti rat IgG1 HRP (Bethyl) and goat anti rat IgG2b HRP (Bethyl) for 45 min. After washing, TMB substrate was added and the interaction was stopped by 2M HCl. The absorbance at 450 nm was read using a microplate reader (Molecular Device).

Figure 6:
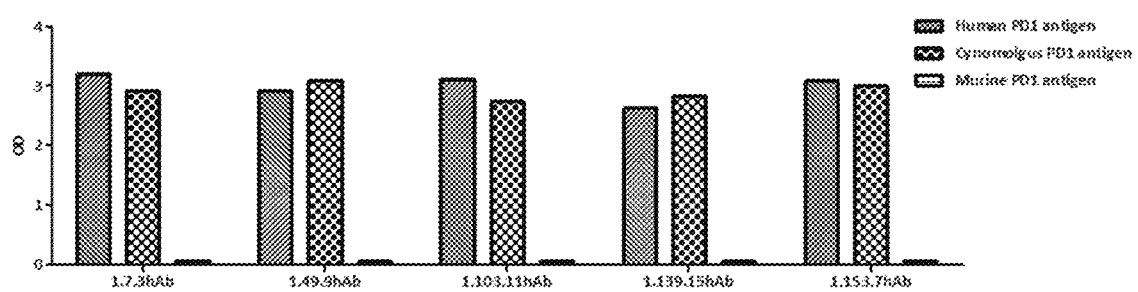
FIG. 6 shows that the fully human anti-PD-1 antibodies against PD-1 bind to cynomolgus monkey PD-1 but not murine PD-1.

The result of cross-species experiment demonstrates that antibodies against PD-1 bind to cynomolgus monkey PD-1 but not bind to murine PD-1 (FIG. 6). The 1.103.11-v2 hAb in the same experiment is expected to have comparable result to that of 1.103.11 hAb.

3.3.2 Cross-Reactivity to PD-1 Family Members CD28, CTLA4 and ICOS:

To examine the cross-family binding activity of the fully human antibodies, cells lines that express PD-1, CD28, CTLA4 or ICOS were stained with the antibodies, followed by $2^{nd}$ antibody staining with FITC conjugated goat anti-human IgG Fc. PD-1 expressing cells were used as positive control. Corresponding parental cell lines were used as negative controls. The stained cells were analyzed by using a BD Biosciences FACSCanto II and FlowJo Version software.

Figure 5:
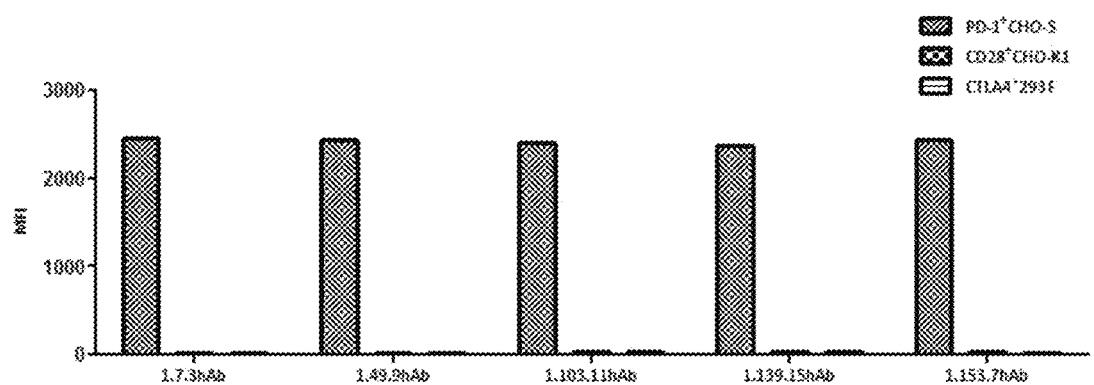
FIG. 5 shows that the fully human anti-PD-1 antibodies specifically bind to PD-1, but do not bind family members CD28 and CTLA4, as measured by FACS analysis.

FIG. 5 shows that CHO cells transfected with PD-1, CD28 and 293F transfected with CTLA4 were stained with antibodies against PD-1 and analyzed by FACS. The result demonstrates PD-1 antibodies bind specifically to PD-1, but not to CD28 and CTLA4 of PD-1 family. The 1.103.11-v2 hAb in the same experiment is expected to have comparable result to that of 1.103.11 hAb.

3.4 Epitope Binning Test:

3.4.1 The binding epitope of PD-1 antibodies was binned against benchmark antibody A and B by SPR assay using ProteOn XPR36 (Bio-Rad. Benchmark antibodies A and B were immobilized on GLC sensor chip (Bio-Rad) through amine coupling. Human PD-1 solution was flowed over the antibody immobilized channels and captured by the benchmark antibodies. The chip was then rotated 90° and washed with running buffer until the baseline is stable. Selected antibodies were flowed over the sensor chip.

3.4.2 The binding epitope of PD-1 antibodies was binned against benchmark antibody A and B by FACS. CHO cells expressing human PD-1 at the cell surface were incubated with benchmark antibody A or B at concentration of 10 µg/ml for 1 hour. The cells were washed and the PD-1 antibodies of the disclosure were added and incubated for 1 hour. The second antibody anti-rat IgG-FITC were added and incubated for 1 hour at 4° C. The cells were then washed once and resuspended in 1×PBS/1% BSA, and analyzed by flow cytometry (BD).

The results of SPR assay and FACS for the binning test showed that the epitope on human PD-1 bound by the fully human PD-1 antibodies (i.e. 1.7.3 hAb, 1.49.9 hAb, 1.103.11 hAb, 1.139.15 hAb, and 1.153.7 hAb) was different from the existing PD-1 antibodies (i.e. benchmark antibody A and B). The 1.103.11-v2 hAb in the same experiment is expected to have comparable result to that of 1.103.11 hAb.

3.5 In Vitro Function of PD-1 Antibodies Tested by Cell-Based Assays:

3.5.1 Effects of Human PD-1 Antibodies on T Cells Proliferation.

An allogeneic response was used to test the effects of PD-1 antibodies on T lymphocytes proliferation. Primary dendritic cell (DC)-stimulated MLR was conducted in 96-well, U-bottom tissue culture plates in 200 µl of RPMI 1640 containing 10% FCS and antibiotics. DCs were mixed with $1 \times 10^5$ allogeneic total CD4+T cells at a ratio between 1:10 and 1:100 DC:T cells. Cultures were also conducted in the presence or the absence of neutralizing mAbs: human PD-1 antibodies and benchmark antibody A and B and used at 10 µg/ml. Assays were incubated for 5 days, and during the last 16 h [$^3$H]thymidine was added at 1 uCi/well. [$^3$H]thymidine incorporation was measured by scintillation counting, and proliferative responses were expressed as the mean [$^3$H]thymidine incorporation (counts per minute) of triplicate wells. Counts due to DCs alone were routinely <1000 cpm. Results shown are representative examples of a minimum of five experiments performed.

Human dendritic cells (DC) and CD4+T, CD8+T and total cells used in above allo-MLR were generated from the PBMC as following procedures: Human monocytes were purified from PBMC by negative selection using human monocyte enrichment cocktail kit according to the instructions of the manufacturer (StemCell Meylan). Briefly, PBMC were isolated from blood of healthy donor using a Ficoll-Paque gradient. Cells were washed twice with PBS, then resuspended at $1 \times 10^8$ cells/ml in isolation buffer, and incubated with the monocyte enrichment Ab mixture at 4° C. for 30 min. The cells were washed and subsequently incubated with magnetic colloid at 4° C. for 30 min. Unlabeled monocytes passed through the MACS column and were collected. To generate iDCs, monocytes were cultured in RPMI 1640 medium containing 10% FCS and antibiotics with GM-CSF (PeproTech, Rocky Hill, N.J.; 800 U/ml) and IL-4 (PeproTech; 500 U/ml) at concentration of $2 \times 10^6$ cells/ml. Half the medium was replaced every other day with GM-CSF- and IL-4-containing medium. Mature DCs were generated by stimulating iDCs with LPS (026: B6; Sigma-Aldrich, St. Louis, Mo.; 1 µg/ml) on day 5 for an additional 24 h. CD4+T, CD8+T and total T cells, were purified by negative selection by incubating PBMC with human CD4+ T, CD8+T and total T cell enrichment mixture and magnetic colloid according to the manufacturer's instructions (Stemsep).

Figure 10:
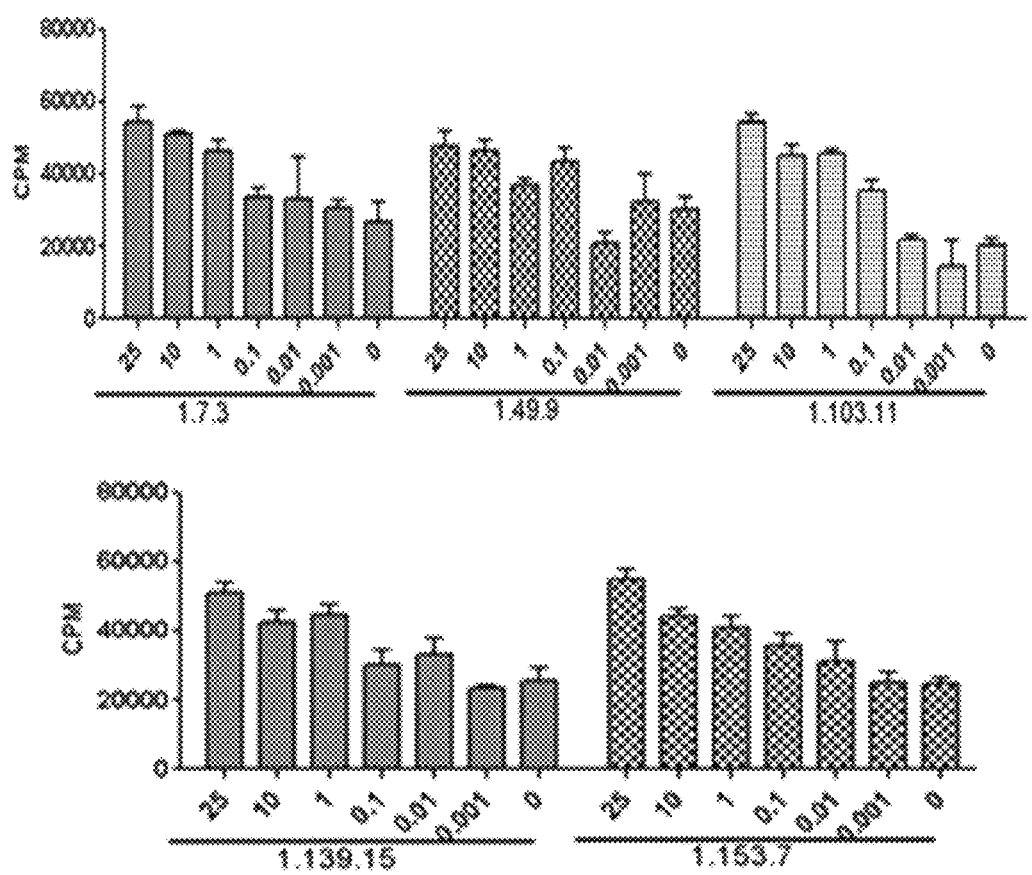
FIG. 10 shows that fully human anti-PD-1 antibodies promoted T cell proliferation in MLR.

Human CD4+ T Cells were stimulated with allogenenic DCs in the presence or absence of PD-1 antibodies 1.7.3 hAb, 1.49.9 hAb, 1.103.11 hAb, 1.139.15 hAb, and 1.153.7 hAb. The proliferation of CD4+ T cells were assessed by [$^3$H] thymidine incorporation. FIG. 10 showed that 1.7.3 hAb, 1.49.9 hAb, 1.103.11 hAb, 1.139.15 hAb, and 1.153.7 hAb enhanced concentration dependent T cell proliferation. The 1.103.11-v2 hAb in the same experiment is expected to have comparable result to that of 1.103.11 hAb.

3.5.2 Effects of Human PD-1 Antibodies on Cytokine IFNγ Secretion In Vitro:

To directly assess the effect of human PD-1 antibodies blockade on cytokine IFNγ production, we performed experiments on IFNγ production in allo-MLR. Briefly, human CD4+T cells were purified from PBMC by negative selection with CD4+T cell enrichment cocktail kit according to the instruction of the manufacturer. Immature DCs were generated from monocytes by cultured in GM-CSF and IL-4 for 5 days and mature DCs were differentiated by stimulation with LPS at 1 µg/ml for overnight. CD4+T cells were mixture with iDC/mDc at a ratio between 10:1 and 100:1 T:DC ratio. The cultures were conducted in the presence or absence of human PD-1 antibodies and benchmark antibodies. After 5 days, the supernatants from each culture were harvested for cytokine IFNγ measurement. The level of IFNγ in supernatants was measured by ELISA assay. Briefly, Coat Maxisorp plates with anti-human IFN-gamma mAb diluted in coating buffer (0.75 µg/ml; i.e.a 1/1360 dilution), 50 µl/well (i.e. for a full 96-well plate add 3.7 µl of antibody to 5 ml of coating buffer) and incubated overnight at 4° C. Block spare protein binding capacity by adding 200 µl/well of blocking buffer for 2 hours. Prepare dilutions of recombinant IFN-gamma to act as standards, two-fold dilutions from 8000 pg/ml down to 125 pg/ml, diluted in complete medium, plus complete medium alone. Wash plates and add standards and test supernatants (100 µl/well), incubate for 2-4 hours. The biotinylated anti-IFN-gamma mAb (1/1333) in blocking buffer was added followed by adding Extra-avidin Peroxidase. The reaction was developed by adding TMB substrate and stopped with 2M HCl. Measure absorbance at 450 nm.

Figure 9:
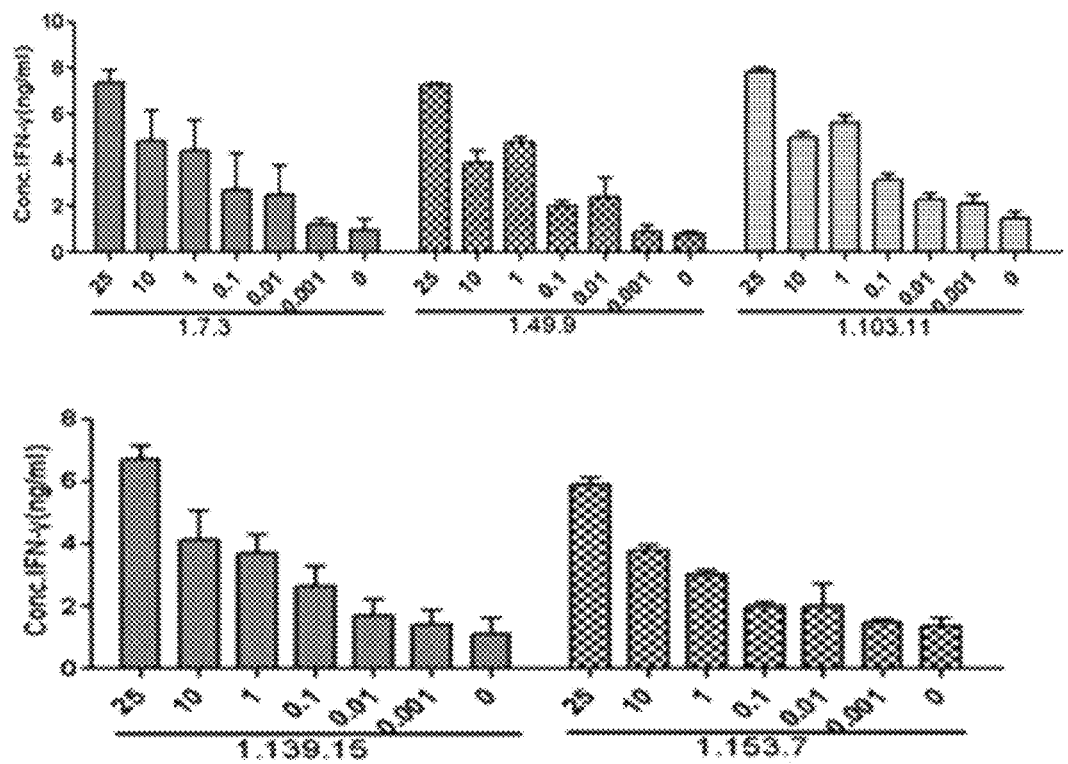
FIG. 9 illustrates the effect of fully human anti-PD-1 antibodies on IFNγ production in MLR.

FIG. 9 shows that human CD4+ T Cells were stimulated with allogenenic DCs in the presence or absence of antibodies 1.7.3 hAb, 1.49.9 hAb, 1.103.11 hAb, 1.139.15 hAb, and 1.153.7 hAb. The level of IFNγ was measured by ELISA. The result showed the fully human PD-1 antibodies increased IFNγ secretion in a dose manner. The 1.103.11-v2 hAb in the same experiment is expected to have comparable result to that of 1.103.11 hAb.

3.5.3 Effects of Human PD-1 Antibodies on Interleukin 2 (IL-2) Production In Vitro:

CD4+T cells were mixture with iDC/mDc at a ratio between 10:1 and 100:1 T:DC ratio. The cultures were conducted in the presence or absence of human PD-1 antibodies and benchmark antibodies. After 5 days, the supernatants from each culture were harvested for cytokine measurement. The level of IL-2 in supernatants was measured by ELISA assay.

FIG. 8 shows that human CD4+ T Cells were stimulated with allogenenic DCs in the presence or absence of lead antibodies or control Ab. The level of IL-2 was measured by ELISA. The results showed antibodies against PD-1 increased IL-2 secretion in a dose-dependent manner. The 1.103.11-v2 hAb in the same experiment is expected to have comparable result to that of 1.103.11 hAb.

3.5.4 Effect of human PD-1 antibodies on cell proliferation and cytokine production by autologous antigen specific immune response: in this assay, the T cells and DCs were from a same donor. Briefly, CD4+T cell were purified from PBMC and cultured in the presence of CMV pp65 peptide and low dose of IL2 (20U/ml), at the meantime, DCs were generated by culturing monocytes from the same donor's PBMC in GM-CSF and IL-4. After 5 days, the CMV pp65 peptide treated CD4+T cells were co-cultured with DCs pulsed with pp65 peptide in the absence or presence of human PD-1 antibodies and benchmark antibodies (as control). On day 5, 100 μl of supernatants were taken from each of cultures for cytokine IFNγ and IL-2 measurement. The level of IFNγ and IL-2 production was detected by ELISA assay. The proliferation of specific T cells to CMVpp65 peptide-pulsed DCs were assessed by [$^3$H]thymidine incorporation.

Figure 11:
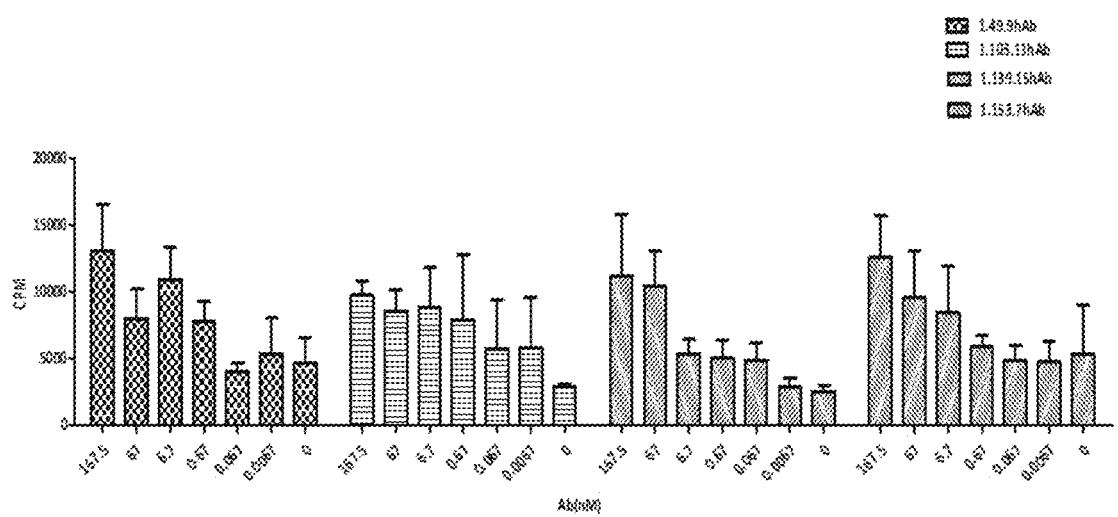
FIG. 11 shows that fully human PD-1 antibodies promoted T cell proliferation in specific T cell response.

As shown in FIG. 11, PD-1 antibodies enhanced concentration dependent CMV$^+$-CD4$^+$ T cell proliferation stimulated with CMV pp65 peptide-loaded autologous DC. The 1.103.11-v2 hAb in the same experiment is expected to have comparable result to that of 1.103.11 hAb.

Figure 12:
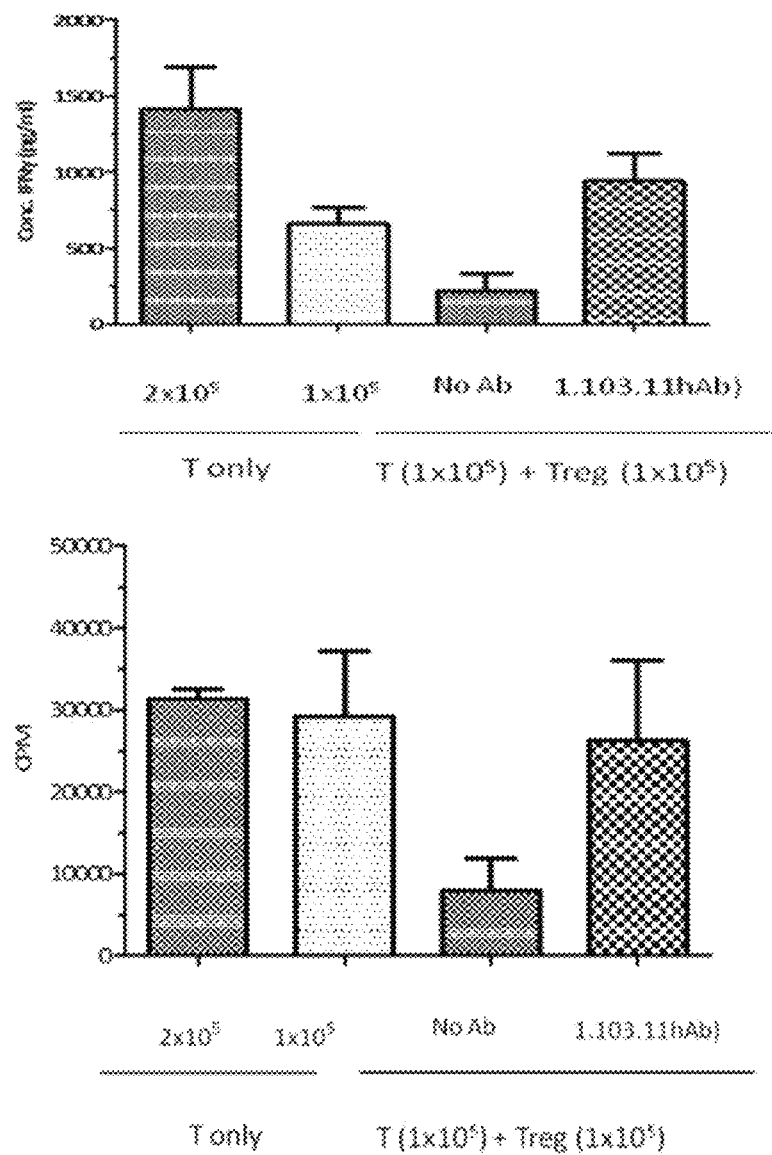
FIG. 12 shows that anti-PD-1 antibodies reversed Treg's suppressive function.

3.5.5 Effect of Human PD-1 Antibodies on Regulatory T Cell (Tregs) Suppressive Function:

Tregs, a subpopulation of T cells, are a key immune modulator and play key roles in maintaining self-tolerance. CD4+CD25+ regulatory T cell are associated with tumors because increased numbers of Tregs were found in patients with multiple cancers and is associated with a poorer prognosis. To directly assess the effect of human PD-1 antibodies on immune suppressive response, we performed experiment on Tregs. CD4$^+$CD25$^+$ and CD4$^+$CD25$^-$T cells were separated using specific anti-CD25 microbeads (Miltenyi Biotec, Auburn, Calif.) and positive or negative selection, respectively. Initially, CD4$^+$T cells were purified by negative selection by incubating PBMC with human CD4$^+$ T cell enrichment mixture and magnetic colloid according to the manufacturer's instructions (Stemsep). CD4$^+$T cells were then resuspended in MACS buffer, incubated with CD25$^+$ microbeads on ice for 30 min, washed, and loaded on the column. CD4$^+$CD25$^-$ T cells, which did not bind to the column, were collected from the flow-through and washed before use. CD4$^+$CD25$^+$T cells were subsequently retrieved from the column and washed before use. Tregs were cultured with CD4$^+$CD25$^-$T cells and DCs (Treg:Teff 1:1 ratio) in the presence or absence of human PD-1 antibodies at a concentration of 10 μg/ml. Either no antibody or isotype antibody was used as negative control. The supernatants from the cultures were taken on day 5 for cytokines detection by ELISA and the cell proliferation was measured by adding [$^3$H]thymidine at a concentration of 1 uCi/well and incubated for further 18 hours. [$^3$H]thymidine incorporation was measured by scintillation counting. As shown in FIG. 12, the PD-1 antibodies abrogated Treg's suppressive function and restored responding T cell proliferation and IFNγ secretion. The 1.103.11-v2 hAb in the same experiment is expected to have comparable result to that of 1.103.11 hAb.

3.6 Adcc/Cdc Assay:

to minimize the undesired toxicity on healthy PD-1$^+$ cells, the selected anti-PD-1 fully human antibodies were confirmed to have no ADCC and CDC function.

Figure 13:
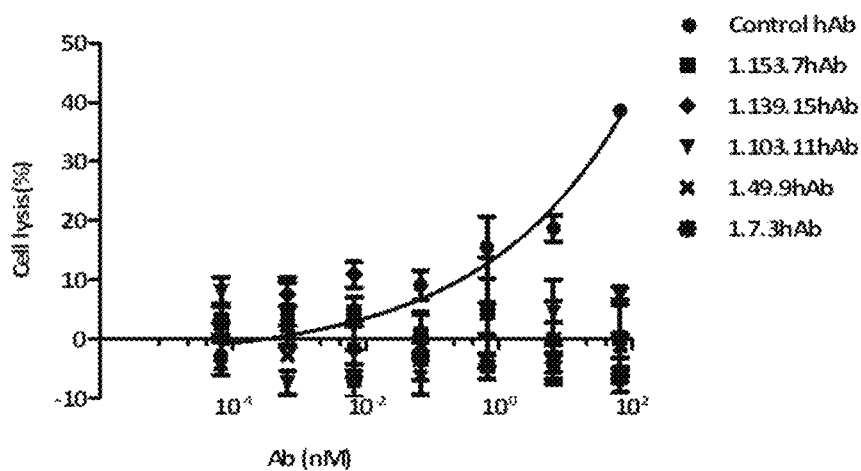
FIG. 13 shows that the anti-PD-1 antibodies lacked ADCC on activated T cells.

3.6.1 ADCC:

Activated T cells expressing high levels of cell surface PD-1 were used as target cells and were pre-incubated with various concentrations of fully human antibodies in 96-well plates for 30 min, then IL-2-activated PBMCs (used as a source of natural killer (NK) cells, i.e. the effector cells) were added at the effector/target ratio of 50:1. The plates were incubated for 6 hours at 37° C. in a 5% CO$_2$ incubator. Target cell lysis was determined by cytotoxicity detection kit (Roche). Optical density was measured by Molecular Devices SpectraMax M5e Plate Reader. Results showed that, the tested fully human antibodies against PD-1 did not mediate ADCC (FIG. 13). The 1.103.11-v2 hAb in the same experiment is expected to have comparable result to that of 1.103.11 hAb.

Figure 14:
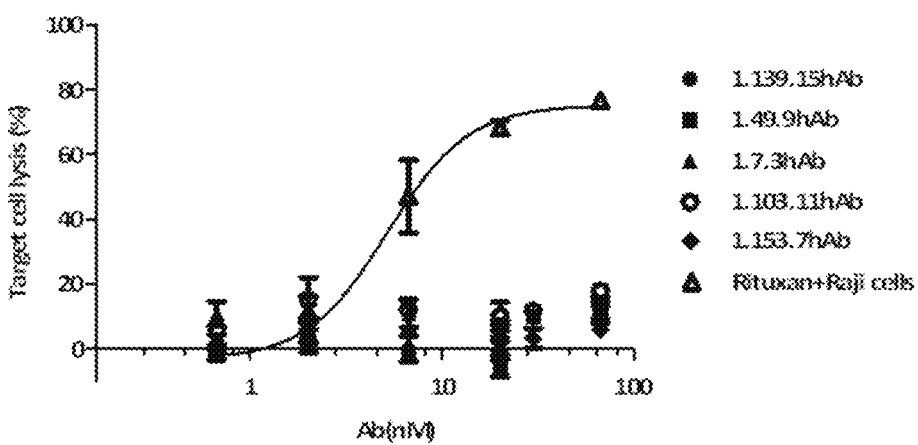
FIG. 14 shows that the anti-PD-1 antibodies lacked CDC on activated T cells.

3.6.2 CDC:

target cells (activated T cell), diluted human serum complement (Quidel-A112) and various concentrations of fully human PD-1 antibodies were mixed in a 96-well plate. The plate was incubated for 4 h at 37° C. in a 5% CO$_2$ incubator. Target cell lysis was determined by CellTiter glo (Promega-G7573). Rituxan (Roche) and human B lymphoma cell line Raji (CD20 positive) were used as positive control. The data showed that PD-1 antibodies did not mediated CDC (FIG. 14). The 1.103.11-v2 hAb in the same experiment is expected to have comparable result to that of 1.103.11 hAb.

Example 4: Epitope Mapping of the Fully Human Antibody

To determine the epitope difference between the present antibody 1.103.11 hAb provided herein and Keytruda, a known hPD-1 antibody, alanine scanning experiments on hPD-1 and the effect evaluation to antibody binding were conducted using 1.103.11 hAb, Keytruda and 11.148.10 (a control hPD-1 antibody which binds to an epitope which does not overlap with that of 1.103.11 hAb or that of Keytruda).

Alanine residues on hPD-1 were mutated to glycine codons, and all other residues were mutated to alanine codons. For each residue of the hPD-1 extracellular domain (ECD), point amino acid substitutions were made using two sequential PCR steps. A pcDNA3.3-hPD-1_ECD.His plasmid that encodes ECD of human PD-1 and a C-terminal His-tag was used as template, and a set of mutagenic primer was used for first step PCR using the QuikChange lightning multi-site-directed mutagenesis kit (Agilent technologies, Palo Alto, Calif.). Dpn I endonuclease was used to digest the parental template after mutant strand synthesis reaction. In the second-step PCR, linear DNA expression cassette which composed of a CMV promoter, an extracellular domain (ECD) of PD-1, a His-tag and a herpes simplex virus thymidine kinase (TK) polyadenylation was amplified and transiently expressed in HEK293F cells (Life Technologies, Gaithersburg, Md.).

Monoclonal antibodies 1.103.11 hAb, keytruda and 11.148.10 hAb were coated in plates for ELISA binding assay. After interacting with the supernatant that contains quantified PD-1 mutant, HRP conjugated anti-His antibody (Rockland, Cat #200-303-382) was added as detection antibody. Absorbance was normalized according to the average of control mutants. After setting an additional cutoff to the binding fold change (<0.55), the final determined epitope residues were identified.

Top 30 point-substituted hPD-1 mutants that significantly reduced antibody binding were shown in Table 2. Checking the positions of all these residues on the hPD-1 crystal structures (PDB code 3RRQ and 4ZQK) revealed that some amino acids (e.g. Val144, Leu142, Val110, Met108, Cys123 etc.) were fully buried in the protein, and were unlikely to directly contact any antibodies. The observed binding reductions most probably resulted from the instability or even collapse of hPD-1 structure after alanine substitutions. To avoid misinterpreting these data as epitope hot spots, we took advantage of a control antibody 11.148.10 hAb, which binds to a quite different location on antigen, but is expected to respond to the collapse of the hPD-1 structure if it indeed happens. Mutants that affect both antibodies were treated as false hot spots and were removed from the list. After setting an additional cutoff to the binding fold change (<0.55), the final determined epitope residues were listed in Table 3. They are 9 positions to 1.103.11 hAb and 5 positions to Keytruda, and 10 residues to the control antibody 11.148.10 hAb.

hPD-L1 binding site, were therefore mapped on the crystal structure of hPD-1 to make a better visualization and comparison. (FIG. 17).

Figure 17:
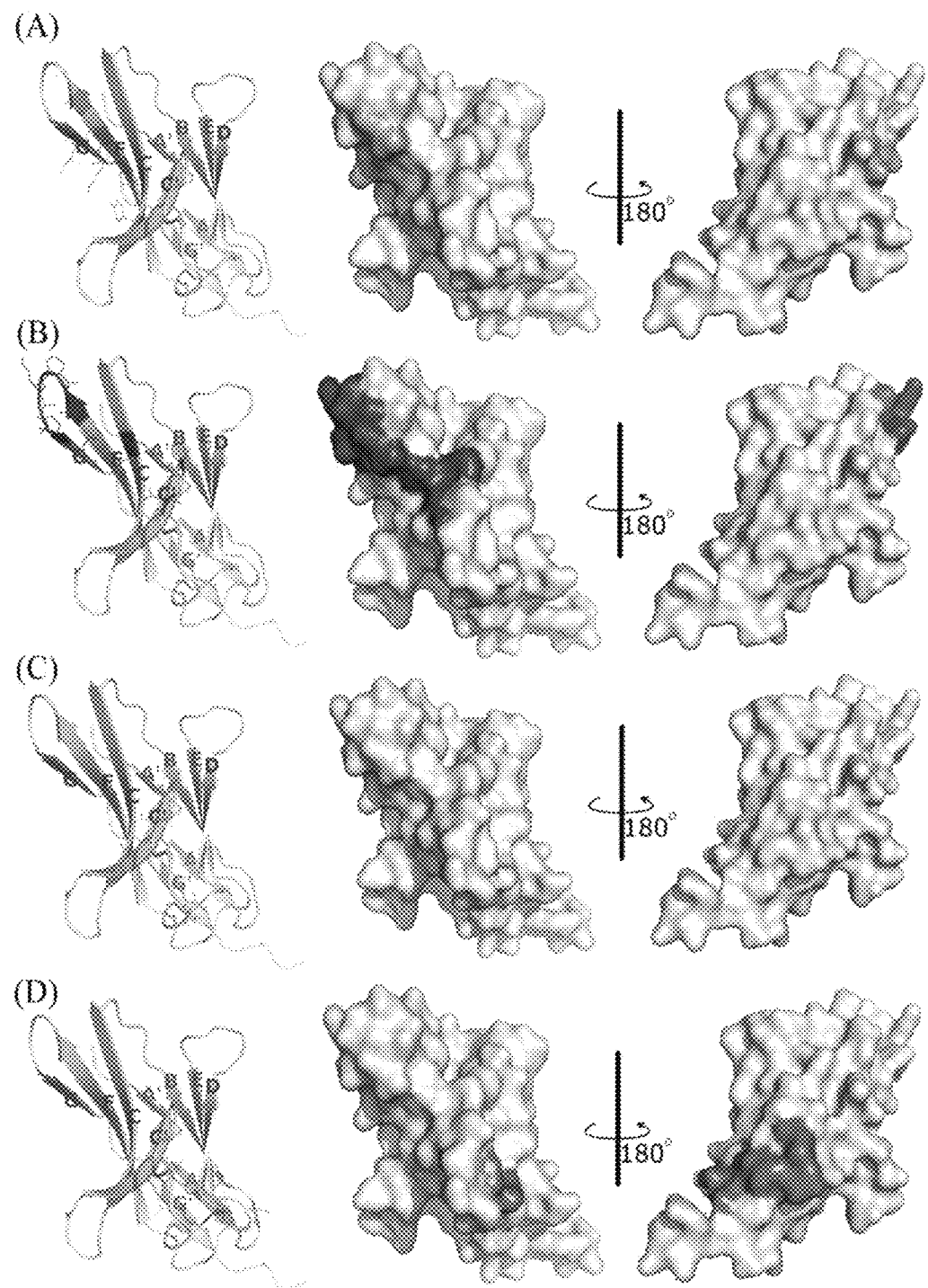
FIG. 17 shows the hot-spot residues (shadow area) on the crystal structure of the human PD-L1 that antibodies bind to. A shows the common hot-spot residues; B-D show the hot-spot residues for 1.103.11 hAb, Keytruda and 11.148.10 hAb, respectively.

As shown in FIG. 17, the hot-spot residues in charge of the hPD-L1 binding all gathered in the middle of C, F and G strands (FIG. 17A). Two investigated antibodies 1.103.11

TABLE 2

The effect of PD-1 point mutations on antibody binding

| 1.103.11 hAb | | | Keytruda | | | 11.148.10 hAb | |
|---|---|---|---|---|---|---|---|
| PD-1 #Residue | fold change $^a$ | SD | PD-1 #Residue | fold change $^a$ | SD | PD-1 #Residue | fold change $^a$ | SD |
| V 144 | 0.22 | 0.00 | P 89 | 0.18 | 0.02 | V 144 | 0.03 | 0.01 |
| A 129 | 0.22 | 0.00 | D 85 | 0.38 | 0.01 | F 56 | 0.06 | 0.02 |
| D 85 | 0.24 | 0.01 | V 144 | 0.40 | 0.01 | L 142 | 0.09 | 0.00 |
| P 83 | 0.30 | 0.01 | R 94 | 0.46 | 0.04 | D 48 | 0.21 | 0.01 |
| L 128 | 0.32 | 0.01 | F 106 | 0.47 | 0.05 | R 143 | 0.26 | 0.01 |
| V 64 | 0.32 | 0.01 | K 78 | 0.48 | 0.00 | C 123 | 0.27 | 0.01 |
| Q 133 | 0.37 | 0.03 | P 83 | 0.50 | 0.01 | F 106 | 0.29 | 0.04 |
| P 130 | 0.41 | 0.00 | D 92 | 0.50 | 0.02 | V 44 | 0.34 | 0.01 |
| F 106 | 0.41 | 0.02 | P 39 | 0.54 | 0.00 | L 41 | 0.35 | 0.00 |
| K 131 | 0.43 | 0.01 | A 81 | 0.57 | 0.01 | A 50 | 0.35 | 0.02 |
| L 142 | 0.44 | 0.00 | C 123 | 0.57 | 0.01 | F 95 | 0.37 | 0.01 |
| C 123 | 0.46 | 0.00 | N 66 | 0.57 | 0.03 | V 43 | 0.37 | 0.01 |
| A 132 | 0.53 | 0.01 | L 142 | 0.59 | 0.01 | V 110 | 0.41 | 0.01 |
| P 39 | 0.55 | 0.02 | F 82 | 0.61 | 0.03 | M 108 | 0.43 | 0.11 |
| M 108 | 0.56 | 0.00 | F 95 | 0.61 | 0.04 | R 94 | 0.46 | 0.12 |
| F 52 | 0.59 | 0.00 | F 52 | 0.63 | 0.01 | C 93 | 0.48 | 0.03 |
| K 135 | 0.62 | 0.01 | M 108 | 0.64 | 0.06 | R 86 | 0.49 | 0.01 |
| S 137 | 0.62 | 0.01 | L 128 | 0.68 | 0.01 | D 117 | 0.49 | 0.12 |
| F 95 | 0.63 | 0.02 | I 126 | 0.72 | 0.01 | A 113 | 0.51 | 0.01 |
| I 126 | 0.64 | 0.01 | A 113 | 0.72 | 0.01 | T 45 | 0.51 | 0.03 |
| F 82 | 0.65 | 0.01 | V 110 | 0.73 | 0.04 | L 42 | 0.53 | 0.01 |
| I 134 | 0.69 | 0.01 | G 47 | 0.73 | 0.01 | A 40 | 0.54 | 0.00 |
| R 94 | 0.70 | 0.01 | D 117 | 0.73 | 0.07 | P 39 | 0.55 | 0.00 |
| A 50 | 0.73 | 0.01 | N 49 | 0.73 | 0.00 | G 90 | 0.56 | 0.08 |
| D 117 | 0.73 | 0.01 | S 87 | 0.74 | 0.06 | N 49 | 0.58 | 0.01 |
| A 113 | 0.73 | 0.02 | L 42 | 0.76 | 0.01 | S 137 | 0.58 | 0.02 |
| N 49 | 0.73 | 0.01 | N 102 | 0.76 | 0.01 | Y 68 | 0.58 | 0.03 |
| L 65 | 0.75 | 0.01 | W 67 | 0.81 | 0.01 | W 67 | 0.60 | 0.03 |
| W 67 | 0.76 | 0.01 | P 101 | 0.81 | 0.04 | F 52 | 0.60 | 0.05 |
| G 47 | 0.77 | 0.00 | A 80 | 0.82 | 0.01 | R 69 | 0.61 | 0.05 |

Bold: amino acids overlapped with control 11.148.10 hAb for structure maintaining which were excluded from the hot spots list.
$^a$ Fold change in binding is relative to the binding of several silent alanine substitutions.

TABLE 3

Identification of potential epitopes

| PD-1 to 1.103.11 hAb | residue location | PD-1 to Keytruda | residue location | PD-1 to 11.148.10 hAb | residue location |
|---|---|---|---|---|

What is claimed is:

1. An isolated polynucleotide encoding an antibody comprising a heavy chain variable region comprising SEQ ID NO: 53 and a light chain variable region comprising SEQ ID NO: 67.

2. The isolated polynucleotide of claim 1, wherein the antibody is an IgG4 antibody.

3. An isolated polynucleotide encoding an scFv comprising a heavy chain variable region comprising SEQ ID NO: 53; and a light chain variable region comprising SEQ ID NO: 67.

4. A vector comprising the isolated polynucleotide of claim 1.

5. A vector comprising the isolated polynucleotide of claim 3.

6. A host cell comprising the vector of claim 4.

7. A host cell comprising the vector of claim 5.

8. A method for expressing an antibody comprising a heavy chain variable region comprising SEQ ID NO: 53; and a light chain variable region comprising SEQ ID NO: 67, the method comprising culturing the host cell of claim 5 under conditions at which an antibody comprising a heavy chain variable region comprising SEQ ID NO: 53; and a light chain variable region comprising SEQ ID NO: 67 is expressed.

9. The method of claim 8, wherein the antibody is an IgG4 antibody.

* * * * *